United States Patent [19]

Abelman et al.

[11] Patent Number: 5,696,231
[45] Date of Patent: Dec. 9, 1997

[54] N-SUBSTITUTED GLYCINE DERIVATIVES AS ENZYME INHIBITORS

[75] Inventors: Matthew Mark Abelman, Solana Beach; Todd Anthony Miller, Encinitas; Ruth Foelsche Nutt, San Diego, all of Calif.

[73] Assignee: Corvas International, Inc., San Diego, Calif.

[21] Appl. No.: 361,794

[22] Filed: Dec. 21, 1994

[51] Int. Cl.$^6$ .............................. C07K 5/00; C07K 7/00; C07K 17/00; A61K 38/00
[52] U.S. Cl. ........................................ 530/331; 514/18
[58] Field of Search ....................... 530/331; 514/18

[56] References Cited

U.S. PATENT DOCUMENTS

| | | |
|---|---|---|
| 4,883,863 | 11/1989 | Abe et al. . |
| 5,380,713 | 1/1995 | Balasubramaniam et al. ............ 514/18 |

FOREIGN PATENT DOCUMENTS

| | | |
|---|---|---|
| 185390 | 12/1985 | European Pat. Off. . |
| 672659 | 3/1995 | European Pat. Off. . |
| 4371 | 3/1992 | WIPO . |
| 13693 | 6/1994 | WIPO . |
| 28420 | 10/1995 | WIPO . |

OTHER PUBLICATIONS

Szelke et al, Brazilian J. Med. Biol. Res. vol. 27 p. 1943, 1994.

*Primary Examiner*—Toni R. Scheiner
*Assistant Examiner*—Sheela J. Huff
*Attorney, Agent, or Firm*—Lyon & Lyon LLP

[57] ABSTRACT

The present invention discloses peptide aldehydes which are potent inhibitors of factor Xa, their pharmaceutically acceptable salts, pharmaceutically acceptable compositions thereof, and methods of using them as therapeutic agents for disease states in mammals characterized by abnormal thrombosis.

24 Claims, 5 Drawing Sheets

N-SUBSTITUTED GLYCINE DERIVATIVES AS ENZYME INHIBITORS

TECHNICAL FIELDS

In one aspect, the present invention relates to compounds which are potent inhibitors of factor Xa. In another aspect, the present invention relates to novel peptide aldehydes, their pharmaceutically acceptable salts, and pharmaceutically acceptable compositions thereof which are useful as potent inhibitors of blood coagulation in vitro and in vivo in mammals. In yet another aspect, the invention relates to methods of using these inhibitors as therapeutic agents for disease states in mammals characterized by abnormal thrombosis. In a further aspect, the invention relates to methods of using these inhibitors as in vitro diagnostic agents.

BACKGROUND

Normal hemostasis is the result of a delicate balance between the processes of clot formation (blood coagulation) and clot dissolution (fibrinolysis). The complex interactions between blood cells, specific plasma proteins and the vascular surface, maintain the fluidity of blood unless injury occurs. Damage to the endothelial barrier lining the vascular wall exposes underlying tissue to these blood components. This in turn triggers a series of biochemical reactions altering the hemostatic balance in favor of blood coagulation which can either result in the desired formation of a hemostatic plug stemming the loss of blood or the undesirable formation of an occlusive intravascular thrombus resulting in reduced or complete lack of blood flow to the affected organ.

The blood coagulation response is the culmination of a series of amplified reactions in which several specific zymogens of serine proteases in plasma are activated by limited proteolysis. This series of reactions results in the formation of an insoluble matrix composed of fibrin and cellular components which is required for the stabilization of the primary hemostatic plug or thrombus. The initiation and propagation of the proteolytic activation reactions occurs through a series of amplified pathways which are localized to membranous surfaces at the site of vascular injury (Mann, K. G., Nesheim, M. E., Church, W. R., Haley, P. and Krishnaswamy, S. (1990) Blood 76: 1–16. and Lawson, J. H., Kalafatis, M., Stram, S., and Mann, K. G. (1994) J. Biol. Chem. 269: 23357–23366).

Initiation of the blood coagulation response to vascular injury follows the formation of a catalytic complex composed of serine protease factor VIIa and the non-enzymatic co-factor, tissue factor (TF)(Rappaport, S. I. and Rao, L. V. M. (1992) Arteriosclerosis and Thrombosis 12: 1112–1121). This response appears to be exclusively regulated by the exposure of subendothelial TF to trace circulating levels of factor VIIa and its zymogen factor VII, following a focal breakdown in vascular integrity. Autoactivation results in an increase in the number of factor VIIa/TF complexes which are responsible for the formation of the serine protease factor Xa. It is believed that in addition to the factor VIIa/TF complex, the small amount of factor Xa which is formed primes the coagulation response through the proteolytic modification of factor IX to factor $IX_{alpha}$ which in turn is converted to the active serine protease factor $IXa_b$ by the factor VIIa/TF complex (Mann, K. G., Krishnaswamy, S. and Lawson, J. H. (1992) Sem. Hamatology 29: 213–226.). It is factor $IXa_b$ in complex with activated factor VIIIa, which appears to be responsible for the production of significant quantities of factor Xa which subsequently catalyzes the penultimate step in the blood coagulation cascade; the formation of the serine protease thrombin.

Factor Xa catalyzes the formation of thrombin following the assembly of the prothrombinase complex which is composed of factor Xa, the non-enzymatic co-factor Va and the substrate prothrombin (factor II) assembled in most cases, on the surface of activated platelets which are adhered at the site of injury (Fuster, V., Badimon, L., Badimon, J. J. and Chesebro, J. H. (1992) New Engl. J. Med. 326: 310–318). In the arterial vasculature, the resulting amplified "burst" of thrombin generation catalyzed by prothrombinase results locally high levels of this protease which is responsible for the formation of fibrin and the further recruitment of additional platelets as well as the covalent stabilization of the clot through the activation of the transglutaminase zymogen factor XIII. In addition, the coagulation response is further propagated through the thrombin-mediated proteolytic feedback activation of the non-enzymatic co-factors V and VIII resulting in more prothrombinase formation and subsequent thrombin generation (Hemker, H. C. and Kessels, H. (1991) Haemostasis 21: 189–196).

Substances which interfere in the process of blood coagulation (anticoagulants) have been demonstrated to be important therapeutic agents in the treatment and prevention of thrombotic disorders (Kessler, C. M. (1991) Chest 99: 97S-112S and Cairns, J. A., Hirsh, J., Lewis, H. D., Resnekov, L., and Theroux, P. (1992) Chest 102: 456S-481S). The currently approved clinical anticoagulants have been associated with a number of adverse effects owing to the relatively non-specific nature of their effect on the blood coagulation cascade (Levine, M. N., Hirsh, J., Landefeld, S., and Raskob, G. (1992) Chest 102: 352S-363S). This has stimulated the search for more effective anticoagulant agents which can more effectively control the activity of the coagulation cascade by selectively interfering with specific reactions in this process which may have a positive effect in reducing the complications of anticoagulant therapy (Weitz, J., and Hirsh, J. (1993) J. Lab. Clin. Med. 122: 364–373). In another aspect, this search has focused on normal human proteins which serve as endogenous anticoagulants in controlling the activity of the blood coagulation cascade. In addition, various hematophageous organisms have been investigated because of their ability to effectively anticoagulate the blood meal during and following feeding on their hosts suggesting that they have evolved effective anticoagulant strategies which may be useful as therapeutic agents.

A plasma protein, Lipoprotein-Associated Coagulation Inhibitor (LACI) or recently termed Tissue Factor Pathway Inhibitor (TFPI), containing three consecutive Kunitz domains has been reported to inhibit the enzyme activity of factor Xa directly and, in a factor Xa-dependent manner, inhibit the enzyme activity the factor VIIa-tissue factor complex. Salvensen, G., and Pizzo, S. V., "Proteinase Inhibitors: a-Macroglobulines, Serpins, and Kunis", "Hemostasis and Thrombosis, Third Edition, pp. 251–253, J. B. Lippincott Company (Edit. R. W. Colman et al. 1994). A cDNA sequence encoding TFPI has been reported, and the cloned protein was reported to have a molecular weight of 31,950 daltons and contain 276 amino acids. Broze, G. J. and Girad, T. J., U.S. Pat. No. 5,106,833, col. 1, (1992). Various recombinant proteins derived from TFPI have been reported. Girad, T. J. and Broze, G. J., EP 439,442 (1991); Rasmussen, J. S. and Nordfand, O. J., WO 91/02753 (1991); and Broze, G. J. and Girad, T. J., U.S. Pat. No. 5,106,833, col. 1, (1992).

Antistasin, a protein comprised of 119 amino acids and found in the salivary gland of the Mexican leech, Haemen-

*teria officinalis*, has been reported to inhibit the enzyme activity of factor Xa. Tuszynski et al. (1987) J. Biol. Chem., 262:9718; Nutt, et al. (1988) J. Biol. Chem., 263:10162. A 6,000 daltons recombinant protein containing 58 amino acids with a high degree of homology to antistasin's amino-terminus amino acids 1 through 58 has been reported to inhibit the enzyme activity of factor Xa. Tung, J. et al., EP 454,372 (1991); Tung, J. et al., U.S. Pat. No. 5,189,019 (1993).

Tick Anticoagulant Protein (TAP), a protein comprised of 60 amino acids and isolated from the soft tick, *Ornithodoros moubata*, has been reported to inhibit the enzyme activity of factor Xa but not factor VIIa. Waxman, L. et al. (1990) Science, 248:593. TAP made by recombinant methods has been reported. Vlausk, G. P. et al., EP 419,099 (1991) and Vlausk, G. P. et al., U.S. Pat. No. 5,239,058 (1993).

The dog hookworm, *Ancylostoma caninum*, which can also infect humans, has been reported to contain a potent anticoagulant substance. *A. caninum* was reported to contain a substance which inhibited coagulation of blood in vitro. Loeb, L. and Smith, A. J. (1904) Proc. Pathol. Soc. Philadelphia, 7:173–178. Extracts of *A. caninum* were reported to prolong prothrombin time and partial thromboplastin time in human plasma with the anticoagulant effect being reported attributable to inhibition of factor Xa but not thrombin. Spellman, Jr., J. J. and Nossel, H. L. (1971) Am. J. Physiol., 220:922–927. More recently, soluble protein extracts of *A. caninum* were reported to prolong prothrombin time and partial thromboplastin time in human plasma in vitro. The anticoagulant effect was reported to be attributable to inhibition of human factor Xa but not thrombin. Cappello, M. et al. (1993) J. Infect. Diseases, 167:1474–1477.

SUMMARY OF THE INVENTION

The present invention is directed to novel compounds which are peptide argininals which include N-substituted glycine groups as part of the peptide backbone. These compounds are potent inhibitors of factor Xa in vivo and in vitro.

Thus, in one aspect, the present invention is directed to compounds of the formula:

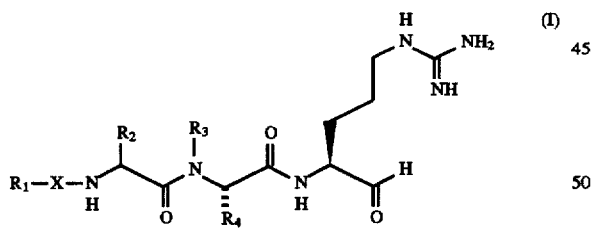

wherein (a) X is selected from the group consisting of —S(O)$_2$—, —N(R')—S(O)$_2$—, —C(=O)—, —OC(=O)—, —NH—C(=O)—, and a direct link, wherein R' is hydrogen, or alkyl of 1 to about 4 carbon atoms;

(b) R$_1$ is selected from the group consisting of:
  (1) alkyl of 1 to about 12 carbon atoms,
  (2) alkyl of 1 to about 3 carbon atoms substituted with cyclic alkyl of about 5 to about 8 carbon atoms,
  (3) alkenyl of about 3 to about 6 carbon atoms which is optionally substituted with cyclic alkyl of about 5 to about 8 carbon atoms,
  (4) aryl of about 4 to about 14 carbon atoms which is optionally mono-substituted with Y1 or optionally di-substituted with Y$_1$ and Y$_2$,
  (5) aralkyl of about 5 to about 15 carbon atoms which is optionally mono-substituted in the aryl ring with Y$_1$ or optionally di-substituted in the aryl ring with Y$_1$ and Y$_2$,
  (6) aralkenyl of about 6 to about 15 carbon atoms which is optionally mono-substituted in the aryl ring with Y$_1$ or optionally di-substituted in the aryl ring with Y$_1$ and Y$_2$.

 (7)

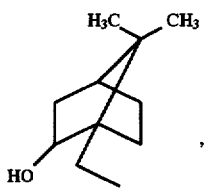 (8)

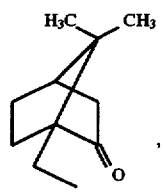 (9)

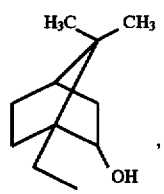 (10)

(11) perfluoroalkyl of 1 to about 12 carbon atoms,
(12) perfluoroaryl of about 6 to about 14 carbon atoms,
(13) perfluoroaryl alkyl of about 7 to about 15 carbon atoms, and
(14)

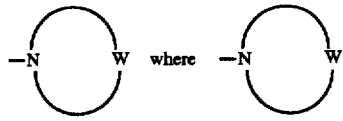

is a 5 to 7 member heterocycle of 3 to 6 ring carbon atoms, where W is —CH$_2$—, —O—, —S(=O)—, —S(O)$_2$— or —S—, where Y$_1$ and Y$_2$ are independently selected from halogen, —CF$_3$, —CF$_2$CF$_3$, —CH(CF$_3$)$_2$, —C(OH)(CF$_3$)$_2$, cyano, nitro, —C(O)OH, —C(O)OZ$_1$, —Z$_1$, —OZ$_1$, —OH, —NH$_2$, —NHZ$_1$, —NZ$_1$Z$_2$, —P(O)$_3$H$_2$, —P(O)$_3$(Z$_1$)$_2$, tetrazolyl, —S(O)$_3$H and —S(O)$_m$Z$_1$ wherein m is 0, 1 or 2, Z$_1$ and Z$_2$ are independently selected from the group consisting of alkyl of 1 to about 6 carbon atoms, aryl of about 3 to about 14 carbon atoms and aralkyl of about 4 to about 15 carbon atoms, with the provisos that:

(1) when Y$_1$ is halogen, then Y$_2$ is hydrogen or halogen;
(2) when Y$_1$ is —C(O)OH, then Y$_2$ is hydrogen, —OH or —C(O)OH;

(3) when $Y_1$ is —C(O)O$Z_1$, then $Y_2$ is hydrogen, —OH or —C(O)O$Z_1$;

(4) when $Y_1$ is —$Z_1$, then $Y_2$ is hydrogen, —OH or —$Z_1$;

(5) when $Y_1$ is —$CF_3$, then $Y_2$ is hydrogen, —OH or —$CF_3$;

(6) when $Y_1$ is —O$Z_1$, then $Y_2$ is hydrogen, —OH or —O$Z_1$;

(7) when $Y_1$ is —OH, then $Y_2$ is hydrogen, —OH, —C(O)OH, C(O)O$Z_1$, —$CF_3$, —S(O)$_3$H, or —S(O)$_m Z_1$; and (8) when $Y_1$ is cyano, nitro, —P(O)$_3$H$_2$, —P(O)$_3$($Z_1$)$_2$, —NH$_2$, —NH$Z_1$, —N$Z_1 Z_2$, or tetrazolyl, then $Y_2$ is hydrogen;

(c) $R_2$ is selected from the group consisting of hydrogen, —CH$_2$CH$_2$CH$_2$NHC(=NH)NH$_2$, —CH$_2$CH$_2$S(O)$_2$CH$_3$, —CH$_2$C(O)OH, —CH$_2$C(O)OCH$_3$, —CH$_2$S(O)$_2$(CH$_2$)$_n$C(O) $Z_3$,

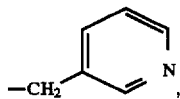

—CH$_2$S(O)$_2 Z_4$, —(CH$_2$)$_n$NH$_2$, —(CH$_2$)$_n$C(O)NR$_5 R_6$, and

wherein n=2, 3, 4, 5, or 6, $Z_3$ is —OH, —OCH$_3$, or —NR$_5 R_6$, $Z_4$ is alkyl of 1 to about 4 carbon atoms, aryl of about 6 to about 14 carbon atoms, or aralkyl of about 7 to 16 carbon atoms, $R_5$ is hydrogen or methyl, $R_6$ is a cyclic alkyl of 1 to about 10 carbon atoms, an aralkyl of about 5 to about 15 carbon atoms optionally monosubstituted with $Y_1$, or heterocyclic hydrocarbyl of 5 to 10 ring atoms with 3 to about 9 ring carbon atoms and the remainder of the ring atoms are heteroatoms selected from oxygen, sulfur and nitrogen, optionally subustituted, wherein $Y_1$ is as defined above,

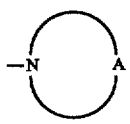

is 6,7-dimethoxy-1,2,3,4-tetrahydroisoquinolinyl, 4-hydroxypiperidyl, 4-keto piperidyl, N-morpholino, 3,4-methylenedioxybenzyl piperazinyl, 4-phenyl piperazinyl optionally mono-substituted with fluoro, chloro, methoxy, or trifluoromethyl, or 4-benzyl piperazinyl optionally mono-substituted with fluoro, chloro, methoxy, or trifluoromethyl, and pharmaceutically acceptible quaternary ammonium salts thereof;

(d) $R_3$ is selected from the group consisting of
(1) hydrogen;
(2) alkyl of 1 to about 8 carbon atoms optionally substituted with —OH;
(3) cyclic alkyl of about 3 to about 10 carbon atoms;
(4) alkyl of 1 to about 3 carbon atoms substituted with cyclic alkyl of about 5 to about 8 carbon atoms;
(5) aryl of about 3 to about 10 carbon atoms which is optionally mono-substituted with $Y_1$ or optionally disubstituted with $Y_1$ and $Y_2$;
(6) alkyl of 1 to about 3 carbon atoms substituted on the terminal carbon with aryl of about 4 carbon atoms to about 10 carbon atoms which is optionally mono-substituted with $Y_1$ or optionally disubstituted with $Y_1$ and $Y_2$; and (e) $R_4$ is selected from the group consisting of hydrogen, alkyl of 1 to about 7 carbon atoms optionally substituted with —OH, and alkyl of 1 to about 3 carbon atoms substituted on the terminal carbon atom with aryl of about 4 carbon atoms to about 10 carbon atoms which is optionally mono-substituted with $Y_1$, and pharmaceutically acceptable salts thereof.

Peptidyl arginine aldehydes have been reported to exist in equilibrium structures in aqueous solutions. Bajusz, S., et al. (1990) J. Med. Chem., 33: 1729. These structures, as shown below, include the arginine aldehyde, A, aldehyde hydrate, B, and two amino cyclol forms, C and D. The R group would represent the remainder of a given compound embodied in the present invention. The peptide aldehydes of the present invention include within their definition all the equilibrium forms.

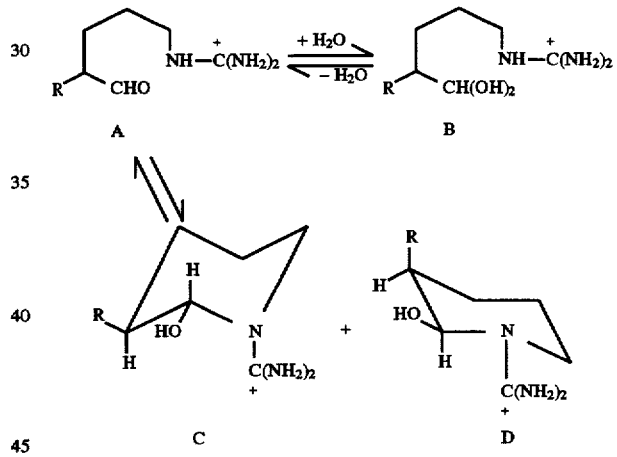

Among other factors, the present invention is based on our finding that the novel compounds of our invention are active as potent inhibitors of factor Xa in vivo and in vitro. In particular, we have found that certain of the preferred compounds of the present invention exhibit advantageous selectivity in that they are very potent inhibitors of factor Xa but are inactive or significantly less active, (several orders of magnitude less) in inhibiting plasmin and are significantly less active in inhibiting thrombin.

In another aspect, the present invention is directed to pharmaceutical compositions comprising a therapeutically effective amount of a compound of the present invention and a pharmaceutically acceptable carrier.

In yet another aspect, the present invention is directed to methods of using the compounds and pharmaceutical compositions of the present invention for the prevention of thrombosis in a mammal suspected of having a condition characterized by abnormal thrombosis, comprising administering to said mammal a therapeutically effective amount of a compound of the present invention or pharmaceutical composition comprising such a compound.

Definitions

In accordance with the present invention and as used herein, the following terms are defined to have the following meanings, unless explicitly stated otherwise:

The term "alkyl" refers to saturated aliphatic groups including straight-chain, branched-chain and cyclic groups. Suitable alkyl groups include cyclohexyl and cyclohexylmethyl. Cyclic groups include polycyclic groups such as adamantyl.

The term "aryl" refers to aromatic groups which have at least one ring having a conjugated pi electron system and includes carbocyclic aryl, heterocyclic aryl and biaryl groups, all of which may be optionally substituted.

The term "carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carbocyclic aryl groups include phenyl and naphthyl. Suitable substituted carbocyclic aryl groups include indene and phenyl substituted by one to two substituents such being advantageously lower alkyl, hydroxy, lower alkoxy, lower alkoxycarbonyl, halogen, trifluoromethyl, nitro, and cyano. Substituted naphthyl refers to 1- or 2-naphthyl substituted by lower alkyl, lower alkoxy, or halogen.

The term "biaryl" refers to phenyl substituted by carbocyclic or heterocyclic aryl as defined herein, ortho, meta or para to the point of attachment of the phenyl ring, advantageously para.

The term "lower" referred to herein in connection with organic radicals or compounds defines such with up to and including 5, preferably up to and including 4 and advantageously one or two carbon atoms. Such groups may be straight chain or branched chain.

The term "alkoxy" refers to —OR wherein R is alkyl.

The term "alkoxycarbonyl" refers to —C(O)OR wherein R is alkyl.

The term "aralkyl" refers to an alkyl group substituted with an aryl group. Suitable aralkyl groups include benzyl, picolyl, and the like, all of which may be optionally substituted.

The term "carboxy" refers to —C(O)OH.

The term "perfluoroalkyl" refers to an alkyl group which has every hydrogen replaced with fluorine.

The term "perfluoroaryl" refers to an aryl group which has every hydrogen replaced with fluorine.

The term "perfluoroaryl alkyl" refers an aralkyl group in which every hydrogen on the aryl moiety is replaced with fluorine.

The term "cycloalkyl" refers to a cyclic alkyl group. Suitable cycloalkyl groups include cyclohexyl.

The term "alkenyl" refers to unsaturated aliphatic groups having at least one double bond. They may be straight-chain, branched-chain or cyclic groups.

The term "aralkenyl" refers to an alkenyl group substituted with an aryl group.

The term "amino acid" refers to both natural, unnatural amino acids in their D and L stereoisomers if their structure allows such stereoisomeric forms, and their analogs. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine and pipecolic acid. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid residue" refers to radicals having the structure: (1) —C(O)—R—NH—, wherein R typically is —CH(R')—, wherein R' is H or a carbon containing substituent; or (2)

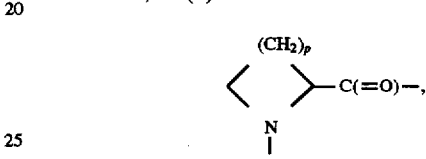

wherein p is 1, 2 or 3 representing the azetidinecarboxylic acid, proline or pipecolic acid residues, respectively.

The term "Arg-al" refers to the residue of L-argininal which has the formula:

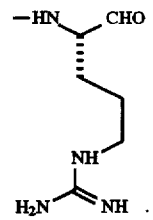

The term "N-alpha-t-butoxycarbonyl-$N^g$-nitro-L-arginine" refers to the compound which has the formula:

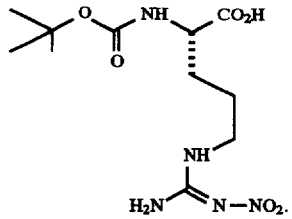

The term "halogen" refers to fluorine, chlorine, bromine and iodine.

The term "heterocyclic hydrocarbyl" refers to groups that are mono and bicyclic rings of 5 to 10 ring atoms. Preferably these rings include 3 to about 9 carbon ring atoms and the remainder of the ring atoms are heteroatoms selected from the group consisting of oxygen, sulfur, and nitrogen. These mono and bicyclic rings include aliphatic and aromatic rings. The aliphatic rings may include double bonds. Heterocyclic hydrocarbyl includes heterocyclic alkyl, heterocyclic aryl, and heterocyclic aralkyl.

The term "hydrocarbyl" refers to groups that contain carbon and hydrogen atoms and includes alkyl, alkenyl, alkynyl, aryl, and aralkyl groups.

The term "heterocyclic alkyl" refers to groups that are mono and bicyclic rings of 5 to 10 ring atoms. Preferably these rings include 3 to about 9 ring carbon atoms and the remainder of the ring atoms are heteroatoms selected from the group consisting of oxygen, sulfur, and nitrogen. These mono and bicyclic rings may include from 0 to 2 double bonds and may be optionally mono-substituted with lower alkyl.

The term "heterocyclic aryl" refers to groups that are mono and bicyclic rings of 5 to 10 ring atoms. Preferably these rings include 2 to about 9 ring carbon atoms and the remainder of the ring atoms are heteroatoms selected from the group consisting of sulfur, oxygen, and nitrogen. The term includes bicyclic rings in which either one or two rings are aromatic. The rings may be optionally mono-substituted with phenyl, fluoro, chloro, trifluoromethyl, hydroxy, methoxy, carboxy, and amino. Suitable heterocyclic aryls include furanyl, thienyl, pyridyl, pyrrolyl, pyrimidyl, pyrazinyl, imidazolyl, and the like.

The term "heterocyclic aralkyl" refers to alkyl groups that are substituted with a heterocyclic aryl group.

The term "quaternary ammonium salt" refers to compounds produced by reaction between a basic nitrogen in an $R_2$ substituent and an alkylhalide, arylhalide, and aralkylhalide. Other reactants with good leaving groups may also be used, such as alkyl trifluoromethanesulfonates, alkyl methanesulfonates, and alkyl p-toluenesulfonates. A quaternary ammonium salt has a positively charged nitrogen in the $R_2$ substituent. Pharmaceutically acceptable counterions include Cl—, Br—, I—, $CF_3C(O)O$— and $CH_3C(O)O$—. The counterion of choice can be made using ion exchange resin coles. $R_2$ groups with basic nitrogens include —$CH_2CH_2CH_2NHC(=NH)NH_2$,

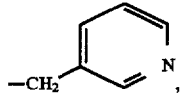

—$(CH_2)_nNH_2$ wherein n is as defined in conjunction with formula I above. In addition, the following $R_2$ groups may contain basic nitrogens: —$CH_2S(O)_2(CH_2)_nC(O)Z_3$, —$CH_2S(O)_2Z_4$, —$(CH_2)_nC(O)NR_5R_6$, and ,

wherein $Z_3$, $Z_4$, $R_5$, $R_6$, and

is as defined in conjunction with formula I above. For example, the following $R_6$ groups contain basic amines: 3-(R)-quinuclidine, 3-(S)-quinuclidine, 3-yl-2-ethyl-4(3H)-quinazolinone, ethyl morpholine, ethyl piperidine, 2-(2-ethyl)pyridine, and [4-(meth-yl)-5-hydroxy-6-methyl-3-pyridine methanol.

The term "terminal carbon" refers to the carbon atom of a straight chain alkyl which is furthest from the parent structure.

In addition, the following abbreviations stand for the following:

"Boc" refers to t-butoxycarbonyl.

"BOP" refers to benzotriazol-1-yl-oxy-tris-(dimethylamino)-phosphonium hexafluorophosphate.

"Brine" refers to an aqueous saturated solution of sodium chloride.

"BzlSO$_2$" refers to benzylsulfonyl.

"DCC" refers to N,N'-dicyclohexylcarbodiimide.

"EDC" refers to 1-ethyl-3-(3-dimethylaminopropyl) carbodiimide hydrochloride salt.

"HATU" refers to O-(7-azabenzotriazol-1-yl)-1,1,3,3-tetramethyluronium hexafluorophosphate.

"HBTU" refers to 2-(1H-benzotriazol-1-yl)-1,1,3,3-tetramethyluronium hexafluorophosphate.

"HCl" refers to hydrochloric acid.

"HOAt" refers to 1-hydroxy-7-azabenzotriazole.

"HOBt" refers to 1-hydroxybenzotriazole monohydrate.

"HPLC" refers to high pressure liquid chromatography.

"LiAlH$_4$" refers to lithium aluminum hydride.

"LiAlH$_2$(OEt)$_2$" refers to lithium aluminum dihydride diethoxide.

"NMM" refers to N-methylmorpholine.

"NaOH" refers to sodium hydroxide.

"THF" refers to tetrahydrofuran.

"TBTU" refers to 2-(1H-benzotriazol-1-yl)-1,1,3,3-tetramethyluronium tetrafluoroborate.

"TLC" refers to thin layer chromatography.

DETAILED DESCRIPTION OF THE INVENTION

1. Preferred Compounds

Figure 1:
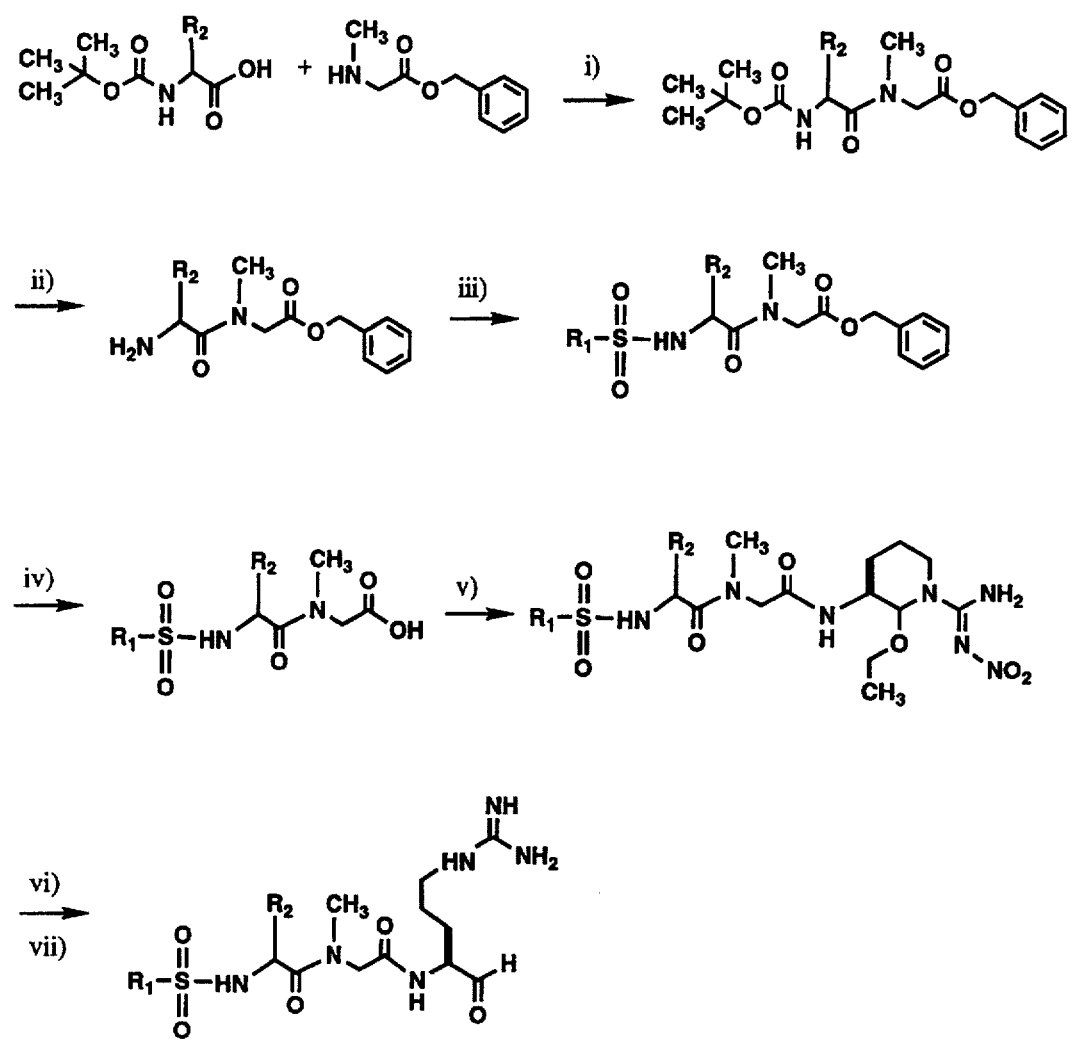
FIG. 1 depicts a preferred general scheme for the preparation of certain compounds of the invention. In this figure, i)–vii) are defined as: i) 1-hydroxybenzotriazole monohydrate, 1-ethyl-3-(3-dimethylaminopropyl) carbodiimide hydrochloride salt, and N-methyl morpholine; ii) 4M hydrochloric acid; iii) $R_1SO_2Cl$ and triethylamine; iv) hydrogen gas and palladium on carbon; v) 2-(1H-benzotriazol-1-yl)-1,1,3,3-tetramethyluroniumhexafluorophosphate, 1-hydroxybenzotriazole monohydrate, $N^g$-nitro-L-argininal ethyl cyclol hydrochloride salt, and N-methyl morpholine; vi) hydrogen gas and palladium on carbon in methanol, acetic acid, and water; vii) hexafluorophosphoric acid or 6M hydrochloric acid in water.

Compounds of the present invention have the formula

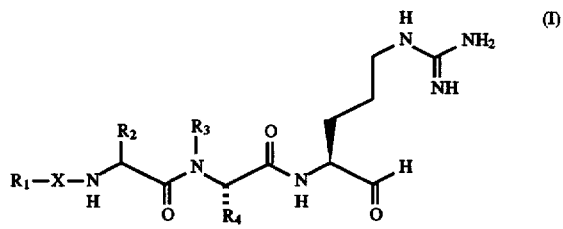

(I)

wherein (a) X is selected from the group consisting of —S(O)$_2$—, —N(R')—S(O)$_2$—, —C(=O)—, —OC(=O)—, —NH—C(=O)—, and a direct link, wherein R' is hydrogen, or alkyl of 1 to about 4 carbon atoms;

(b) $R_1$ is selected from the group consisting of:
(1) alkyl of 1 to about 12 carbon atoms,
(2) alkyl of 1 to about 3 carbon atoms substituted with cyclic alkyl of about 5 to about 8 carbon atoms,
(3) alkenyl of about 3 to about 6 carbon atoms which is optionally substituted with cyclic alkyl of about 5 to about 8 carbon atoms,
(4) aryl of about 4 to about 14 carbon atoms which is optionally mono-substituted with $Y_1$ or optionally di-substituted with $Y_1$ and $Y_2$,
(5) aralkyl of about 5 to about 15 carbon atoms which is optionally mono-substituted in the aryl ring with $Y_1$ or optionally di-substituted in the aryl ring with $Y_1$ and $Y_2$,
(6) aralkenyl of about 6 to about 15 carbon atoms which is optionally mono-substituted in the aryl ring with $Y_1$ or optionally di-substituted in the aryl ring with $Y_1$ and $Y_2$,

(7)

(8)

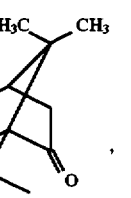

(9)

(10)

(11) perfluoroalkyl of 1 to about 12 carbon atoms,
(12) perfluoroaryl of about 6 to about 14 carbon atoms,
(13) perfluoroaryl alkyl of about 7 to about 15 carbon atoms, and
(14)

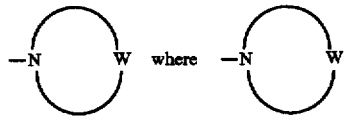

where is a 5 to 7 member heterocycle of 3 to 6 ring carbon atoms, where W is —CH$_2$—, —O—, —S(=O)—, —S(O)$_2$— or —S—, where
$Y_1$ and $Y_2$ are independently selected from halogen, —CF$_3$, —CF$_2$CF$_3$, —CH(CF$_3$)$_2$, —C(OH)(CF$_3$)$_2$, cyano, nitro, —C(O)OH, —C(O)OZ$_1$, —Z$_1$, —OZ$_1$, —OH, —NH$_2$, —NHZ$_1$, —NZ$_1$Z$_2$, —P(O)$_3$H$_2$, —P(O)$_3$(Z$_1$)$_2$, tetrazolyl, —S(O)$_3$H and —S(O)$_m$Z$_1$ wherein m is 0, 1 or 2, Z$_1$ and Z$_2$ are independently selected from the group consisting of alkyl of 1 to about 6 carbon atoms, aryl of about 3 to about 14 carbon atoms and aralkyl of about 4 to about 15 carbon atoms, with the provisos that:
(1) when $Y_1$ is halogen, then $Y_2$ is hydrogen or halogen;
(2) when $Y_1$ is —C(O)OH, then $Y_2$ is hydrogen, —OH or —C(O)OH;
(3) when $Y_1$ is —C(O)OZ$_1$, then $Y_2$ is hydrogen, —OH or —C(O)OZ$_1$;
(4) when $Y_1$ is —Z$_1$, then $Y_2$ is hydrogen, —OH or —Z$_1$;
(5) when $Y_1$ is —CF$_3$, then $Y_2$ is hydrogen, —OH or —CF$_3$;

(6) when $Y_1$ is —$OZ_1$, then $Y_2$ is hydrogen, —OH or —$OZ_1$;

(7) when $Y_1$ is —OH, then $Y_2$ is hydrogen, —OH, —C(O)OH, C(O)$OZ_1$, —$CF_3$, —S(O)$_3$H, or —S(O)$_m Z_1$; and (8) when $Y_1$ is cyano, nitro, —P(O)$_3 H_2$, —P(O)$_3(Z_1)_2$, —$NH_2$, —$NHZ_1$, —$NZ_1 Z_2$, or tetrazolyl, then $Y_2$ is hydrogen;

(c) $R_2$ is selected from the group consisting of hydrogen, —$CH_2 CH_2 CH_2$NHC(=NH)$NH_2$, —$CH_2 CH_2$S(O)$_2 CH_3$, —$CH_2$C(O)OH, —$CH_2$C(O)O$CH_3$, —$CH_2$S(O)$_2$(CH$_2$)$_n$C(O)$Z_3$,

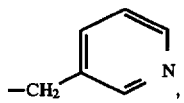

—$CH_2$S(O)$_2 Z_4$, —(CH$_2$)$_n NH_2$, —(CH$_2$)$_n$C(O)NR$_5 R_6$, and

wherein n=2, 3, 4, 5, or 6, $Z_3$ is —OH, —$OCH_3$, or —$NR_5 R_6$, $Z_4$ is alkyl of 1 to about 4 carbon atoms, aryl of about 6 to about 14 carbon atoms, or aralkyl of about 7 to 16 carbon atoms, $R_5$ is hydrogen or methyl, $R_6$ is a cyclic alkyl of 1 to about 10 carbon atoms, an aralkyl of about 5 to about 15 carbon atoms optionally monosubstituted with $Y_1$, or heterocyclic hydrocarbyl of 5 to 10 ring atoms with 3 to about 9 ring carbon atoms and the remainder of the ring atoms are heteroatoms selected from oxygen, sulfur and nitrogen, optionally subustituted, wherein $Y_1$ is as defined above,

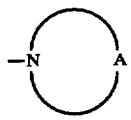

is 6,7-dimethoxy-1,2,3,4-tetrahydroisoquinolinyl, 4-hydroxy piperidyl, 4-keto piperidyl, N-morpholino, 3,4-methylenedioxybenzyl piperazinyl, 4-phenyl piperazinyl optionally mono-substituted with fluoro, chloro, methoxy, or trifluoromethyl, or 4-benzyl piperazinyl optionally monosubstituted with fluoro, chloro, methoxy, or trifluoromethyl, and pharmaceutically acceptable quaternary ammonium salts thereof;

(d) $R_3$ is selected from the group consisting of
(1) hydrogen;
(2) alkyl of 1 to about 8 carbon atoms optionally substituted with —OH;
(3) cyclic alkyl of about 3 to about 10 carbon atoms;
(4) alkyl of 1 to about 3 carbon atoms substituted with cyclic alkyl of about 5 to about 8 carbon atoms;
(5) aryl of about 3 to about 10 carbon atoms which is optionally mono-substituted with $Y_1$ or optionally disubstituted with $Y_1$ and $Y_2$;

(6) alkyl of 1 to about 3 carbon atoms substituted on the terminal carbon with aryl of about 4 carbon atoms to about 10 carbon atoms which is optionally monosubstituted with $Y_1$ or optionally disubstituted with $Y_1$ and $Y_2$; and (e) $R_4$ is selected from the group consisting of hydrogen, alkyl of 1 to about 7 carbon atoms optionally substituted with —OH, and alkyl of 1 to about 3 carbon atoms substituted on the terminal carbon atom with aryl of about 4 carbon atoms to about 10 carbon atoms which is optionally mono-substituted with $Y_1$, and pharmaceutically acceptable salts thereof.

Preferred X groups include —$SO_2$—, —NH—S(O)$_2$—, and —N(R')—S(O)$_2$. Especially preferred X groups include —$SO_2$.

Preferred $R_1$ groups include alkyl, aralkyl, and aryl groups. Suitable aralkyl and aryl groups include substituted or unsubstituted benzyl and naphthyl, respectively. Preferred substitutions include, —C(O)OH, —C(O)$OZ_1$, —S(O)$_m Z_1$, and —$CF_3$. Meta and ortho substitution is preferred. Ortho substitution is particularly preferred. Especially preferred $R_1$ groups include aralkyl groups. Particularly preferred $R_1$ groups include substituted or unsubstituted benzyl groups. Cyclohexyl and cyclohexylmethyl are especially preferred $R_1$ groups.

Preferred $R_2$ groups include —$CH_2 CH_2 CH_2$NHC(=NH)$NH_2$, —$CH_2 CH_2$S(O)$_2 CH_3$, —$CH_2$S(O)$_2$(CH$_2$)$_n$C(O)$Z_3$, —(CH$_2$)$_n$C(O)NR$_5 R_6$, and

Particularly preferred are —$CH_2 CH_2 CH_2$NHC(=NH)$NH_2$, —$CH_2 CH_2$S(O)$_2 CH_3$, and —(CH$_2$)$_n$C(O)NR$_5 R_6$. Especially preferred is —$CH_2 CH_2 CH_2$NHC(=NH)$NH_2$. Preferred $R_5$ groups include hydrogen. Preferred $R_6$ groups include 3-(R)-quinuclidine, 3-(S)-quinuclidine, 4-trifluoromethyl-7-yl-coumarin, 4-methyl-7-yl-coumarin, 7-yl-coumarin, 3-yl-2-ethyl-4(3H)-quinazolinone, 2-yl-benzothiazole, 3-yl-benzoic acid, 3-yl-4-hydroxybenzoic acid, 4-hydroxy-1-methyl-6-phenyl-3-yl-2(1H)-pyridone, and 1-adamantyl, or ethyl morpholine, ethyl piperidine, 2-(2-ethyl)pyridine, 4-hydroxyphenethyl, (R)-alpha-methylbenzyl, (S)-alpha-methylbenzyl, [4-(methyl)-5-hydroxy-6-methyl-3-pyridine methanol, [(1R,2S)-(N-methyl-N-(1-ethyl))benzyl alcohol], [(1S,2R)-(N-methyl-N-(1-ethyl))benzyl alcohol], [(1R,2R)-(N-methyl-N-(1-ethyl)) benzyl alcohol], [(1S,2S)-(N-methyl-N-(1-ethyl))benzyl alcohol], and [4-(methyl)-5-hydroxy-6-methyl-3-pyridine methanol].

A preferred group of quaternary ammonium salts on the $R_2$ group are those alkylated with alkyl of 1 to about 10 carbon atoms. Particularly preferred straight chain quaternary ammonium salts are those with methyl, ethyl, propyl and butyl. Preferred branched alkyl quaternary ammonium salts include isopropyl, isobutyl, isopentyl, and isoamyl. Preferred cyclic quaternary ammonium salts include cyclohexyl, cyclopentyl, and cyclohexylmethyl. Another preferred group of quaternary ammonium salts are those alkylated with aralkyl of 7 to about 15 carbon atoms. Particularly preferred aralkyl groups for quaternary ammonium salts include benzyl and phenethyl. Another preferred group of quaternary ammonium salts are those alkylated with aryl of 6 to about 14 carbon atoms, optionally substituted.

Preferred counterions to the quaternary ammonium salts include chlorine, bromine, iodine, acetate, and trifluoroacetate.

Preferred $R_3$ groups include alkyl groups of 1 to about 7 carbon atoms optionally substituted with —OH on a terminal carbon atom. Other preferred $R_3$ groups include methyl, cyclohexylmethyl, phenyl, and benzyl. Particularly preferred $R_3$ groups are methyl, and cyclohexyl.

Preferred $R_4$ groups include hydrogen and alkyl groups of 1 to about 7 carbon atoms optionally substituted with —OH on a terminal carbon atom. Particularly preferred is hydrogen.

According to a particularly preferred aspect, provided are compounds of formula I wherein X is —S(O)$_2$—, $R_1$ is substituted or unsubstituted aralkyl, and $R_2$ is —CH$_2$CH$_2$CH$_2$NHC(=NH)NH$_2$, $R_3$ is methyl, and $R_4$ is hydrogen.

Another particularly preferred aspect are compounds of formula I wherein X is —S(O)$_2$—, $R_1$ is substituted or unsubstituted aralkyl, and $R_2$ is —CH$_2$CH$_2$NHC(=NH) NH$_2$, $R_3$ is cyclohexyl, and $R_4$ is hydrogen. A very preferred aspect is directed to such compounds where $R_1$ is substituted or unsubstituted benzyl.

Preferred compounds include D-camphorsulfonyl aspartyl sarcosine arginine aldehyde, D-camphorsulfonyl cysteinesulfone-acetic acid sarcosine-arginine aldehyde, D-camphorsulfonyl-L-methionine sulfone sarcosine-arginine aldehyde, and benzylsulfonyl-D-arginine-sarcosine-arginine aldehyde.

According to another aspect, the present invention is directed to salts of the compounds of formula (I). "Salt" includes within its definition, salts of the compounds of the present invention derived from the combination of such compounds and an organic or inorganic acid. In practice, the use of the salt form amounts to use of the base form. The compounds of the present invention are useful in both free base and salt form, with both forms being considered as being within the scope of the present invention. These salts include acid addition salts, for example, salts of hydrochloric acid, hydrobromic acid, acetic acid, benzene sulfonic acid and other suitable acid addition salts. These salts include salts formed from compounds containing quaternary ammonium salts.

2. Preparation of Preferred Compounds

The compounds of the present invention may be prepared by the preferred reaction schemes depicted in FIGS. 1, 3, 4, and 5. Examples 1 through 4 provide the details of a preferred method of making the commonly utilized intermediate, $N^g$-nitro-L-argininal ethyl cyclol.

As shown in FIG. 1, various Boc protected amino acids are coupled to sarcosine benzyl ester. Other N-alkylated amino acids may be used. The Boc group is removed with hydrochloric acid. The hydrochloride salt of the terminal free amine is reacted with triethylamine, and $R_1SO_2Cl$ in acetonitrile to give the sulfonamide, which is then hydrogenated with hydrogen gas and palladium on carbon in a Parr Shaker to remove the benzyl ester protecting group. The free acid is coupled to $N^g$-nitro-L-argininal ethyl cyclol hydrochloride salt (prepared as described in Examples 1 through 4) by carbodiimide coupling.

The $N^g$-nitro group of the adduct is then removed by hydrogenation with hydrogen gas and palladium on carbon in ethanol, water, and acetic acid. Then the compound is reacted with 3N hydrochloric acid or hexafluorophosphoric acid to provide the argininal compound of the invention.

The preferred means of chemically coupling (as for example, the first step in FIG. 1) include formation of a peptide bond by using conventional coupling reagents known in the art. See Bodanszky, N., Peptide Chemistry, pp. 55–73, Springer-Verlag, New York (1988) and references cited therein. The chemical coupling may be either by means of one-step or two-step coupling. In one-step coupling, the two coupling partners are coupled directly. Preferred coupling reagents for one-step coupling include N,N'-dicyclohexylcarbodiimide with 1-hydroxybenzotriazole monohydrate, 1-ethyl-3-(3-dimethylaminopropyl) carbodiimide with 1-hydroxybenzotriazole monohydrate, benzotriazol-1-yl-oxy-tris(dimethylamino)phosphonium hexafluorophosphate, 2-(1H-benzotriazol-1-yl)-1,1,3,3-tetramethyluronium hexafluorophosphate or 2-(1H-benzotriazol-1-yl)-1,1,3,3-tetramethyluronium tetrafluoroborate. In two-step coupling, an activated ester or anhydride of the C-terminal carboxy group of one coupling partner is formed prior to its coupling to the other coupling partner.

For compounds of the present invention containing alkenyl or aryl moieties substituted with halogen, cyano, nitro, or —S—$Z_1$, it is preferred to avoid the use of hydrogen gas with palladium on carbon. Instead, it is preferred to use boron tris(trifluoroacetate), B(OCOCF$_3$)$_3$, to cleave the $N^g$-nitro protecting the arginine group. The reagent is prepared by the reaction of BBr$_3$ and CF$_3$COOH in dichloromethane at 0° C. The reagent is also commercially available. Generally, the $N^g$-nitro compound is treated with boron tris(trifluoroacetate) in trifluoroacetic acid at 0° C. Fieser, M. and Fieser, L. F., Reagents for Organic Synthesis, p. 46, John Wiley & Sons, New York (1974); Pless, J., and Bauer, W. (1973) Angew. Chem., Internat. Ed., 12, 147.

An even more preferred method is to use the di-N-t-butoxycarbonyl protecting group for the L-argininal moiety for groups incompatible with hydrogenation with palladium on carbon. For example, alpha-N-t-benzyloxycarbonyl-omega, omega'-di-N-t-butoxycarbonylarginine is dissolved in acetonitrile and treated with hydroxybenzotriazole and 1-ethyl-3-(3-dimethylamino-propyl)carbodiimide hydrochloric acid salt to form alpha-N-benzyloxycarbonyl-omega, omega'-di-N-t-butoxycarbonyl-L-arginine lactam. The lactam is opened by treatment with LiAlH$_4$ in tetrahydrofuran at –70° C. to provide alpha-N-benzyloxycarbonyl-omega, omega'-di-N-t-butoxycarbonyl-L-argininal. This aldehyde is protected as the diethyl acetal by treatment with ethanol and hydrochloric acid. The N-benzyloxycarbonyl protecting group is removed by treatment with hydrogen gas and palladium on carbon to give omega, omega'-di-N-t-butoxycarbonyl-L-argininal diethyl acetal, hydrochloric acid salt. This protected L-argininal moiety can then be coupled to a desired carboxylic acid by treatment with N-hydroxybenzotriazole and 1-ethyl-3-(3-dimethylamino-propyl)carbodiimide hydrochloric acid salt. The diethyl acetal and the di-BOC protecting groups are removed by treatment with hexafluorophosphonic acid in acetonitrile at 0° C. The reaction is quenched with 2.5M aqueous sodium acetate until pH 4 is reached. The mixture is filtered through a 2 micron filter. Preparative HPLC using 0.1% CF$_3$COOH in 10–40% aqueous acetonitrile provides the trifluoroacetate salt of the desired substituted L-argininal compound.

Figure 3:
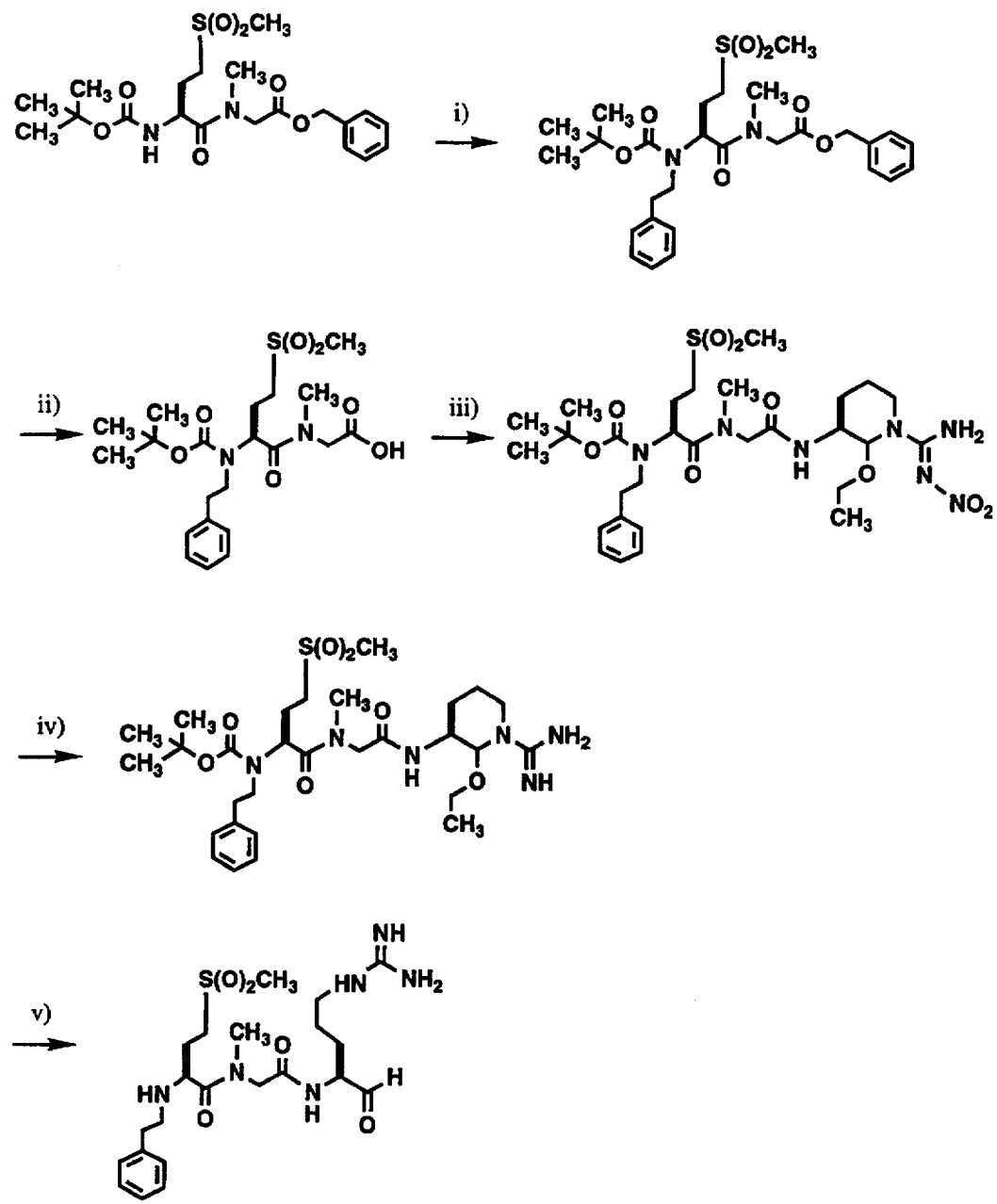
FIG. 3 depicts a preferred general scheme for preparing compound where X is a direct link. In this figure, i)–v) are defined as: i) (2-iodoethyl)benzene and sodium hydride; ii) hydrogen gas and palladium on carbon; iii) $N^g$-nitro-L-argininal ethyl cyclol hydrochloride salt, 1-hydroxybenzotriazole monohydrate, 1-ethyl-3-(3-dimethylaminopropyl)carbodiimide hydrochloride salt, and N-methyl morpholine; iv) hydrogen gas and palladium on carbon; and v) hexafluorophosphoric acid or 6M hydrochloric acid in water.

In FIG. 3, the Boc protected methionine sulfone sarcosine benzyl ester, prepared in Example 74a, is N-alkylated with (2-iodoethyl) benzene. Various N-alkylating agents can be used. The benzyl ester protecting group is removed by treatment with hydrogen gas and palladium on carbon. The resulting free acid is coupled to the compound of Example 4 by treatment with 1-ethyl-3-(-dimethylaminopropyl) carbodiimide, N-hydroxybenzotriazole, and N-methyl morpholine. The $N^g$-nitro group is removed by treatment with hydrogen gas, palladium on carbon in methanol, acetic acid and water mixture. The cyclic arginine ethylaminal is opened by treatment with hexafluorophosphoric acid in water to give the final product. FIG. 3 guides the synthesis of compounds where X is a direct link. Examples 74a through 78 provide the synthesis described.

Figure 4:
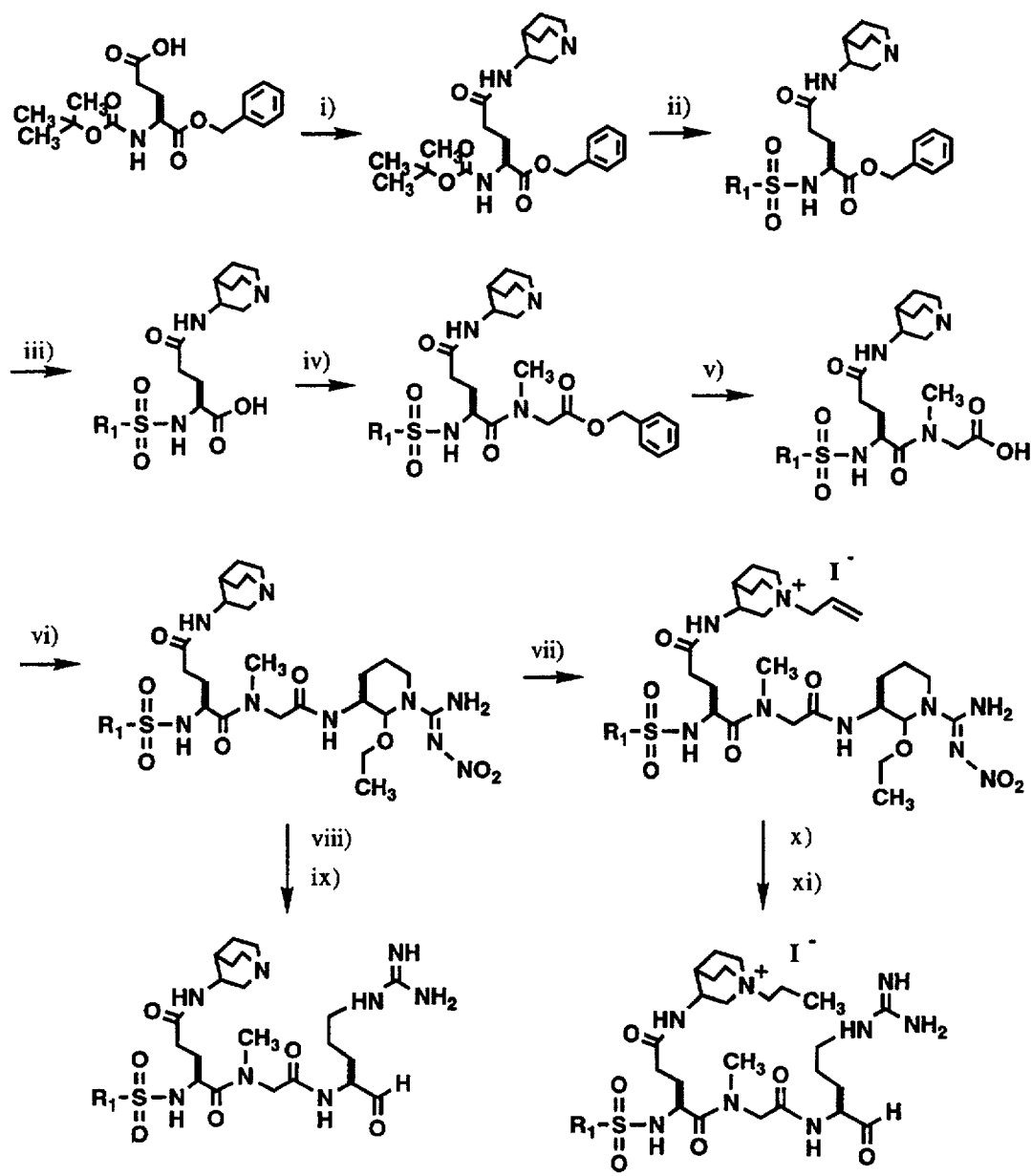
FIG. 4 depicts a preferred general reaction scheme for the preparation of certain quaternary ammonium salts at the $R_2$ position. In this figure, i)–xi) are defined as: i) 3-(R)-aminoquinuclidine dihydrochloride, and N,N-diisopropylamine; ii) 4M hydrochloric acid and then triethylamine and $R_1SO_2Cl$; iii) hydrogen gas and palladium on carbon; iv) 1-ethyl-3-(3-dimethylaminopropyl)carbodiimide hydrochloride salt, 1-hydroxybenzotriazole monohydrate, sarcosine benzyl ester p-toluenesulfonate salt, and N-methyl morpholine; v) hydrogen gas and palladium on carbon; 1-hydroxybenzotriazole monohydrate, 2-(1H-benzotriazol-1-yl)-1,1,3,3-tetramethyluronium hexafluorophosphate, $N^g$-nitro-L-argininal ethyl cyclol hydrochloride salt, and N-methyl morpholine; vii) allyl iodide; viii) hydrogen gas and palladium on carbon in acetic acid, methanol, and water; ix) hexafluorophosphoric acid in water; x) hydrogen gas and palladium on carbon in acetic acid, methanol, and water; and xi) hexafluorophosphoric acid or 6M hydrochloric acid in water.

FIG. 4 illustrates a preferred method of synthesizing compounds with an N-alkylated $R_2$ group. "N-alkylated" encompasses N-alkylated, N-arylated, and N-aralkylated quaternary ammonium salts. Examples 79 through 89 provide the details of this scheme.

The Boc protected glumatic acid benzyl ester is coupled to 3-(R)-aminoquinuclidine dihydrochloride using standard procedures. Various amines could be used. Strong acid removes the Boc protecting group. The amine is then reacted with triethylamine and benzylsulfonyl chloride. The benzyl ester protecting group is removed by catalytic hydrogenation. The free acid is then coupled to the compound of Example 4 using standard coupling reagents. The basic amine of the $R_2$ group is then reacted with allyliodide. The $N^g$-nitro group is removed and the allyl group reduced by treatment with hydrogen gas and palladium on carbon. The cyclic arginine ethylaminal is opened with hexafluorophosphoric acid or 6M hydrochloric acid in water to give the final product.

Figure 5:
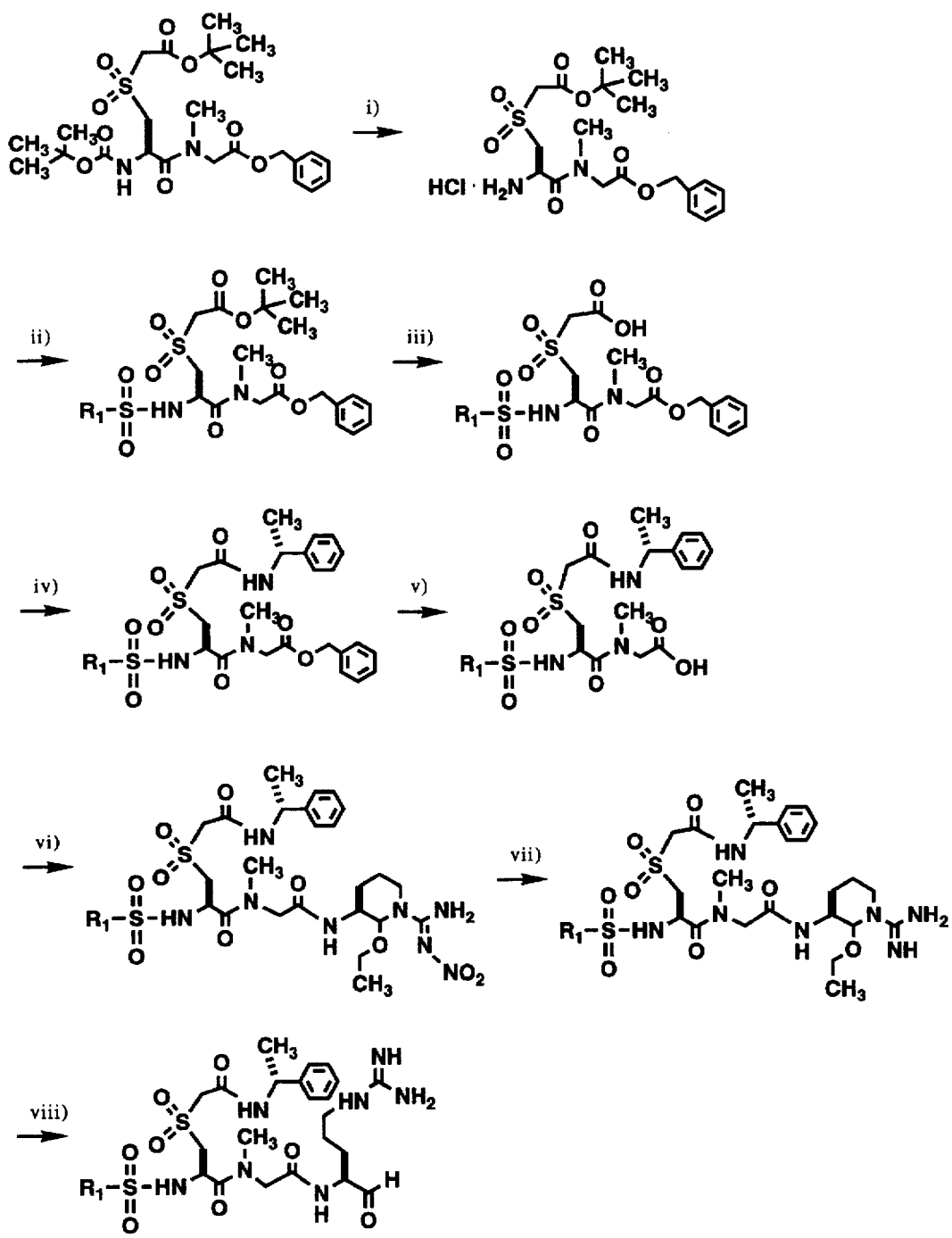
FIG. 5 depicts a preferred reaction scheme for the preparation of substituted cysteines in the $R_2$ position. In this figure, i)–viii) are defined as: i) 5.7M hydrochloric acid; ii) $R_1SO_2Cl$ and pyridine; iii) trifluoroacetic acid; iv) 1-ethyl-3(3-dimethylaminopropyl)carbodiimide hydrochloride salt, 1-hydroxybenzotriazole monohydrate, and (R)-alphamethylbenzylamine; v) hydrogen gas and palladium on carbon; vi) 1-ethyl-3-(3-dimethylaminopropyl)carbodiimide hydrochloride salt, 1-hydroxybenzotriazole monohydrate, $N^g$-nitro-L-argininal ethyl cyclol hydrochloride salt and N-methyl morpholine; vii) hydrogen gas and palladium on carbon in acetic acid, methanol and water; and viii) hexafluorophosphoric acid or 6M hydrochloric acid in water.

FIG. 5 illustrates a preferred reaction scheme for the preparation of N-benzylsulfonyl-L-cysteine sulfone-S-((R)-alphamethylbenzylcarboxyamide)-sarcosine argininal. Examples 90 through 96 illustrate the reaction scheme. The Boc group of butyl acetate cysteinesulfone sarcosine-O-benzyl ester, prepared according to Examples 36 through 39 is removed by treatment with anhydrous hydrochloric acid. The terminal amine is reacted with an amine base and $R_1SO_2Cl$ to provide the sulfonamide. The t-butyl ester is reacted with trifluoroacetic acid to form the carboxylic acid. The acid is then coupled to (R)-alphamethyl benzylamine using 1-ethyl-3-(3-dimethylaminopropyl)carbodiimide hydrochloride salt and 1-hydroxybenzotriazole. The resulting adduct is then treated with hydrogen gas and palladium on carbon to remove the benzyl ester protecting group. The resulting acid is coupled to the compound of Example 4 using standard coupling techniques. The $N^g$-nitro group is removed with catalytic hydrogenation and then the argininal ethyl cyclol aminal is opened with hexafluorophosphoric acid or 6M hydrochloric acid in water to give the argininal product.

3. Selection of Preferred Compounds

The compounds of the present invention are screened for their ability to inhibit thrombin, plasmin, recombinant tissue plasminogen activator (rt-PA), activated protein C (aPC), chymotrypsin, and trypsin as set forth below. Certain of the preferred compounds are distinguished by their ability to inhibit factor Xa, while not substantially inhibiting thrombin, plasmin, t-PA, aPC, chymotrypsin, and trypsin. With respect to factor Xa and the other enzymes and as used herein, the term "not substantially inhibiting" means that the $IC_{50}$ (or $K_i$) for thrombin, plasmin, t-PA, aPC, chymotrypsin, and trypsin for a given compound is greater than or equal to its $IC_{50}$ (or $K_i$, respectively) for factor Xa.

The compounds of the present invention are dissolved in buffer to give solutions containing concentrations such that assay concentrations range from 0 to 100 micromolar. In the assays for factor Xa, thrombin, plasmin, t-PA, aPC, chymotrypsin, and trypsin, a chromogenic synthetic substrate is added to a solution containing test compound and the enzyme of interest and the residual catalytic activity of that enzyme is determined spectrophometrically. The $IC_{50}$ of a compound of the present invention is determined from the rate of substrate turnover caused by the specific enzyme being measured. $IC_{50}$ is that concentration of test compound giving 50% inhibition of the rate of substrate turnover. Likewise, the $K_i$ of a compound of the present invention is determined from the rate of substrate turnover caused by the specific enzyme being measured at various enzyme concentrations. $K_i$ is that concentration of test compound giving 50% inhibition of the rate of substrate turnover. Examples A and B provide an exemplar of the in vitro assays used to select the compounds of the present invention.

Certain of the preferred compounds of the present invention have a $K_i$ of about 0.001 to about 200 nM in the factor Xa assay. Especially preferred compounds have a $K_i$ of about 0.001 to about 50 nM. The more especially preferred compounds have a $K_i$ of about 0.001 to about 10 nM.

Certain of the preferred compounds of the present invention have a $IC_{50}$ for thrombin, plasmin, t-PA, aPC, chymotrypsin, and trypsin which is at least 10 times greater than its $IC_{50}$ for factor Xa. Especially preferred compounds have an $IC_{50}$ for thrombin, plasmin, rt-PA, aPC, chymotrypsin, and trypsin which is about 20 to about 100,000 times greater than its $IC_{50}$ for thrombin. More especially preferred compounds have an $IC_{50}$ for thrombin, plasmin, rt-PA, aPC, chymotrypsin, and trypsin which is about 100 to about 1,000,000 times greater than its $IC_{50}$ for factor Xa. In the event that a compound of the present invention has an $IC_{50}$ with respect to thrombin, plasmin, rt-PA, aPC, chymotrypsin, or trypsin which is greater than the highest concentration of compound tested, the $IC_{50}$ is taken to be that highest concentration of compound.

4. Pharmaceutical Compositions

In another aspect, the present invention encompasses pharmaceutical compositions prepared for storage or administration which comprise a therapeutically effective amount of a compound of the present invention in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

The therapeutically effective amount of a compound of the present invention can range broadly depending upon the desired effects and the therapeutic indication. Typically, dosages will be between about 0.01 mg/kg and 100 mg/kg body weight, preferably between about 0.01 and 10 mg/kg, body weight.

Pharmaceutically acceptable carriers for therapeutic use are well known in the pharmaceutical art, and are described, for example, in *Remington's Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The pharmaceutical compositions of the present invention may be formulated and used as tablets, capsules or elixirs for oral administration; suppositories for rectal administration; sterile solutions and suspensions for injectable administration; and the like. The dose and method of administration can be tailored to achieve optimal efficacy but will depend on such factors as weight, diet, concurrent medication and other factors which those skilled in the medical arts will recognize.

When administration is to be parenteral, such as intravenous on a daily basis, injectable pharmaceutical compositions can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

5. Utility and Methods

Compounds of the present invention when made and selected as disclosed are useful as potent inhibitors of factor Xa in vitro and in vivo. As such, these compounds are useful as in vitro diagnostic reagents to prevent the clotting of blood and as in vivo pharmaceutical agents to prevent thrombosis in mammals suspected of having a condition characterized by abnormal thrombosis.

The compounds of the present invention are useful as in vitro diagnostic reagents for inhibiting clotting in blood drawing tubes. The use of stoppered test tubes having a vacuum therein as a means to draw blood obtained by venipuncture into the tube is well known in the medical arts. Kasten, B. L., "Specimen Collection", *Laboratory Test Handbook*, 2nd Edition, Lexi-Comp Inc., Cleveland pp. 16–17 (Edits. Jacobs, D. S. et al. 1990). Such vacuum tubes may be free of clot-inhibiting additives, in which case, they are useful for the isolation of mammalian serum from the blood. They may alternatively contain clot-inhibiting additives (such as heparin salts, EDTA salts, citrate salts or oxalate salts), in which case, they are useful for the isolation of mammalian plasma from the blood. The compounds of the present invention are potent inhibitors of factor Xa, and as such, can be incorporated into blood collection tubes to prevent clotting of the mammalian blood drawn into them.

The compounds of the present invention are used alone, in combination of other compounds of the present invention, or in combination with other known inhibitors of clotting, in the blood collection tubes. The amount to be added to such tubes is that amount sufficient to inhibit the formation of a clot when mammalian blood is drawn into the tube. The addition of the compounds to such tubes may be accomplished by methods well known in the art, such as by introduction of a liquid composition thereof, as a solid composition thereof, or liquid composition which is lyophilized to a solid. The compounds of the present invention are added to blood collection tubes in such amounts that, when combined with 2 to 10 mL of mammalian blood, the concentration of such compounds will be sufficient to inhibit clot formation. Typically, the required concentration will be about 1 to 10,000 nM, with 10 to 1000 nM being preferred.

The compounds of the present invention are useful as pharmaceutical agents for preventing thrombosis in a mammal suspected of having a condition characterized by abnormal thrombosis.

Conditions characterized by abnormal thrombosis are well known in the medical arts and include those involving the arterial and venous vasculature of mammals. With respect to the coronary arterial vasculature, abnormal thrombosis (thrombus formation) characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombosis characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombosis further characterizes disseminated intravascular coagulopathy which commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The present invention includes methods for preventing a condition in a mammal suspected of having a condition characterized by abnormal thrombosis, comprising administering to said mammal a therapeutically effective amount of a compound or a pharmaceutical composition of the present invention.

The compounds or pharmaceutical compositions of the present invention are administered in vivo, ordinarily in a mammal, preferably in a human. In employing them in vivo, the compounds or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets capsules or elixirs taken on a daily basis.

In practicing the methods of the present invention, the compounds or pharmaceutical compositions of the present invention are administered alone or in combination with one another, or in combination with other therapeutic or in vivo diagnostic agents.

As is apparent to one skilled in the medical art, a therapeutically effective amount of the compounds or pharmaceutical compositions of the present invention will vary depending upon the age, weight and mammalian species treated, the particular compounds employed, the particular mode of administration and the desired effects and the therapeutic indication. Because these factors and their relationship to determining this amount are well known in the medical arts, the determination of therapeutically effective dosage levels, the amount necessary to achieve the desired result of preventing thrombosis, will be within the ambit of one skilled in these arts. Typically, administration of the compounds or pharmaceutical compositions of the present invention is commenced at lower dosage levels, with dosage levels being increased until the desired effect of preventing in vivo thrombosis is achieved which would define a therapeutically effective amount. For the compounds of the present invention, alone or as part of a pharmaceutical composition, such doses are between about 0.01 mg/kg and 100 mg/kg body weight, preferably between about 0.01 and 10 mg/kg, body weight.

To assist in understanding, the present invention will now be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Preparation of N-alpha-t-butoxycarbonyl-N$^g$-nitro-L-arginine lactam.

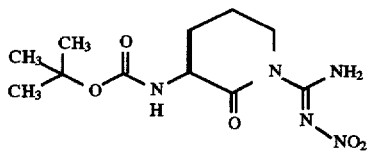

N-alpha-t-butoxycarbonyl-N$^g$-nitroarginine (2.00 g, 6.3 mmole) was dissolved in tetrahydrofuran (100 mL) by heating the solution to 50° C. The solution was allowed to cool to room temperature. N-methylpiperidine (0.84 mL, 6.9 mmole) was added, and the solution was cooled in an ice bath. Isobutylchloroformate (0.83 mL, 6.3 mmole) was added, and the reaction mixture was stirred at 0° C. for 6 hours. The reaction mixture was stirred for 18 hours while the ice in the dewar was allowed to melt overnight. The solvent was removed under vacuum. The crude product was dissolved in 20% ethyl acetate/dichloromethane (10 mL), and was purified by flash chromatography through a 3×5 cm column of silica gel using 20% ethyl acetate/dichloromethane as eluent. 125 mL of eluent was collected. The solvent was removed under vacuum to afford 1.39 g (74% crude yield) of the title compound as a white foam. $R_f$=0.44 (silica gel, 95:5, dichloromethane:isopropanol). Isobutanol was present as an impurity. This compound may be further purified by recrystallization from dichloromethane/hexanes or ethanol/water.

Example 2

Preparation of N-alpha-t-butoxycarbonyl-N$^g$-nitro-L-argininal.

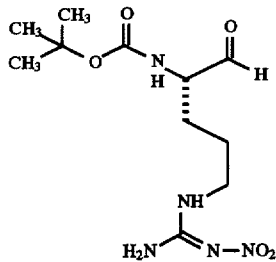

(a) Procedure 1.

To a stirred solution of LiAlH$_4$ in tetrahydrofuran (3.8 mL of a 1.0M solution, 3.8 mmole), cooled in an ice bath, was added dropwise ethyl acetate (0.43 mL, 3.8 mmole) in tetrahydrofuran (5 mL). The solution was stirred for 30 minutes at 0° C. to preform LiAlH$_2$(OEt)$_2$.

The solution of this LiAlH$_2$(OEt)$_2$ was added dropwise to a stirred solution of compound of Example 1 (0.92 g, 3.1 mmole) in tetrahydrofuran (5 mL). After 30 minutes, the reaction is quenched with 1.0N aqueous hydrochloric acid/tetrahydrofuran (2 mL of a 1:1 mixture). 1.0N aqueous hydrochloric acid (20 mL) was added, and the solution was extracted three times with ethyl acetate (20 mL each). The combined organic layers were washed with water (5 mL), saturated sodium bicarbonate (5 mL) and twice with brine (2×5 mL), dried over anhydrous magnesium sulfate, filtered and the solvent was removed under vacuum to give 0.94 g (100% yield) of the title compound as an off-white solid.

(b) Procedure 2.

Alternatively, the title compound was made by the procedures which follow.

A 12 liter four-necked round bottom flask equipped with an overhead stirring apparatus was flame dried under a strong stream of nitrogen. After the flask had cooled, 120.0 g of N-alpha-t-butoxycarbonyl-N$^g$-nitro-L-arginine (376 mmole, 1 equivalent) was added under a blanket of nitrogen followed by the addition of 6 liters of anhydrous tetrahydrofuran (Aldrich sure-seal) via cannula. The flask was then fitted with a thermometer and the resulting suspension was warmed to 50° C. with a heat gun while stirring. The reaction mixture was cooled to 5° C. with an ice bath and further cooled to −5° C. with an ice/acetone bath.

During the time it took for this solution to reach −5° C., 36.66 g of N,O-dimethylhydroxylamine hydrochloride (376 mmole, 1.0 equivalent) was weighed out in a 500 mL flask and suspended in 300 mL of dichloromethane. This suspension was sparged with nitrogen for 5 minutes, cooled to 0° C. and 46 mL of N-methylpiperidine (1.0 equivalent) was added via syringe under nitrogen. The mixture was sonicated briefly to insure complete dissolution/free base formation and recooled to 0° C. in an ice bath while still under nitrogen. The resulting solution of free base was used later.

When the above arginine solution had reached −5° C., 45 mL of N-methylpiperidine was added via syringe followed 5 minutes later by the addition of 46 mL of isobutyl chloroformate (0.95 equivalent) via syringe. The resulting solution was stirred for 15 minutes at −5° C. After this time, the free base solution of N,O-dimethylhydroxylamine generated above was added via cannula over about 15 minutes. Stirring was continued at −5° C. for another 1.5 hours at which time thin layer chromatography (silica gel, 1:10:90 acetic acid/methanol/dichloromethane) indicated that the reaction was complete. The reaction mixture was filtered while still cold, the salts washed with 400 mL of cold tetrahydrofuran and the filtrate concentrated under vacuum on a rotary evaporator to yield a yellow foam.

The crude intermediate was taken up in 300 mL of dichloromethane and applied to a column of silica gel (70–230 mesh, 7×50 cm). The column was first eluted with 2 liters of dichloromethane followed by 2 liters of 2% methanol in dichloromethane. This was followed by elution with 5% methanol in dichloromethane until all of the product had been eluted (the eluent was checked for UV activity and five one-liter fractions were collected once this UV activity was apparent). Fractions containing pure product were pooled and concentrated under vacuum and placed under a high vacuum overnight to yield 120.1 g (88% yield) of N-alpha-t-butoxycarbonyl-N$^g$-nitro-L-arginine-(N,O-dimethylhydroxylamide) as a light yellow foam. This foam was taken up in 300 mL of dichloromethane, 300 mL of toluene, and the volatiles were once again removed under vacuum to remove any residual water or methanol.

120.1 g of N-alpha-t-butoxycarbonyl-N$^g$-nitro-L-arginine-(N,O-dimethylhydroxylamide) (331.4 mmole) was taken up in 2.8 liters of dry (Aldrich sure-seal) tetrahydrofuran and transferred to a dry 5 liter 4-necked round bottom flask equipped with a mechanical stirrer and a low temperature thermometer. The solution was cooled to −70° C. with a dry ice/acetone bath and 300 mL of 1M LiAlH₄ in tetrahydrofuran was added by cannula transfer directly from 100 mL Aldrich sure-seal bottles. An additional 50 mL of 1M LiAlH₄ in tetrahydrofuran was added via syringe (total 331 mL). During the additions, the reaction temperature was kept below –60° C. The reaction was stirred for 0.5 hours at –70° C., the cooling bath removed, and the reaction was slowly allowed to warm to 0° C. (about 2.5 hours). Between –30° C. and –20° C. a thick slurry resulted. When the reaction mixture obtained 0° C., a small aliquot was removed and partitioned between ethyl acetate/2M potassium bisulfate. The organic layer was then analyzed by thin layer chromatography (silica gel, ethyl acetate).

When the reaction was judged to be complete, it was cooled to –70° C. and 503 mL of 2M potassium bisulfate was added via dropping funnel at a slow enough rate to keep the reaction temperature below –30° C. The cooling bath was removed and the reaction mixture was allowed to come to 0° C. over the course of 2 hours at which time a white precipitate was filtered off. The solids were washed with 500 mL of cold tetrahydrofuran. The filtrate was concentrated under vacuum on a rotary evaporator until most of the tetrahydrofuran was removed and the remaining white sludge was mostly aqueous. The crude product was taken up in 1.5 liters of ethyl acetate and washed with 0.2M hydrochloric acid (2×200 mL). The hydrochloric acid extracts were back-extracted with 400 mL of ethyl acetate and the organics were combined and extracted with saturated sodium bicarbonate (2×200 mL). The bicarbonate extracts were also back-extracted with 400 mL of ethyl acetate. The organics were then combined and washed with brine (200 mL) followed by drying over anhydrous sodium sulfate. The solution was filtered, concentrated under vacuum on a rotary evaporator and placed on a high vacuum overnight to yield a white solid (89.0 g) of crude title compound. This was chromatographed on silica gel and eluted with a gradient of 0 to 10% methanol in dichloromethane. The pure fractions were combined and evaporated to yield the title compound as a white solid (75 g, 74%).

Example 3

Preparation of N-alpha-t-butoxycarbonyl-N$^g$-nitro-L-argininal ethyl cyclol.

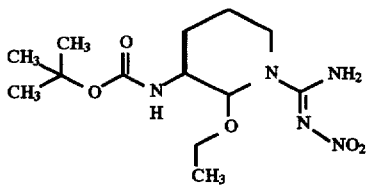

The compound of Example 2 (41.60 g, 0.137 mole) was dissolved in ethanol (200 mL) and concentrated hydrochloric acid (1 mL) was added. After the reaction was complete by TLC (silica gel, 10% methanol in dichloromethane), the solvent was removed under vacuum. The crude product was purified by flash chromatography through a column of silica gel (230–400 mesh) using 0–10% ethyl acetate/dichloromethane as eluent. The combined fractions yielded 36.88 g (81%) of the title compound as pale yellow foam. R$_f$=0.62 (silica gel, 95:5, CH₂Cl₂:methanol).

Example 4

Preparation of N$^g$-nitro-L-argininal ethyl cyclol, hydrochloride salt.

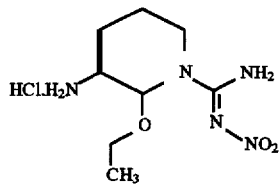

To a solution of the compound of Example 3 (35 g) in 500 mL of absolute ethanol at 0° C. was added slowly 500 mL of absolute ethanol saturated with hydrochloric acid (g). This mixture was allowed to warm to 25° C. and checked by thin-layer chromatography. The appearance of a very polar product was the desired compound. Most of the hydrochloric acid was removed with a stream of dry nitrogen and the resulting organic solvent was removed under vacuum. The resulting 33 g of the title compound as a yellow-white solid was used without further purification.

Example 5

Preparation of (D)-N$^g$-NO₂-arginine sarcosine benzyl ester hydrochloride salt.

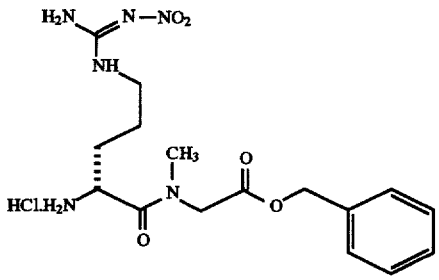

To a stirring solution of Boc-D-N$^g$-nitroarginine (6.2 g, 19.4 mmole) in 100 mL of dry dimethylformamide was added sarcosine benzyl ester para-toluenesulfonic acid salt (8.2 g, 23.3 mmole) followed by benzotriazol-1-yl-oxy-tris-(dimethylamino)-phosphonium hexafluorophosphate (8.6 g, 19.4 mmole) and N-methylmorpholine (10.6 mL, 97.1 mmole). The mixture was stirred for 16 hours at room temperature. The reaction mixture was dissolved in 900 mL of ethyl acetate and washed with 300 mL each of water, 1M aqueous hydrochloric acid, water, saturated aqueous sodium bicarbonate and brine. The organic phase was dried over anhydrous magnesium sulfate, filtered and the solvent removed in vacuo. Rf=0.39 (1:9 methanol:dichloromethane). The resulting oil was dissolved in dichloromethane (50 mL) and treated with 50 mL of 4.0M solution of hydrochloric acid in dioxane. After 5 hours, the title compound precipitated when the reaction mixture was poured into ether (500 mL) with vigorous stirring. The precipitate was filtered and dried in vacuo to provide 8 g (quantitative yield) of the title compound as an off-white powder.

Example 6

Preparation of (D)-camphorsulfonyl-(D)-N$^g$-NO₂-arginine sarcosine benzyl ester.

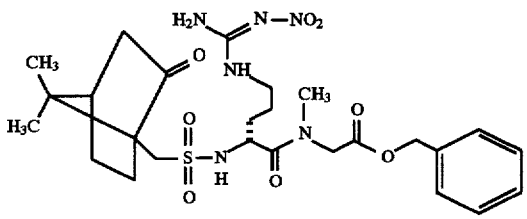

To a solution of the compound of Example 5 (4.19 g, 10.1 mmole) in 10 mL of dry dimethylformamide and 50 mL tetrahydrofuran was added (D)-camphorsulfonyl chloride (3.7 g, 15.1 mmole) followed by triethylamine (7.0 mL, 50.3 mmole). The mixture was stirred for 16 hours at room temperature. The reaction mixture was dissolved in 800 mL of ethyl acetate and washed with 200 mL each of water, 1M aqueous hydrochloric acid, water, saturated aqueous sodium bicarbonate and brine. The organic phase was dried over anhydrous magnesium sulfate, filtered and the solvent removed in vacuo. The resulting oil was dissolved in dichloromethane and filtered through silica, eluting first with dichloromethane (500 mL) then 1:9 methanol:dichloromethane (1000 mL). The methanol:dichloromethane fraction was concentrated to provide 5.7 g (95% yield) of the title compound as an off-white foam. Rf=0.45 (1:9 methanol:dichloromethane).

Example 7

Preparation of (D)-camphorsulfonyl-(D)-N$^g$-NO$_2$-arginine sarcosine.

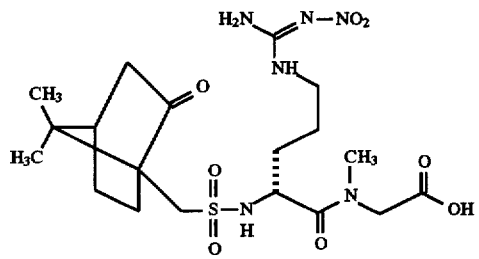

10% palladium on carbon (2.5 g) was added to a solution of the compound of Example 6 (5.7 g, 9.57 mmole) in 300 mL of methanol under a nitrogen blanket. The mixture was hydrogenated at 1 atmosphere for 16 hours. The mixture was filtered and then concentrated to provide 4.5 g (96% yield) of the title compound as a white foam.

Example 8

Preparation of (D)-camphorsulfonyl-(D)-N$^g$-NO$_2$-arginine-sarcosine-N$^g$-NO$_2$-arginine cyclic-OEt aminal.

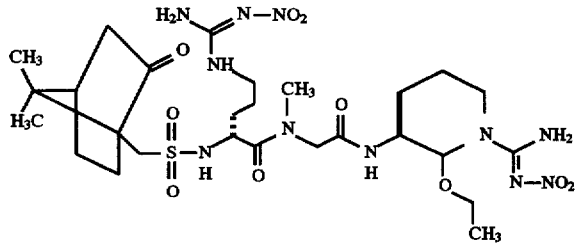

The compound of Example 4 (1.64 g, 6.1 mmole) and the the compound of Example 7 (2 g, 4.1 mmole) were dissolved with stirring in 20 mL of dry acetonitrile. To this mixture was added 1-hydroxy-7-azabenzotriazole (0.28 g, 2.0 mmole) and O-(7-azabenzotriazol-1-yl)-1,1,3,3-tetramethyluronium hexafluorophosphate (1.5 g, 4.1 mmole) followed by N-methylmorpholine (1.7 mL, 15.8 mmole). After 16 hours, the reaction mixture was diluted with 600 mL ethyl acetate and extracted with 150 mL each of water, 1M aqueous hydrochloric acid, water, saturated aqueous sodium bicarbonate and brine. The organic phase was dried over anhydrous magnesium sulfate, filtered and the solvent removed in vacuo. Chromatography of the resulting oil (silica, 4:1:4 hexanes:methanol:dichloromethane) afforded 1.25 g (43% yield) of the title compound as an off-white foam. Rf=0.26 (1:9 methanol:dichloromethane).

Example 9

Preparation of (D)-camphorsulfonyl-(D)-arginine-sarcosine-arginine cyclic-OEt aminal.

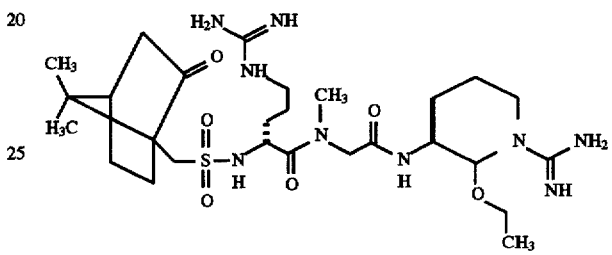

1.25 g of 10% palladium on carbon was placed in a 500 mL PARR bottle to which 10 mL of water and 4 mL of glacial acetic acid was added. To this mixture was added a solution of the compound of Example 8 (1.25 g, 1.74 mmole) in 100 mL of methanol. The mixture was then shaken under a hydrogen atmosphere at 40 psi for 3 days. The catalyst was removed by filtration and the filtrate concentrated in vacuo. The resulting oil was azeotroped with toluene to remove the remaining acetic acid to afford about 1 g (quantitative yield) of the title compound.

Example 10

Preparation of (D)-camphorsulfonyl-(D)-arginine-sarcosine-arginine aldehyde.

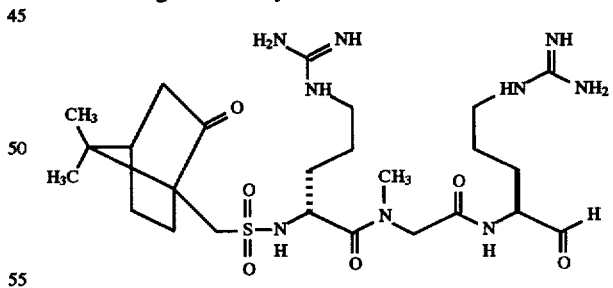

The compound of Example 9 (1 g, 1.7 mmole) was dissolved in 20 mL of 50:50 water:acetonitrile with stirring and cooled to 0° C. in an ice water bath. To this solution was slowly added 50 mL of a 60 wt % solution of hexafluorophosphoric acid in water. After 1 hour, the pH of the reaction mixture was adjusted to about pH 4 using saturated aqueous sodium acetate. This mixture was filtered through a plug of Celite. The title compound was obtained by purification of the filtrate by preparative HPLC (2 inch Vydak C18 column using a gradient consisting of 7–28% acetonitrile in water containing 0.1% trifluoroacetic acid run over 60 minutes at a flowrate of 115 mL/minute) and lyophilization of the pooled fractions. Mass Spec(FAB) confirmed the calculated molecular weight of 598.7.

Example 11

Preparation of sarcosine-O-fluorenylmethyl ester hydrochloride salt.

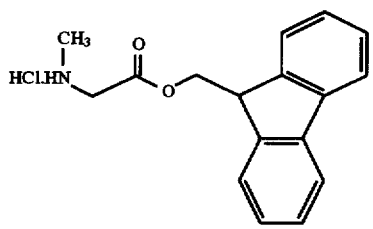

To a solution of Boc-sarcosine (30 g, 158 mmole) in 500 mL dichloromethane was added with stirring carbonyl diimidazole (25.7 g, 158 mmole). After 15 minutes, 9-fluorene methanol (29.5 g, 150 mmole) was added and stirring was continued. After 16 hours, the reaction mixture was diluted with 1200 mL ethyl acetate and extracted with 300 mL each of water, 1M aqueous hydrochloric acid, water, saturated aqueous sodium bicarbonate and brine. The organic phase was dried over anhydrous magnesium sulfate, filtered and the solvent removed in vacuo. The resulting oil was dissolved in 500 mL dichloromethane and treated with 100 mL of a 4.0M solution of hydrochloric acid in dioxane. After 12 hours, the title compound was precipitated by pouring the reaction mixture into ether (1000 mL) with vigorous stirring. The precipitate was filtered and dried in vacuo to provide 35 g (73% yield) of the title compound as an off-white powder.

Example 12

Preparation of (D)-N$^g$-NO$_2$-arginine sarcosine-O-fluorenylmethyl ester hydrochloride salt.

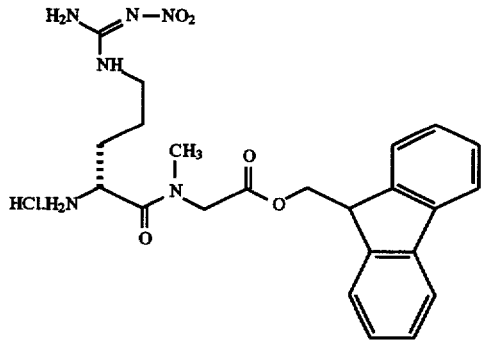

To a stirring solution of Boc-(D)-N$^g$-nitroarginine (10 g, 31.3 mole) in 150 mL of dry dimethylformamide was added the compound of Example 11 (21.2 g, 40.7 mole) followed by benzotriazol-1-yl-oxy-tris-(dimethylamino)-phosphonium hexafluorophosphate (13.9 g, 31.3 mole) and 2,4,6-collidine (120.7 mL, 156.5 mole). The mixture was stirred for 16 hours at room temperature. The reaction mixture was dissolved in 1200 mL of ethyl acetate and washed with 350 mL each of water, 1M aqueous hydrochloric acid, water, saturated aqueous sodium bicarbonate and brine. The organic phase was dried over anhydrous magnesium sulfate, filtered and the solvent removed in vacuo. Rf=0.45 (1:9 methanol:dichloromethane).

The resulting oil was dissolved in dichloromethane (500 mL) and treated with 100 mL of 4.0M solution of hydrochloric acid in dioxane. After 12 hours, the title compound was precipitated by pouring the reaction mixture into diethyl ether (500 mL) with vigorous stirring. The precipitate was filtered and dried in vacuo to provide 15 g (95% yield) of the title compound as an off-white powder.

Example 13

Preparation of benzylsulfonyl-(D)-N$^g$-NO$_2$-arginine sarcosine.

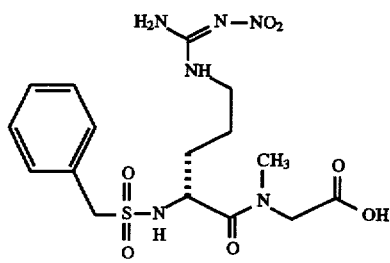

To a solution of the compound of Example 12 (7.5 g, 14.8 mmole) in 30 mL of dry dimethylformamide and 45 mL acetonitrile was added alpha-toluenesulfonyl chloride (4.2 g, 22.3 mmole) followed by diisopropylethylamine (12.9 mL, 74.3 mmole). The mixture was stirred for 16 hours at room temperature, then piperidine (7.3 mL, 74.2 mmole) was added to remove the fluorenylmethyl group. After another 12 hours, the reaction mixture was dissolved in 600 mL of ethyl acetate and extracted into saturated aqueous sodium bicarbonate (2×200 mL). The combined aqueous fractions were washed with 200 mL ethyl acetate and then acidified to about pH 4 using concentrated hydrochloric acid. This was then extracted with ethyl acetate (2×300 mL) and the organic fractions were washed with 300 mL brine, dried over anhydrous magnesium sulfate, filtered and the solvent removed in vacuo to provide 3.28 g (50% yield) of the title compound as an off-white foam. Rf=0.15 (1:9 methanol:dichloromethane).

Example 14

Preparation of benzylsulfonyl-(D)-N$^g$-NO$_2$-arginine-sarcosine-N$^g$-NO$_2$-arginine cyclic-OEt aminal.

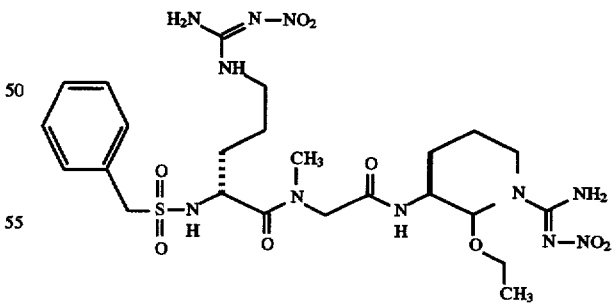

The compound of Example 4 (2.25 g, 8.42 mmole) and the compound of Example 13 (3.12 g, 7.02 mmole) were dissolved with stirring in 10 mL of dry dimethylformamide and 30 mL of dry acetonitrile. To this mixture was added 1-ethyl-3-(3-dimethylamino-propyl)carbodiimide hydrochloride salt (2.02 g, 10.5 mmole) and 1-hydroxybenzotriazole monohydrate (1.42 g, 10.5 mmole) followed by diisopropylethylamine (6 mL, 4.5 mmole).

After 16 hours, the reaction mixture was concentrated in vacuo and then diluted with 600 mL ethyl acetate and extracted with 150 mL each of water, 1M aqueous hydrochloric acid, water, saturated aqueous sodium bicarbonate and brine. The organic phase was dried over anhydrous magnesium sulfate, filtered and the solvent removed in vacuo to give 3.29 g (71% yield) of the title compound as an off-white foam. Rf=two spots, 0.40 and 0.50 (1:9 methanol:dichloromethane).

Example 15

Preparation of benzylsulfonyl-(D)-arginine-sarcosine-arginine cyclic-OEt aminal.

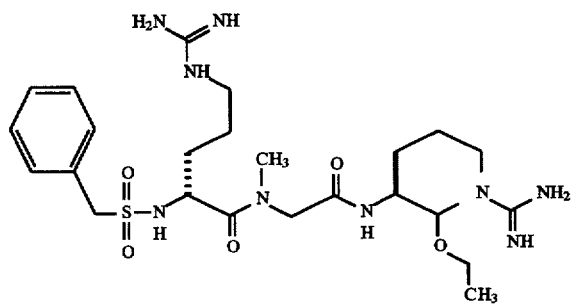

1 g of 10% palladium on carbon was placed in a 500 mL PARR bottle. To this was added 10 mL of water and 10 mL of glacial acetic acid. To this mixture was added a solution of the compound of Example 14 (3.29 g, 5 mmole) in 100 mL of ethanol. The mixture was then shaken under a hydrogen atmosphere at 40 psi for 5 days. (The catalyst was removed and replaced 2 times). The catalyst was then removed by filtration and the filtrate concentrated in vacuo. The resulting oil was azeotroped with toluene to remove the remaining acetic acid to afford about 2.8 g (quantitative yield) of the title compound.

Example 16

Preparation of benzylsulfonyl-(D)-arginine-sarcosine-arginine aldehyde.

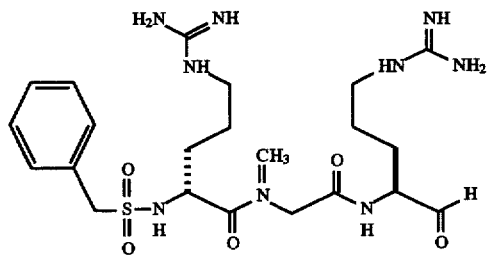

The compound of Example 15 (2.8 g, 5 mmole) was dissolved in 40 mL water and cooled to 0° C. in an ice water bath with stirring. To this solution was slowly added 40 mL of concentrated hydrochloric acid. After 1.5 hour, the reaction was judged complete by HPLC and the pH of the reaction mixture was adjusted to about pH 4 using saturated aqueous sodium acetate. This mixture was filtered through a plug of Celite. The title compound was obtained by purification from the filtrate by preparative HPLC (2 inch Vydak C18 column using a gradient consisting of 5–17% acetonitrile in water containing 0.1% trifluoroacetic acid run over 55 minutes at a flowrate of 115 mL/minute) and lyophilization of the pooled fractions. Mass Spec(FAB) confirmed the calculated molecular weight of 539.6.

Example 17

Preparation of (2-carbomethoxy)-benzenesulfonyl-(D)-$N^g$-nitroargininyl-sarcosine-O-fluorenylmethyl ester.

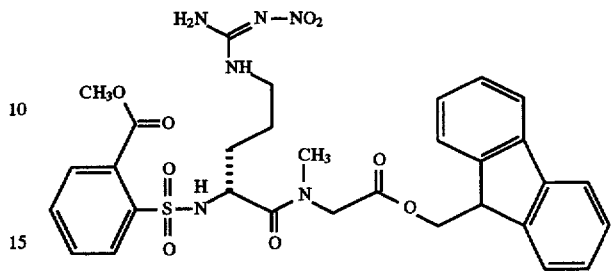

Collidine (0.99 mL, 7.5 mmole) was added to suspension of the compound of Example 12 (1.5 g, 3.0 mmole) and 2-carbomethoxybenzenesulfonyl chloride (0.77 g, 3.3 mmole) in acetonitrile (25 mL) at room temperature. After stirring for 18 hours, distilled water (30 mL) was added, the reaction mixture was concentrated under vacuum, and the residue was extracted into ethyl acetate (2×50 mL), washed with 3% aqueous hydrochloric acid (50 mL), brine (50 mL), dried over anhydrous magnesium sulfate, and concentrated under vacuum to yield the title compound as a pale yellow foam (1.7 g, 84%). Rf=0.81; 9:1 dichloromethane:methanol.

Example 18

Preparation of (2-carbomethoxy)benzenesulfonyl-(D)-$N^g$-nitroargininyl-sarcosine.

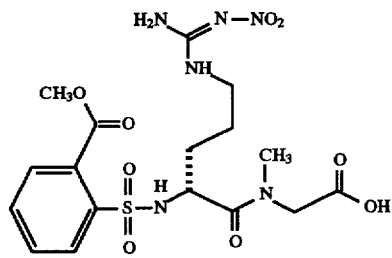

Piperidine (2.5 mL, 25 mmole) was added to a solution of the compound of Example 17 (1.7 g, 2.5 mmole) in acetonitrile (20 mL). After stirring 1.5 hours at room temperature, the reaction was concentrated under vacuum and the residue was diluted with ethyl acetate (50 mL) extracted with aqueous sodium bicarbonate (2×50 mL), acidified with concentrated hydrochloric acid to pH 1, extracted into ethyl acetate, washed with brine, dried over anhydrous magnesium sulfate, and concentrated under vacuum to yield the title compound as a white foam (1.0 g, 80%). Rf=0.10; 9:1 dichloromethane:methanol.

Example 19

Preparation of (2-carbomethoxy)benzenesulfonyl-(D)-$N^g$-nitroargininyl-sarcosine-$N^g$-nitroarginine ethyl aminal.

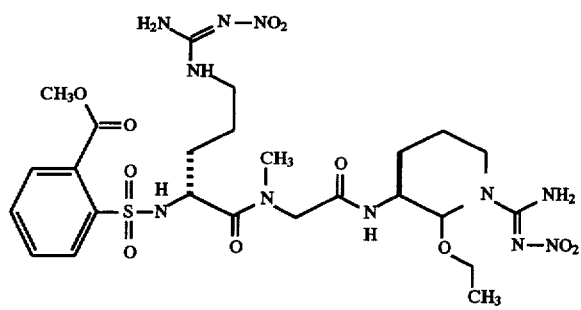

The compounds of Example 18 (1.0 g, 2.0 mmole) and the compound of Example 4 (0.66 g, 2.5 mmole) were suspended in acetonitrile (20 mL), followed by 1-ethyl-3-(3-dimethylamino-propyl)carbodiimide hydrochloride salt (0.48 g, 2.5 mmole) and 1-hydroxybenzotriazole monohydrate (0.34 g, 2.5 mmole). The reaction was stirred for 30 minutes, then N-methylmorpholine (0.70 mL, 6.0 mmole) was added. After stirring for 48 hours at room temperature, the reaction was concentrated under vacuum, and the residue was extracted into ethyl acetate (2×50 mL), washed with 3% aqueous hydrochloric acid (50 mL), brine (50 mL), dried over anhydrous magnesium sulfate, and concentrated under vacuum to yield the title compound as a pale yellow foam (0.77 g, 55%). Rf=0.73; 9:1 dichloromethane:methanol.

Example 20

Preparation of (2-carbomethoxy)benzenesulfonyl-(D)-argininyl-sarcosine-arginine ethyl aminal.

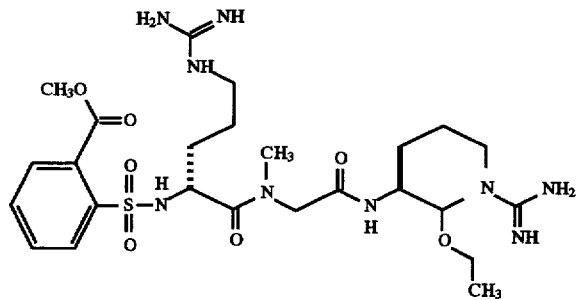

The compound of Example 19 (0.77 g, 1.1 mmole) was dissolved in methanol (20 mL), acetic acid (5.0 mL), and distilled water (5.0 mL), and the solution was placed in a 250 mL Parr bottle. The vessel was purged with argon and then 10% palladium on carbon catalyst (0.3 g) was added. The reaction mixture was shaken under hydrogen (50 psi) for 2.5 days, then was filtered through Celite and concentrated under vacuum to give the title compound as an off-white foam.

Example 21

Preparation of (2-carbomethoxy)benzenesulfonyl-(D)-argininyl-sarcosine-argininal.

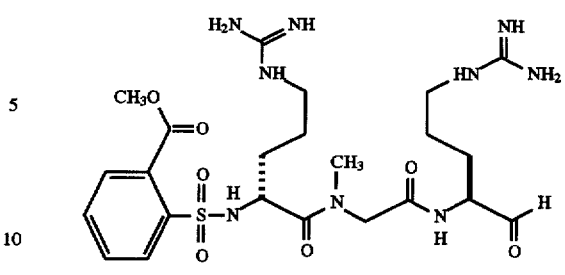

The compound of Example 20 (0.3 g, 0.49 mmole) was dissolved in 6N hydrochloric acid (8.0 mL, 48 mmole) at 0° C. The reaction mixture was stirred at 0° C. for 4 hours, then at room temperature for 1.5 hours. The reaction mixture was recooled to 0° C., and saturated sodium acetate (20 mL) was added (to pH 4). Purification on reverse phase HPLC, followed by lyophilization, gave the product as a white powder. Fast atom bombardment mass spectrometry confirmed the theoretical molecular weight of 583.

Example 22

Preparation of (D)-camphorsulfonyl-L-methionine sulfone-O-benzyl ester.

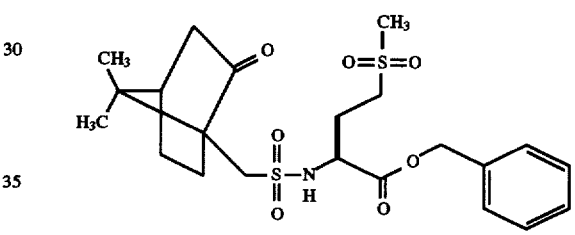

To a solution of L-methionine sulfone-O-benzyl ester hydrochloride salt (3.86 g, 12.5 mmole) in 120 mL of dry 50.50 dimethylformamide:tetrahydrofuran was added D-camphorsulfonyl chloride (4.7 g, 18.7 mmole) followed by triethylamine (8.7 mL, 62.5 mmole). The mixture was stirred for 16 hours at room temperature. The reaction mixture was dissolved in 800 mL of ethyl acetate and washed with 300 mL each of water, 1M aqueous hydrochloric acid, water, saturated aqueous sodium bicarbonate and brine. The organic phase was dried over anhydrous magnesium sulfate, filtered and the solvent removed in vacuo. The resulting oil was dissolved in dichloromethane and filtered through silica, eluting first with dichloromethane (500 mL) then 1:9 methanol:dichloromethane (1000 mL). The methanol:dichloromethane fraction was concentrated to provide 5.4 g (88% yield) of the title compound as an off-white foam. Rf=0.65 (1:9 methanol:dichloromethane).

Example 23

Preparation of (D)-camphorsulfonyl-L-methionine sulfone.

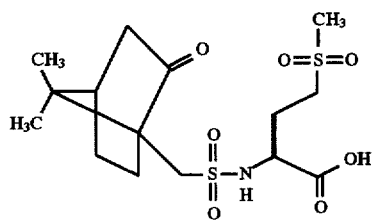

To a solution of the compound of Example 22 (5.4 g, 11.1 mmole) in 400 mL of methanol under a nitrogen blanket, was added 10% palladium on carbon (2.5 g). The mixture was hydrogenated at 1 atmosphere for 16 hours. The mixture was then filtered and concentrated in vacuo to provide 4.1 g (94% yield) of the title compound as a white foam. Rf=0.2 (1:9 methanol:dichloromethane).

Example 24

Preparation of (D)-camphorsulfonyl-L-methionine sulfone-sarcosine-O-benzyl ester.

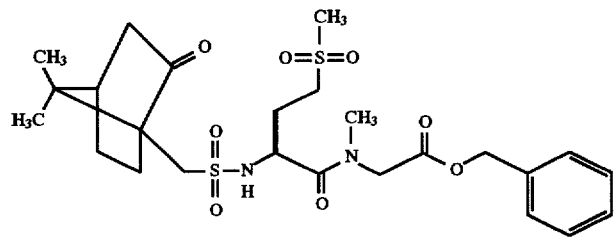

To a solution of the compound of Example 23 (3.7 g, 9.4 mmole) in 47 mL of dimethylformamide was added with stirring sarcosine-O-benzyl ester para-toluenesulfonate salt (3.3 g, 9.4 mmole) followed by N-methylmorpholine (5.1 mL, 47 mmole) and benzotriazol-1-yl-oxy-tris-(dimethylamino)-phosphonium hexafluorophosphate (5.4 g, 9.4 mmole). The stirring was continued for 16 hours. The reaction mixture was dissolved in 700 mL of ethyl acetate and washed with 250 mL each of water, 1M aqueous hydrochloric acid, water, saturated aqueous sodium bicarbonate and brine. The organic phase was dried over anhydrous magnesium sulfate, filtered and the solvent removed in vacuo to provide 5.16 g (96% yield) of the title compound as an off-white foam. Rf=0.3 (1:9 methanol:dichloromethane).

Example 25

Preparation of (D)-camphorsulfonyl-L-methionine-sulfone sarcosine.

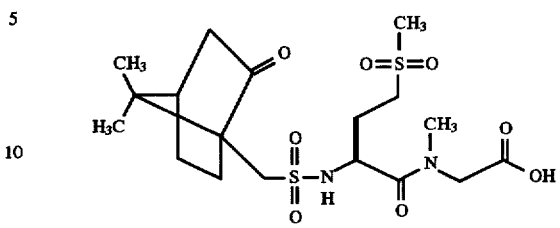

To a solution of the compound of Example 24 (5.16 g, 9.01 mmole) in 300 mL of methanol under a nitrogen blanket, was added 10% palladium on carbon (4 g) and the mixture was hydrogenated at 1 atmosphere for 16 hours. The mixture was then filtered and concentrated in vacuo to provide 3.79 g (88% yield) of the title compound as a white foam. Rf=0.2 (1:9 methanol:dichloromethane).

Example 26

Preparation of (D)-camphorsulfonyl-L-methionine sulfone-sarcosine-$N^g$-$NO_2$-arginine cyclic-OEt aminal.

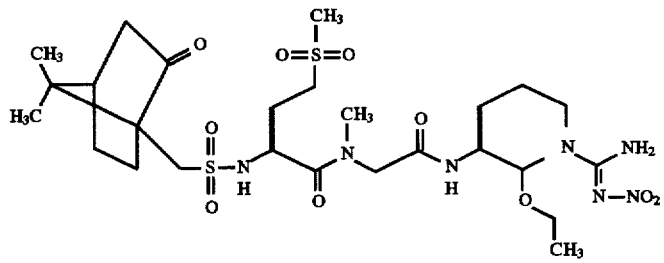

The compound of Example 4 (0.85 g, 3.1 mmole) was dissolved with stirring in 6 mL of dry dimethylformamide and 16 mL of dry acetonitrile. To this mixture was added N-methylmorpholine (1.7 mL, 15.8 mmole) followed by the compound of Example 25 (1.15 g, 2.38 mmole), 1-hydroxybenzotriazole monohydrate (0.65 g, 4.7 mmole) and 2-(1H-benzotriazol-1-yl)-1,1,3,3-tetramethyluronium hexafluorophosphate (1.8 g, 4.7 mmole). After 16 hours, the reaction mixture was diluted with 600 mL ethyl acetate and extracted with 200 mL each of water, 1M aqueous hydrochloric acid, water, saturated aqueous sodium bicarbonate and brine. The organic phase was dried over anhydrous magnesium sulfate, filtered and the solvent removed in vacuo. Chromatography of the resulting oil on silica eluting with 4:1:4 hexanes:methanol:dichloromethane afforded 0.61 g (35% yield) of the title compound as an off-white foam. Rf=0.45 (1:9 methanol:dichloromethane).

Example 27

Preparation of (D)-camphorsulfonyl-L-methionine sulfone-sarcosine-arginine cyclic-OEt aminal.

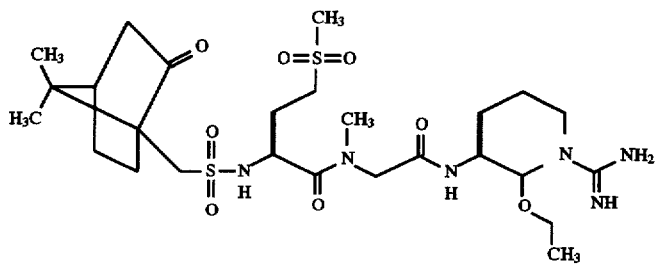

0.5 g of 10% palladium on carbon was placed in a 500 mL PARR bottle. To this was added 6 mL of water and 2 mL of glacial acetic acid. To this mixture was added a solution of the compound of Example 26 (0.61 g, 0.84 mmole) in 60 mL of methanol. The mixture was then shaken under a hydrogen atmosphere at 40 psi for 3 days. The catalyst was then removed by filtration and the filtrate concentrated in vacuo. The resulting oil was azeotroped with toluene to remove the remaining acetic acid to afford 0.5 g (87% yield) of the title compound.

Example 28

Preparation of (D)-camphorsulfonyl-L-methionine sulfone-sarcosine-arginine aldehyde.

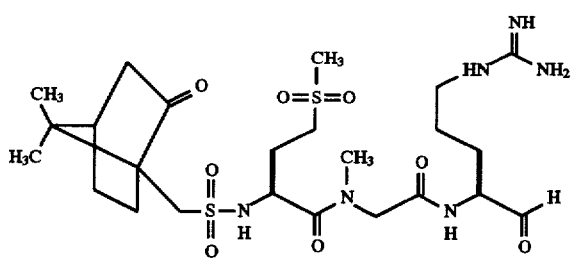

The compound of Example 27 (0.5 g, 0.73 mmole) was dissolved in 20 mL of 50:50 water:acetonitrile with stirring and cooled to 0° C. in an ice water bath. To this solution was slowly added 30 mL of a 60 wt % solution of hexafluorophosphoric acid in water. After 1 hour, the pH of the reaction mixture was adjusted to about pH 4 using saturated aqueous sodium acetate. This mixture was filtered through a plug of Celite. The title compound was obtained by purification from the filtrate by preparative HPLC (2 inch Vydak C18 column using a gradient consisting of 15–35% acetonitrile in water containing 0.1% trifluoroacetic acid run over 40 minutes at a flowrate of 115 mL/minute) and lyophilization of the pooled fractions. Mass Spec(FAB) confirmed the calculated molecular weight of 605.7.

Example 29

Preparation of N-Boc-(D)-methioninyl sarcosine benzyl ester.

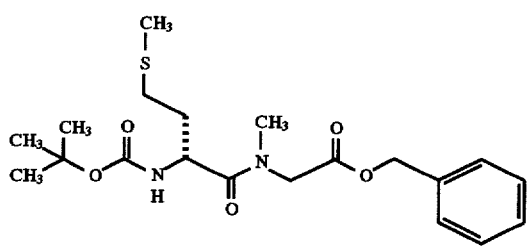

N-Boc-(D)-methionine (17.1 g, 68.58 mmole) and sarcosine benzyl ester tosylate salt (24.08 g, 68.60 mmole) were suspended in 110 mL of acetonitrile and 25 mL of dimethylformamide at 0° C., then benzotriazol-1-yl-oxy-tris-(dimethylamino)-phosphoniumhexafluorophosphate (30.34 g, 68.58 mmole) and N-methylmorpholine (20.83 g, 205.83 mmole) were added. The ice bath was removed after 30 minutes and the reaction was stirred for 18 hours at room temperature. The reaction mixture was reduced in volume under vacuum at 25° C. to give an oil. The oil was dissolved in ethyl acetate (250 mL), then successively washed with 1N hydrochloric acid (1×50 mL), saturated sodium bicarbonate (1×50 mL) and brine (1×50 mL). The organic layer was dried with anhydrous magnesium sulfate and evaporated under vacuum to give crude product. The crude product was purified by column chromatography on silica gel, eluting with 60:40 hexane:ethyl acetate to yield 26.07 g (92.6%) of the title compound as an oil. Thin layer chromatography analysis of the title compound showed a single spot with Rf=0.55 (silica, 3:2 ethyl acetate/hexane).

Example 30

Preparation of N-Boc-(D)-methioninylsulfone sarcosine benzyl ester.

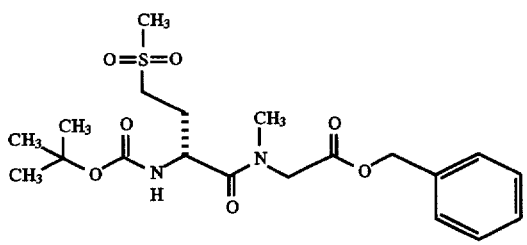

The compound of Example 29 (26.0 g, 63.3 mmole) was dissolved in 335 mL of glacial acetic acid. Sodium perborate tetrahydrate (48.7 g, 316.5 mmole) was added and the mixture was heated to 55° C. After 2.5 hours at this temperature, the reaction mixture was diluted with 1.1 liters of brine, the aqueous layer was extracted with ethyl acetate (4×250 mL) and the combined organic extracts were dried with anhydrous magnesium sulfate. This solution was filtered and evaporated under vacuum, then repeatedly azeotroped with toluene (200 mL) under vacuum to remove acetic acid. The residual slurry was dissolved in ethyl acetate (200 mL), filtered and the filtrate evaporated to yield 24.15 g (86.2%) of the title compound as a white solid. Thin layer chromatography analysis of the title compound showed a single spot with Rf=0.30 (silica, 2:3 ethyl acetate:hexane).

Example 31

Preparation of N-benzylsulfonyl-(D)-methioninylsulfone sarcosine benzyl ester.

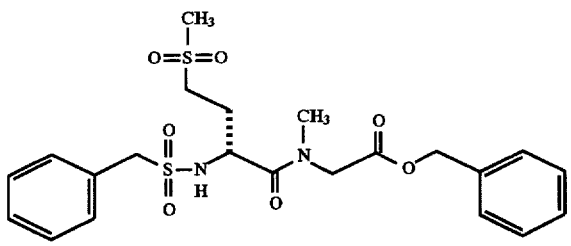

A solution of the compound of Example 30 (7.0 g, 15.8 mmole) in 5 mL of dichloromethane was prepared. 27 mL of 4M hydrochloric acid in dioxane was added and the mixture was stirred for several hours at room temperature until all starting material was consumed. The mixture was evaporated under vacuum and the resulting oil was dissolved in acetonitrile and then evaporated under vacuum. This was done three times. The remaining oil was suspended in 17 mL of acetonitrile and 5 mL of dimethylformamide, cooled to ice bath temperature, then benzylsulfonyl chloride (5.28 g, 23.7 mmole) and N-methylmorpholine (4.80 g, 47.5 mmole) were added. The reaction was removed from the ice bath after 30 minutes and stirred at room temperature for 18 hours. The reaction mixture was reduced in volume under vacuum to an oil. The oil was taken up in 200 mL ethyl acetate and washed successively with 1N hydrochloric acid (1×50 mL), saturated sodium bicarbonate (1×50 mL) and brine (1×50 mL). After drying with anhydrous magnesium sulfate, the organic layer was evaporated under vacuum to give crude product. The crude product was purified by column chromatography on silica gel, eluting with 3:7 hexane:ethyl acetate to yield 4.42 g (56.3% yield) of the title compound as a solid. Thin layer chromatography analysis of the title compound showed a single spot with Rf=0.70 (silica, 95:5 dichloromethane:methanol).

Example 32

Preparation of N-benzylsulfonyl-(D)-methioninylsulfone sarcosine acid.

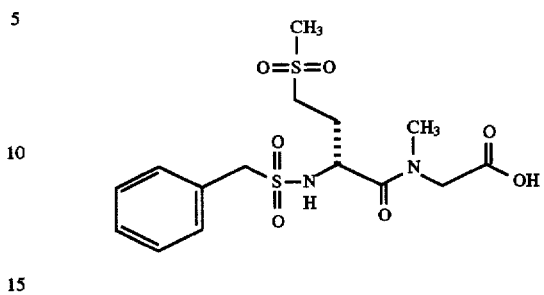

The compound of Example 31 (4.42 g, 8.9 mmole) was dissolved in tetrahydrofuran (200 mL), 0.8 g of 10% palladium on carbon was added and the mixture was stirred under hydrogen gas at atmospheric pressure for 18 hours. After the catalyst was filtered off the reaction mixture, the solvent was removed under vacuum and the resulting oil was taken up in a solution of saturated sodium bicarbonate. This solution was then extracted with ethyl acetate (1×150 mL) and the organic layer was decanted off. The remaining aqueous layer was layered with 100 mL of ethyl acetate and acidified with 3N hydrochloric acid to pH 2 (pH papers). After the phases separated, the organic layer was saved and the aqueous layer was then further extracted with ethyl acetate (3×100 mL). The organic extracts were combined and washed with brine, dried with anhydrous magnesium sulfate, filtered and evaporated under vacuum to give 3.17 g (yield 87.6%) of the title compound as a foamy solid. Thin layer chromatography analysis of the title compound showed a single spot with Rf=0.50 (silica, 90:10:2 dichloromethane:methanol:acetic acid).

Example 33

Preparation of N-benzylsulfonyl-(D)-methioninylsulfone sarcosine nitroarginine ethyl aminal.

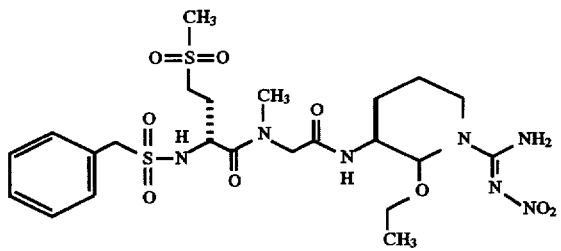

The compound of Example 32 (1.22 g, 3 mmole) and the compound of Example 4 (1.6 g, 6 mmole) were suspended in 15 mL of acetonitrile and 9 mL of dimethylformamide, then 1-hydroxybenzotriazole monohydrate (0.61 g, 4.5 mmole), 2-(1H-benzotriazol-1-yl)-1,1,3,3-tetramethyluronium hexafluorophosphate (1.71 g, 4.5 mmole) and N-methylmorpholine (1.5 g, 15 mmole) were added. The reaction was stirred for 3 days at room temperature. The reaction mixture was reduced in volume under vacuum at 25° C. to give an oil. The oil was dissolved in ethyl acetate (600 mL), then successively washed with 1N hydrochloric acid (1×150 mL), saturated sodium bicarbonate (1×150 mL) and brine (1×150 mL). The organic layer was dried with anhydrous magnesium sulfate and evaporated under vacuum to give crude product. The crude product was purified by column chromatography on silica gel, eluting with 97.5:2.5 dichloromethane:methanol to yield 0.6 g (32.3%) of the title compound as a solid. Thin layer chromatography analysis of the title compound showed a single spot with Rf 0.60 (silica, 90:10:2 dichloromethane:methanol:acetic acid).

Example 34

Preparation of N-benzylsulfonyl-(D)-methioninylsulfone sarcosine arginine ethyl aminal, acetate salt.

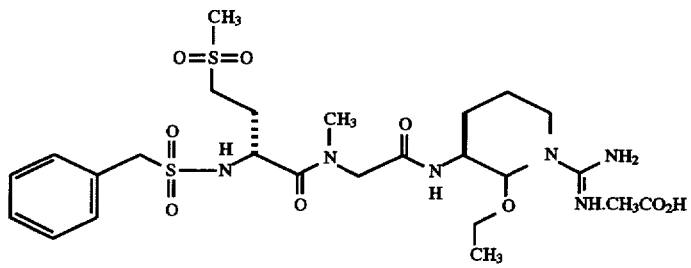

The compound of Example 33 (0.50 g, 0.80 mmole) was dissolved in 40 mL of methanol, 7 mL of water and 0.3 mL of glacial acetic acid. 0.25 g of 10% Palladium on carbon catalyst was added to the solution and the mixture was placed on a PARR shaker at 40 psi hydrogen for 18 hours at room temperature, at which point the starting material was consumed. The catalyst was filtered and the reaction solution was reduced in volume under vacuum at 25° C. to leave an oil. Toluene was added and evaporated several times, then methanol was added and evaporated to yield 0.48 g (95%) of the title compound as a white solid.

Example 35

Preparation of N-benzylsulfonyl-(D)-methioninylsulfone sarcosine argininal.

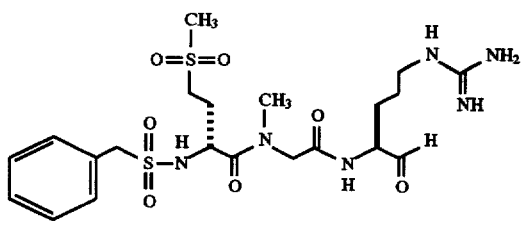

The compound of Example 34 (0.48 g, 0.75 mmole) was placed in a plastic reaction vessel and dissolved by addition of 5 mL of acetonitrile and 5 mL of deionized water. The solution was cooled to 0° C., then 10 mL of hexafluorophosphoric acid (60% wt. in water) at 0° C. was added. The reaction was stirred at 0° C. for 2.0 hours at which time all the starting material was consumed. The reaction was quenched with 100 mL of 2.5M sodium acetate, this raised the pH to pH 5. The title compound was isolated by preparative HPLC purification (2 inch Vydak C-18 at 115 mL/minute, gradient 6–25% acetonitrile in water containing 0.1% TFA run over 50 minutes). Mass Spec(FAB) confirmed the calculated molecular weight of 546.6.

Example 36

Preparation of S-(t-butyl acetate)-L-cysteine.

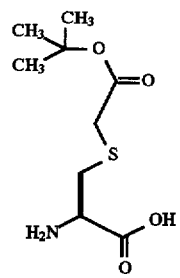

A 360 mL aqueous solution of L-cysteine hydrochloride monohydrate (60.0 g, 341.7 mole) and sodium hydroxide (27.33 g, 683.4 mole), at room temperature, was treated with a solution of t-butyl bromoacetate (72.3 g, 370.6 mmole) in 130 mL of dioxane over 30 minutes. This reaction mixture was stirred for 18 hours, during which time a thick precipitate formed. The solid was filtered off, washed with diethyl ether (100 mL) and dried under high vacuum at 40° C. to give 82.5 g (103.8% crude yield includes occluded inorganic salt) of the title compound.

Example 37

Preparation of N-Boc-S-(t-butyl acetate)-L-cysteine.

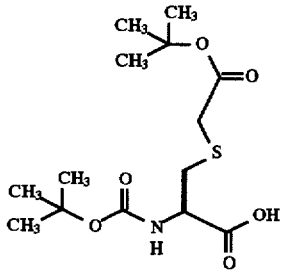

The compound of Example 36 (82.5 g, 341.7 mmole) and sodium bicarbonate (33.96 g, 404 mmole) were suspended in 600 mL of deionized water. A solution of di-t-butyl dicarbonate (80.88 g, 370 mmole) in 350 mL of dioxane was added and the slurry was stirred for 18 hours. The slurry was extracted with diethyl ether (2×100 mL). The slurry was layered with ethyl acetate (200 mL) and acidified with 1N hydrochloric acid to pH 2 (pH papers). The resulting organic layer was saved and the remaining aqueous layer was further extracted with ethyl acetate (2×200 mL). The organic extracts were combined, washed with brine, dried with anhydrous magnesium sulfate and the solvent evaporated under vacuum to yield 84.3 g (74.6%) of the title compound as a clear oil. Thin layer chromatography analysis of the title compound showed a single spot with Rf=0.55, (silica; 90:10:2 dichloromethane:methanol:acetic acid).

Example 38

Preparation of N-Boc-S-(t-butyl acetate)-L-cysteine sarcosine-O-benzyl ester.

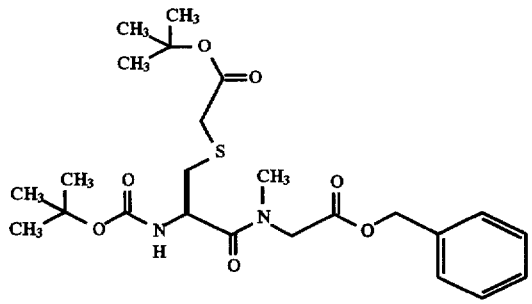

The compound of Example 37 (57.32 g, 170.9 mmole) and sarcosine benzyl ester tosylate salt (60.0 g, 170.9 mmole) were suspended in 300 mL of acetonitrile and 60 mL of dimethylformamide at 0° C., then benzotriazol-1-yl-oxy-tris-(dimethylamino)-phosphonium hexafluorophosphate (75.2 g, 170.9 mmole) and N-methylmorpholine (51.9 g, 512.7 mmole) were added. The ice bath was removed after 30 minutes and the reaction was stirred for 48 hours at room temperature. The reaction mixture was reduced in volume under vacuum at 25° C. to give an oil. The oil was dissolved in ethyl acetate (250 mL), then successively washed with 1N hydrochloric acid (1×50 mL), saturated sodium bicarbonate (1×50 mL) and brine (1×50 mL). The organic layer was dried with anhydrous magnesium sulfate and evaporated under vacuum to give crude product. The crude product was purified by column chromatography on silica gel, eluting with 60:40 hexane:ethyl acetate to yield 68.1 g (80.2%) of the title compound as an oil. Thin layer chromatography analysis of the title compound showed a single spot with Rf=0.64 (silica, 3:2 ethyl acetate:hexane).

Example 39

Preparation of S-(t-butyl acetate)-L-cysteine sulfone sarcosine-O-benzyl ester, hydrochloride salt.

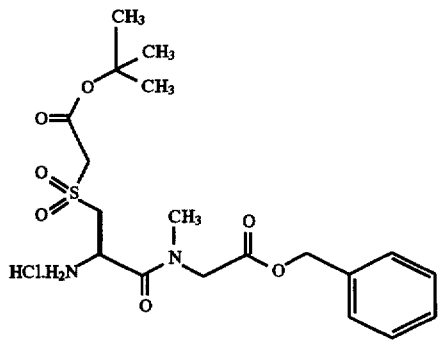

The compound of Example 38 (55.6 g, 111.96 mmole) was dissolved in 580 mL of glacial acetic acid and then sodium perborate tetrahydrate (86.1 g, 559.8 mmole) was added. This mixture was heated to 55° C. After 2.5 hours at this temperature, the reaction mixture was diluted with 1 liter of brine, the aqueous layer was extracted with ethyl acetate (4×250 mL) and the combined organic extracts were dried with anhydrous magnesium sulfate. This solution was filtered and evaporated under vacuum, then repeatedly azeotroped with toluene (200 mL) under vacuum to remove acetic acid. The residual slurry was dissolved in ethyl acetate (200 mL), filtered and the filtrate evaporated to yield 50.6 g (85.5%) of N-Boc-S-(t-butyl acetate)-L-cysteine sulfone sarcosine-O-benzyl ester as a white solid. Thin layer chromatography analysis of the title compound showed a single spot with Rf=0.50 (silica, 3:2 ethyl acetate:hexane).

To a cooled (0° C.) solution of acetyl chloride (48.6 mL, 683 mmole) in dry ethyl acetate (133 mL) was slowly added with stirring dry methanol (27.7 mL, 683 mmole). After 10 minutes, the reaction was allowed to warm to room temperature for 30 minute and then recooled to 0° C. To the reaction mixture was slowly added a solution of N-Boc-S-(t-butyl acetate)-L-cysteine sulfone sarcosine-O-benzyl ester (20.78 g, 42.7 mmole) in dry ethyl acetate (1000 mL). After 4.5 hours at reduced temperature, the reaction was deemed complete by TLC (1:9 methanol:methylene chloride). The reaction was concentrated in vacuo to about 100 mL and the title compound precipitated by pouring into stirring diethyl ether (600 mL). The titled compound was isolated by filtration and dried in vacuo to afford 11.5 g (61% yield) of a white powder.

Example 40

Preparation of N-(D)-camphorsulfonyl-S-(t-butyl acetate)-L-cysteine sulfone sarcosine-O-benzyl ester.

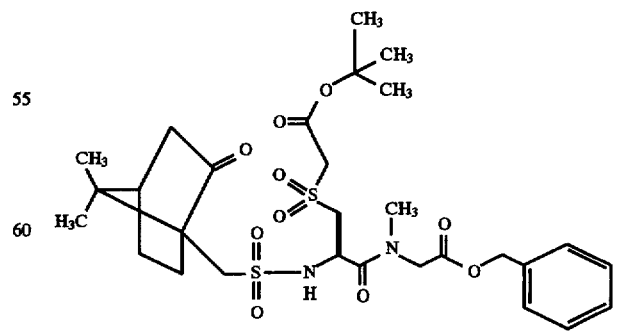

The compound of Example 39 (3.9 g, 9.22 mmole) and (D)-camphorsulfonyl chloride (3.5 g, 13.8 mmole) were dissolved with stirring in 20 mL of dry dimethylformamide and 20 mL of dry tetrahydrofuran. To this mixture was added triethylamine (6.4 mL, 46.1 mmole). After 16 hours, the reaction mixture was diluted with 600 mL of ethyl acetate and washed with 150 mL each of water, 1M aqueous hydrochloric acid, water, saturated aqueous sodium bicarbonate and brine. The organic phase was dried over anhydrous magnesium sulfate, filtered and concentrated in vacuo to afford 3.89 g (70% yield) of the title compound as a yellowish foam. Rf=0.84 (1:9 methanol:dichloromethane).

Example 41

Preparation of N-(D)-camphorsulfonyl-S-(t-butyl acetate)-L-cysteine sulfone sarcosine.

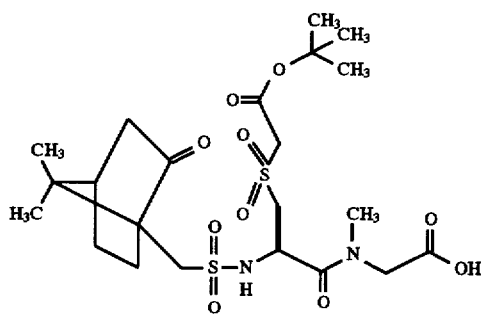

The compound of Example 40 (3.89 g, 6.49 mmole) was dissolved in 300 mL of methanol with stirring and purged with nitrogen. To this mixture was added 2 g of 10% palladium on carbon and stirred vigorously under 1 atmosphere of hydrogen. After 16 hours, the palladium was removed by filtration and the solvent removed in vacuo. The resulting oil was dissolved into 100 mL of ethyl acetate and the product was extracted into 150 mL saturated aqueous sodium bicarbonate. This was washed with 100 mL ethyl acetate and acidified using concentrated hydrochloric acid. The product was then extracted into ethyl acetate (3×200 mL) and the combined organic layers were washed with 200 mL brine and dried over anhydrous magnesium sulfate, filtered and concentrated in vacuo to 1.9 g (57% yield) of the title compound as a white foam.

Example 42

Preparation of (D)-camphorsulfonyl-s-(t-butylacetate) cysteinesulfone sarcosine-N$^g$-NO$_2$-arginine cyclic-OEt aminal.

The compound of Example 4 (1.50 g, 5.59 mmole) and the compound of Example 41 (1.9 g, 3.72 mmole) were dissolved with stirring in 10 mL of dry dimethylformamide and 20 mL of dry tetrahydrofuran. To this mixture was added 1-hydroxybenzotriazole monohydrate (0.76 g, 5.6 mmole) and 2-(1H-benzotriazol-1-yl)-1,1,3,3-tetramethyluronium hexafluorophosphate (2.12 g, 5.6 mmole) followed by N-methylmorpholine (2 mL, 19 mmole). After 16 hours, the reaction mixture was diluted with 600 mL ethyl acetate and extracted with 150 mL each of water, 1M aqueous hydrochloric acid, water, saturated aqueous sodium bicarbonate and brine. The organic phase was dried over anhydrous magnesium sulfate, filtered and the solvent removed in vacuo. Chromatography of the resulting oil (silica, 4:1:4 hexanes:methanol:dichloromethane) afforded 1.16 g (43% yield) of the title compound as an off-white foam. Rf=two spots, 0.40 and 0.47 (1:9 methanol:dichloromethane).

Example 43

Preparation of (D)-camphorsulfonyl cysteinesulfone-s-(t-butylacetate) sarcosine arginine cyclic-OEt aminal

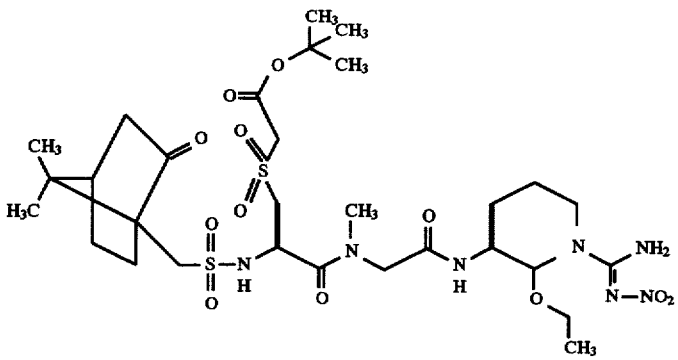

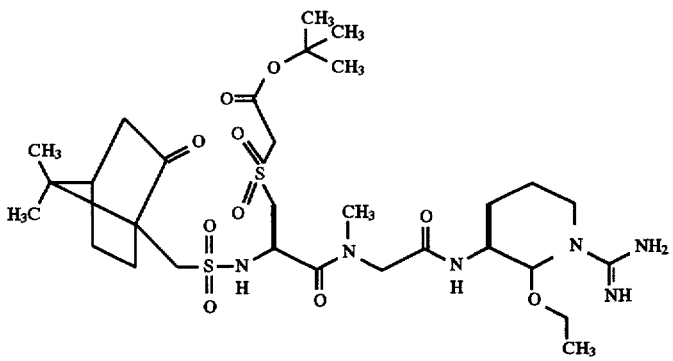

1 g of 10% palladium on carbon was placed in a 500 mL PARR bottle. 10 mL of water and 3 mL of glacial acetic acid was added. To this mixture was added a solution of the compound of Example 42 (1.16 g, 1.6 mmole) in 100 mL of methanol. The mixture was then shaken under a hydrogen atmosphere at 40 psi for 1 day. The catalyst was then removed by filtration and the filtrate concentrated in vacuo. The resulting oil was azeotroped with toluene to remove the remaining acetic acid to afford about 1 g of the title compound.

Example 44

Preparation of (D)-camphorsulfonyl-s-(acetic acid) cysteinesulfone sarcosine arginine aldehyde.

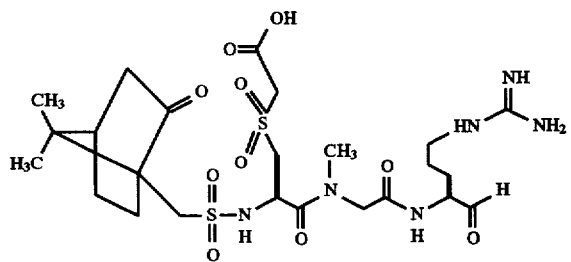

The compound of Example 43 (1 g, 1.6 mmole) was dissolved in 30 mL of 50:50 water:acetonitrile with stirring and cooled to 0° C. in an ice water bath. To this solution was slowly added 50 mL of a 60 wt % solution of hexafluorophosphoric acid in water. After 1 hour, the pH of the reaction mixture was adjusted to about pH 4 using saturated aqueous sodium acetate. This mixture was filtered through a plug of Celite. The title compound was obtained by purification from the filtrate by preparative HPLC (2 inch Vydak C18 column using a gradient consisting of 8–27% acetonitrile in water containing 0.1% trifluoroacetic acid run over 60 minutes at a flowrate of 115 mL/minute) and lyophilization of the pooled fractions. Mass Spec(FAB) confirmed the calculated molecular weight of 635.7.

Example 45

Preparation of benzylsulfonylmethionine(sulfone)methyl ester.

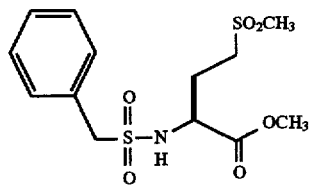

Carbonyldiimidazole (4.9 g, 30 mmole) was added to a suspension of benzylsulfonylmethionine sulfone (8.0 g, 28.5 mmole) in dichloromethane (60 mL) at 0° C. The reaction mixture was allowed to warm to room temperature and was stirred an additional 17 hours. Methanol (2.3 mL, 57 mmole) was added and stirring was continued for 17 hours at which time, the reaction mixture was concentrated under vacuum, and the residue was extracted into ethyl acetate (2×100 mL), washed with 3% hydrochloric acid (aq) (75 mL), brine (75 mL), saturated sodium bicarbonate solution (aq) (75 mL), dried over anhydrous magnesium sulfate, and concentrated under vacuum to yield the title compound as a white foam (6.0 g, 71%). Rf=0.11; 1:1 ethyl acetate:hexanes.

Example 46

Preparation of t-butyl N-cyclohexylglycine.

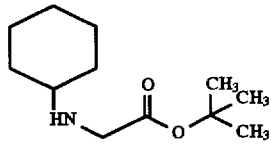

t-Butyl bromoacetate (7.6 mL) was added over 10 minutes to a solution of cyclohexylamine (11.7 mL) in tetrahydrofuran (200 mL) at 0° C. After the addition was complete, the ice-water bath was removed and the reaction was stirred at room temperature for 20 hours. The reaction was filtered through Celite and concentrated under vacuum. The product was purified by flash chromatography on silica gel eluting with a hexane-ethyl acetate (4:1 to 2:1) gradient yielding a clear oil (10.8 g, 99%). Rf=0.22; 1:1 ethyl acetate:hexanes.

Example 47

Preparation of benzylsulfonylmethioninyl(sulfone) N-cyclohexylglycine t-butyl ester.

47

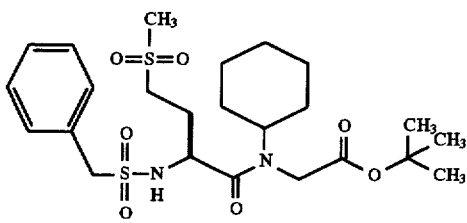

To a solution of the compound of Example 46 (5.0 g, 23.5 mmole) in tetrahydrofuran (40 mL) was added over 15 minutes a 2M solution of trimethylaluminum in toluene (11.5 mL, 23 mmole) at 0° C. After stirring for 1.3 hours, benzylsulfonylmethionine sulfone methyl ester (1.4 g, 4.7 mmole) was added in tetrahydrofuran (10 mL) over 10 minutes. After the reaction mixture warmed to room temperature, it was stirred for 3 days. The reaction mixture was then poured into cold 3% hydrochloric acid (50 mL) and ethyl acetate (50 mL), separated, extracted with ethyl acetate (50 mL), washed with 3% hydrochloric acid (aq) (50 mL), brine (50 mL), dried over anhydrous magnesium sulfate, and concentrated under vacuum. Purification by silica gel chromatography using a dichloromethane, methanol gradient (2–5%) gave the title compound as an orange oil (0.36 g, 16%). Rf=0.91; 9:1 dichloromethane:methanol.

Example 48

Preparation of benzylsulfonylmethioninyl(sulfone)N-cyclohexylglycinyl-$N^g$-nitrocycloarginine ethyl aminal.

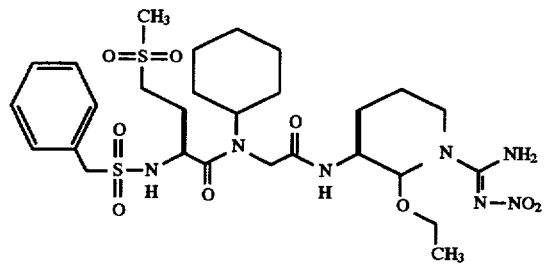

The compound of Example 47 (0.36 g, 0.76 mmole) was stirred with trifluoroacetic acid (5.0 mL) and dichloromethane (5.0 mL) at room temperature for 3.5 hours. Toluene (5.0 mL) was added and the reaction was concentrated under vacuum to give a residue.

The residue was dissolved in acetonitrile (5.0 mL), and the compound of Example 4 (0.223 g, 0.76 mmole), 1-ethyl-3-(3-dimethylamino-propyl)carbodiimide hydrochloride salt (0.18 g, 0.91 mmole), 1-hydroxybenzotriazole monohydrate (0.12 g, 0.91 mmole), and finally N-methylmorpholine (0.25 g, 2.3 mmole) were added. The reaction mixture was stirred at room temperature for 20 hours, then was concentrated under vacuum to give a residue. The residue was then extracted into ethyl acetate (2×50 mL), washed with 3% hydrochloric acid (aq) (50 mL), brine (50 mL) sodium bicarbonate solution (aq) (50 mL), dried over anhydrous magnesium sulfate, and concentrated under vacuum to yield the product as a pale yellow foam (0.30 g, 62%). Rf=0.90; 9:1 dichloromethane:methanol.

Example 49

Preparation of benzylsulfonylmethioninyl(sulfone)N-cyclohexylglycinylcycloarginine ethyl aminal.

48

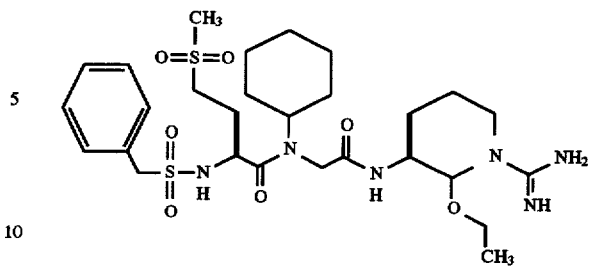

The compound of Example 48 (0.30 g, 0.47 mmole) was dissolved in methanol (12 mL), acetic acid (2.0 mL), and distilled water (2.0 mL) and the solution was placed in a 250 mL Parr bottle. The reaction vessel was purged with argon and then 10% palladium on carbon catalyst (0.15 g) was added. The reaction mixture was shaken under hydrogen (45 psi) for 2.8 days, then was filtered through Celite and concentrated under vacuum to give crude title compound. This was purified by reverse phase HPLC on a two inch Vydak C-18 at 115 mL/minute, gradient 20–50% over 50 minutes and lyophilyzed to give the title compound as a white powder (0.2 g, 74%).

Example 50

Preparation of benzylsulfonylmethioninyl(sulfone)N-cyclohexylglycinylargininal.

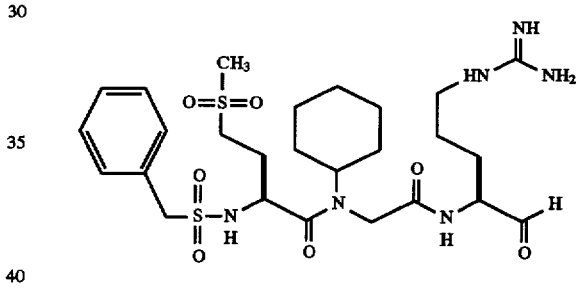

The compound of Example 49 (0.20 g, 0.34 mmole) was dissolved in acetonitrile (3.0 mL), cooled to 0° C. using an ice bath, and 6N hydrochloric acid (8.0 mL) was added. The ice-water bath was removed and the reaction was stirred at room temperature for 3 hours. An additional (1.0 mL) concentrated hydrochloric acid was added. After 1.0 hour, saturated sodium acetate (15 mL) was added. The solution was then filtered and then subjected to purification by HPLC. The product was purified by reverse phase HPLC (2 inch Vydak C-18 at 115 mL/minute, gradient 13–45% acetonitrile in water containing 0.1% trifluoroacetic acid run over 40 minutes) and lyophilyzed to give the title compound as a white powder. Fast atom bombardment mass spectrometry confirmed the theoretical molecular weight of 614 based on formula of $C_{26}H_{42}N_6O_7S_2$.

Example 51

Preparation of other benzylsulfonylmethionyl(sulfone) N-alkylglycinylargininals.

The procedures described in Examples 45 through 50, are used to prepare other preferred compounds of the present invention which are shown below. To prepare these compounds, other substituted amines are used in the place of cyclohexylamine in Example 46. For example, other substituted amines would include cyclohexylmethylamine, 4-hydroxycyclohexylamine, aniline, and benzylamine.

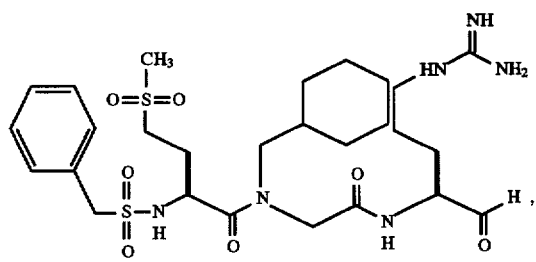

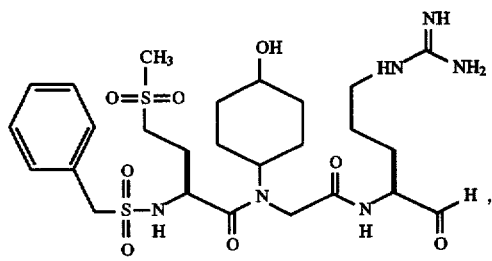

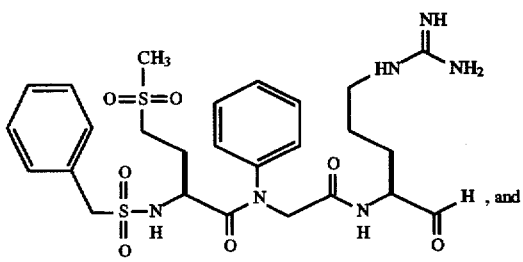

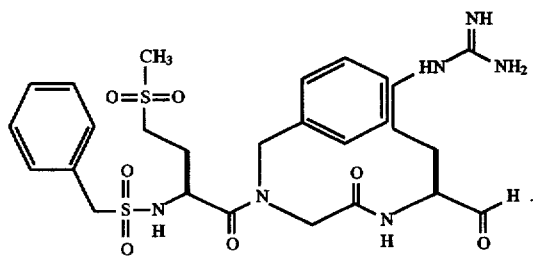

Example 52

Preparation of aspartyl-beta-benzyl ester sarcosine-O-fluorenylmethyl ester, hydrochloride salt.

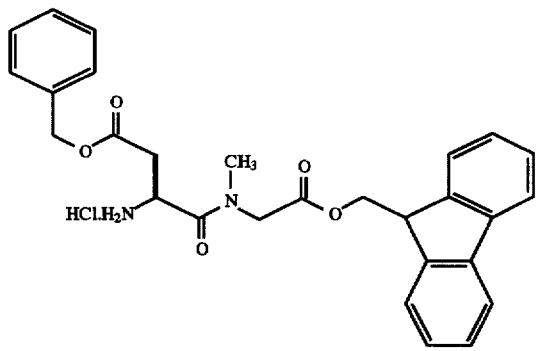

To a stirring solution of sarcosine-O-fluorenylmethyl ester, hydrochloric acid salt (5.6 g, 18.3 mmole) in 90 mL of dry dimethylformamide was added N-Boc-aspartic acid beta-benzyl ester (6.5 g, 20.2 mmole) followed by benzotriazol-1-yl-oxy-tris-(dimethylamino)-phosphonium hexafluorophosphate (8.12 g, 18.4 mmole) and 2,4,6-collidine (5 mL, 36.7 mmole). The reaction mixture was stirred for 16 hours at room temperature, then was dissolved in 800 mL of ethyl acetate and washed with 200 mL each of water, 1M aqueous hydrochloric acid, water, saturated aqueous sodium bicarbonate and brine. The organic phase was dried over anhydrous magnesium sulfate, filtered and the solvent removed in vacuo. Rf=0.85 (1:9 methanol:dichloromethane).

The resulting oil was dissolved in dichloromethane (200 mL) and treated with 50 mL of 4.0M solution of hydrochloric acid in dioxane. After 12 hours, the title compound was precipitated by pouring the reaction mixture into ether (500 mL) with vigorous stirring, filtered and dried in vacuo to provide 8.2 g (86% yield) of the title compound as an off-white powder. Rf=0.5 (1:9 methanol:dichloromethane).

Example 53

Preparation of (D)-camphorsulfonyl aspartyl-beta-benzyl ester sarcosine.

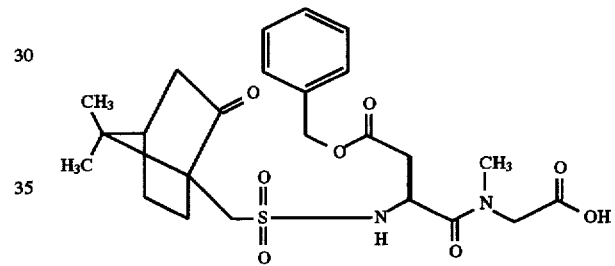

To a solution of the compound of Example 52 (8.2 g, 15.7 mmole) in 30 mL of dry dimethylformamide and 50 mL acetonitrile was added (D)-camphorsulfonyl chloride (5.9 g, 23.6 mmole) followed by diisopropylethylamine (14 mL, 78.7 mmole). The reaction mixture was stirred for 16 hours at room temperature, at which time piperidine (10 mL, 100 mmole) was added to remove the fluorenylmethyl ester. After another 12 hours, the reaction mixture was dissolved in 600 mL of ethyl acetate and extracted in to saturated aqueous bicarbonate (2×200 mL). The combined aqueous fractions were washed with 200 mL ethyl acetate and then acidified to about pH 4 using hydrochloric acid. This was then extracted with ethyl acetate (2×300 mL) and the organic fractions were washed with 300 mL brine, dried over anhydrous magnesium sulfate, filtered and the solvent removed in vacuo to provide 6 g (55% yield) of the title compound as an off-white foam. Rf=0.38 (1:9 methanol:dichloromethane).

Example 54

Preparation of (D) camphorsulfonl aspartyl-beta-benzyl ester sarcosine-$N^g$-$NO_2$-arginine cyclic-OEt aminal.

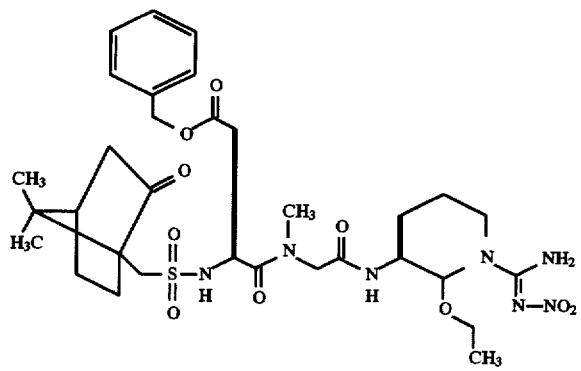

The compound of Example 4 (1.18 g, 4.41 mmole) and the compound of Example 53 (2.1 g, 4.01 mmole) were dissolved with stirring in 10 mL of dry dimethylformamide and 30 mL of dry tetrahydrofuran. To this mixture was added 1-hydroxybenzotriazole monohydrate (0.81 g, 6.02 mmole) and 2-(1H-benzotriazol-1-yl)-1,1,3,3-tetramethyluronium hexafluorophosphate (2.28 g, 6.02 mmole) followed by N-methylmorpholine (2 mL, 20 mmole). After 16 hours, the reaction mixture was diluted with 700 mL ethyl acetate and extracted with 150 mL each of water, 1M aqueous hydrochloric acid, water, saturated aqueous sodium bicarbonate and brine. The organic phase was dried over anhydrous magnesium sulfate, filtered and the solvent removed in vacuo to afford 2.65 g (91% yield) of the title compound as an off-white foam. Rf=two spots, 0.43 and 0.54 (1:9 methanol:dichloromethane).

Example 55

Preparation of (D)-camphorsulfonyl aspartyl sarcosine-arginine cyclic-OEt aminal.

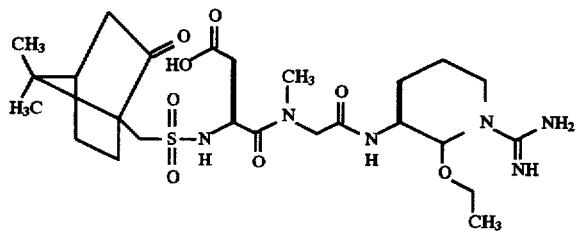

1 g of 10% palladium on carbon was placed in a 500 mL PARR bottle. 10 mL of water and 7 mL of glacial acetic acid was added. To this mixture was added a solution of the compound of Example 54 (2.6 g, 3.5 mmole) in 100 mL of methanol. The mixture was then shaken under a hydrogen atmosphere at 40 psi for 1 day. The catalyst was then removed by filtration and the filtrate concentrated in vacuo. The resulting oil was azeotroped with toluene to remove the remaining acetic acid to afford about 2 g of the title compound which was purified by HPLC on a two inch Vydak C-18 column at 115 mL/minute, gradient 20–60% over 50 minutes to give 0.7 g (30% yield) of the title compound as a white powder.

Example 56

Preparation of (D)-camphorsulfonyl aspartyl sarcosine arginine aldehyde.

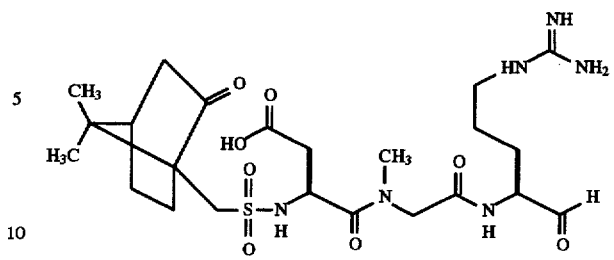

The compound of Example 55 (0.7 g, 1.2 mmole) was dissolved in 20 mL of 50:50 water:acetonitrile with stirring and cooled to 0° C. in an ice water bath. To this solution was slowly added 40 mL of a 60 wt % solution of hexafluorophosphoric acid in water. After 1.5 hour, the pH of the reaction mixture was adjusted to about pH 4 using saturated aqueous sodium acetate. This mixture was filtered through a plug of Celite. The title compound was obtained by purification from the filtrate by preparative HPLC (2 inch Vydak C18 column using a gradient consisting of 8–25% acetonitrile in water containing 0.1% trifluoroacetic acid run over 55 minutes at a flowrate of 115 mL/minute) and lyophilization of the pooled fractions. Mass Spec(FAB) confirmed the theoretical molecular weight of 557.6.

Example 57

Preparation of 3-(3-pyridyl)-alanine sarcosine benzyl ester hydrochloride salt.

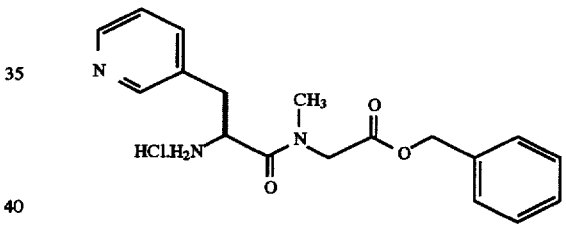

To a stirring solution of Boc-3-(3-pyridyl)-L-alanine (10 g, 37.5 mmole) in 190 mL of dry dimethylformamide was added sarcosine-O-benzyl ester, p-toluenesulfonic acid salt (13.2 g, 37.5 mmole) followed by benzotriazol-1-yl-oxy-tris-(dimethylamino)-phosphonium hexafluorophosphate (16.6 g, 37.5 mmole) and N-methylmorpholine (21 mL, 187.7 mmole). The mixture was stirred for 16 hours at room temperature. The reaction mixture was dissolved in 1000 mL of ethyl acetate and washed with 200 mL each of water, 1M aqueous hydrochloric acid, water, saturated aqueous sodium bicarbonate and brine. The organic phase was dried over anhydrous magnesium sulfate, filtered and the solvent removed in vacuo to give an oil. Rf=0.57 (1:9 methanol:dichloromethane).

The oil was dissolved in dichloromethane (250 mL) and treated with 50 mL of 4.0M solution of hydrochloric acid in dioxane. After 12 hours, the title compound was precipitated by pouring the reaction mixture into ether (500 mL) with vigorous stirring, filtered and dried in vacuo to provide 5.78 g (42% yield) of the title compound as an off-white powder.

Example 58

Preparation of (D)-camphorsulfonyl-3-(3-pyridyl)-alanine sarcosine benzyl ester.

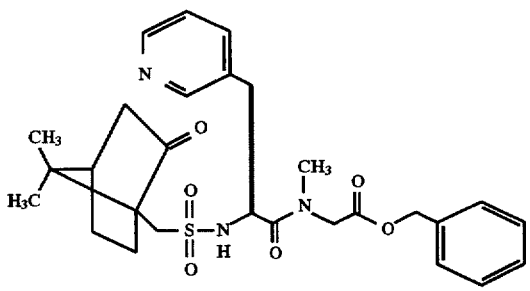

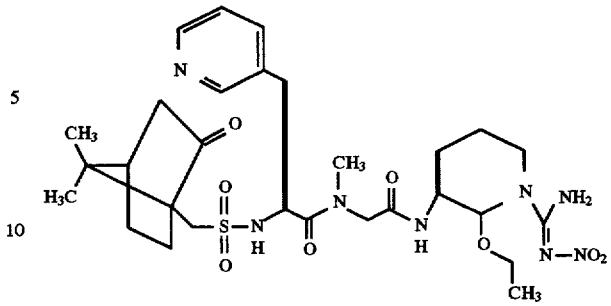

To a solution of the compound of Example 57 (3.3 g, 9.07 mmole) in 20 mL of dry dimethylformamide and 25 mL acetonitrile was added (D)-camphorsulfonyl chloride (3.4 g, 13.6 mmole) followed by triethylamine (6 mL, 45 mmole). The reaction mixture was stirred for 16 hours at room temperature. The reaction mixture was dissolved in 700 mL of ethyl acetate and washed with 100 mL each of water, saturated aqueous sodium bicarbonate and brine. The organic phase was dried over anhydrous magnesium sulfate, filtered and the solvent removed in vacuo to give an oil. The oil was dissolved in dichloromethane and filtered through silica, eluting first with dichloromethane (500 mL) then 1:9 methanol:dichloromethane (1000 mL). The methanol:dichloromethane fraction was concentrated to provide 3.33 g (68% yield) of the title compound as a brownish-yellow foam. Rf=0.52 (1:9 methanol:dichloromethane).

The compound of Example 4 (1.54 g, 5.76 mmole) and the compound of Example 59 (2 g, 4.4 mmole) were dissolved with stirring in 10 mL of dry dimethylformamide and 10 mL of dry acetonitrile. To this mixture was added 1-ethyl-3-(3-dimethylamino-propyl)carbodiimide hydrochloride salt (1.3 g, 6.6 mmole) and 1-hydroxybenzotriazole monohydrate (0.9 g, 6.6 mmole) followed by diisopropylethylamine (3 mL, 22 mmole). After 16 hours, the reaction mixture was concentrated in vacuo and then diluted with 500 mL ethyl acetate and extracted with 100 mL each of water, saturated aqueous sodium bicarbonate and brine. The organic phase was dried over anhydrous magnesium sulfate, filtered and the solvent removed in vacuo to afford 2.07 g (70% yield) of the title compound as an off-white foam. Rf=two spots, 0.35 and 0.40 (1:9 methanol:dichloromethane).

Example 59

Preparation of (D)-camphorsulfonyl-3-(3-pyridyl)-alanine sarcosine.

Example 61

Preparation of (D)-camphorsulfonyl-3-(3-pyridyl)-alanine sarcosine arginine cyclic-OEt aminal.

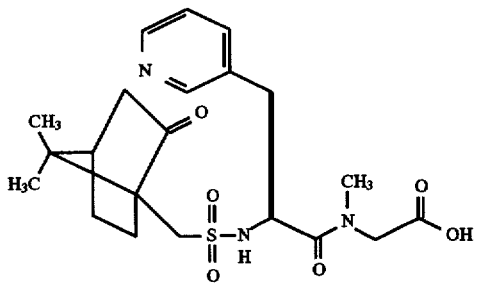

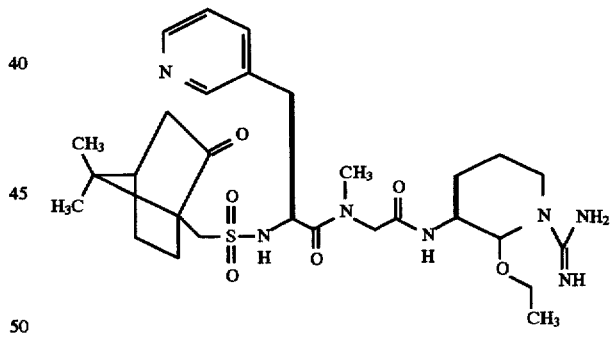

To a solution of the compound of Example 58 (3.33 g, 6.15 mmole) in 200 mL of methanol under a nitrogen blanket, was added 10% palladium on carbon (2.5 g) and the mixture was hydrogenated at 1 atmosphere for 4 days. The catalyst was removed and replaced 2× during the course of the reaction. The mixture was then filtered and concentrated in vacuo to provide 2.0 g (72% yield) of the title compound as a white foam.

Example 60

Preparation of (D)-camphorsulfonyl-3-(3-pyridyl)-alanine sarcosine-N$^g$-NO$_2$-arginine cyclic-OEt aminal.

2 g of 10% palladium on carbon was placed in a 500 mL PARR bottle. 10 mL of water and 6 mL of glacial acetic acid was added. To this mixture was added a solution of the compound of Example 60 (2.07 g, 3.11 mmole) in 100 mL of methanol. The mixture was then shaken under a hydrogen atmosphere at 40 psi for 3 days. The catalyst was then removed by filtration and the filtrate concentrated in vacuo to give an oil. The oil was azeotroped with toluene to remove the remaining acetic acid to affor about 1.9 g (quantitive yield) of the title compound.

Example 62

Preparation of (D)-camphorsulfonyl-3-(3-pyridyl)-alanine sarcosine arginine aldehyde.

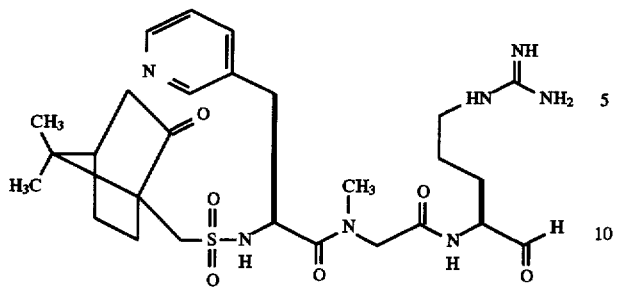

The compound of Example 61 (1.9 g, 3.1 mole) was dissolved in 30 mL of 50:50 water:acetonitrile with stirring and cooled to 0° C. in an ice water bath. To this solution was slowly added 40 mL of a 60 wt % solution of hexafluorophosphoric acid in water. After 2 hour, the pH of the reaction mixture was adjusted to about pH 4 using saturated aqueous sodium acetate. This mixture was filtered through a plug of Celite. The title compound was obtained by purification from the filtrate by preparative HPLC (2 inch Vydak C18 column using a gradient consisting of 8–25% acetonitrile in water containing 0.1% trifluoroacetic acid run over 55 minutes at a flowrate of 115 mL/minute) and lyophilization of the pooled fractions. Mass Spec(FAB) confirmed the theoretical molecular weight of 591.7.

Example 63

Preparation of benzylsulfonyl-3-(3-pyridyl)-alanine sarcosine benzyl ester.

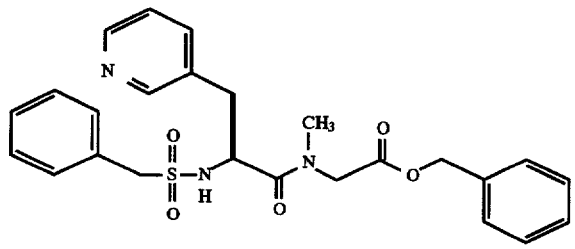

The title compound was prepared under the same manner as described in Example 58, using 2.44 g (6.7 mmole) of the compound of Example 57 in 10 mL of dry dimethylformamide and 25 mL acetonitrile, alphatoluenesulfonyl chloride (1.9 g, 10.1 mmole), and triethylamine (5 mL, 34 mmole). This afforded 0.86 g (27% yield) of the title compound as a brownish-yellow foam. Rf=0.45 (1:9 methanol:dichloromethane).

Example 64

Preparation of benzylsulfonyl-3-(3-pyridyl)-alanine sarcosine.

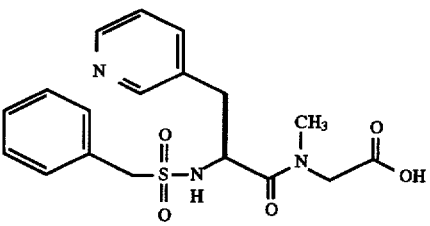

The title compound was prepared in the same manner as described in Example 59 using the compound of Example 63 (0.86 g, 1.78 mmole) in 100 mL of methanol and 0.5 g 10% palladium on carbon to provide 0.37 g (53% yield) of the title compound as a white foam.

Example 65

Preparation of benzylfonyl-3-(3-pyridyl)-alanine sarcosine $N^g$-$NO_2$-arginine cyclic-OEt aminal.

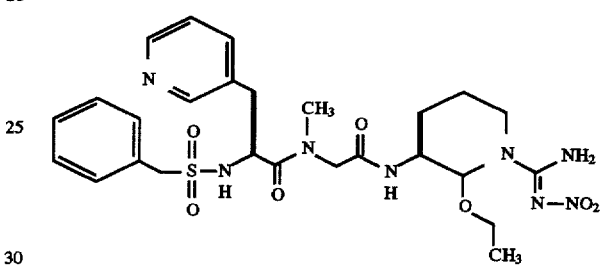

The title compound was prepared in the same manner as described in Example 60 using the compound of Example 4 (0.33 g, 1.23 mmole), the compound of Example 64 (0.37 g, 0.95 mmole), 5 mL of dry dimethylformamide and 5 mL of dry acetonitrile, 1-ethyl-3-(3-dimethylaminopropyl) carbodiimide hydrochloride salt (0.27 g, 1.4 mmole) and 1-hydroxybenzotriazole monohydrate (0.2 g, 1.4 mmole) and diisopropylethylamine (1 mL, 1.3 mmole) to afford 0.32 g (70% yield) of the title compound as an off-white foam. Rf=two spots, 0.30 and 0.35 (1:9 methanol:dichloromethane).

Example 66

Preparation of benzylsulfonyl-3-(3-pyridyl)-alanine sarcosine arginine cyclic-OEt aminal.

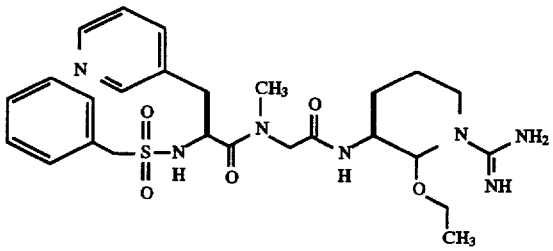

The title compound was prepared in the same manner as described in Example 61 using 0.3 g of 10% palladium on carbon, 5 mL of water, 1 mL of glacial acetic acid, the compound of Example 65 (0.32 g, 0.53 mmole) in 30 mL of methanol to afford about 0.3 g (quantitative yield) of the title compound.

Example 67

Preparation of benzylsulfonyl-3-(3-pyridyl)-alanine sarcosine arginine aldehyde.

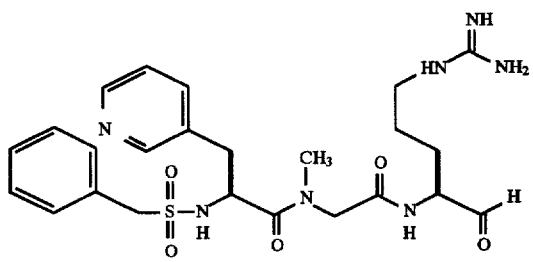

The title compound was prepared in the same manner as in Example 62 using the compound of Example 66 (0.29 g, 0.5 mmole), 10 mL of 50:50 water:acetonitrile and 20 mL of a 60 wt % solution of hexafluorophosphoric acid in water. After 4 hours, the pH of the reaction mixture was adjusted to about pH 4 using saturated aqueous sodium acetate. This mixture was filtered thru a plug of Celite. The title compound was obtained by purification from the filtrate by preparative HPLC (2 inch Vydak C18 column using a gradient consisting of 5–15% acetonitrile in water containing 0.1% trifluoroacetic acid run over 60 minutes at a flowrate of 115 mL/minute) and lyophilization of the pooled fractions. Mass Spec(FAB) confirmed the theoretical molecular weight of 531.6.

Example 68

Preparation of glycine sarcosine benzyl ester hydrochloride salt.

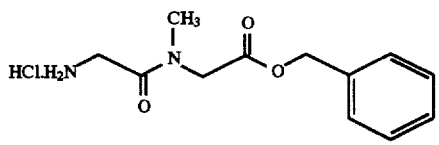

To a stirring solution of Boc-glycine (5.7 g, 32.5 mole) in 160 mL of dry dimethylformamide was added sarcosine benzyl ester p-toluenesulfonic acid salt (17.1 g, 48.8 mole) followed by benzotriazol-1-yl-oxy-tris-(dimethylamino)-phosphonium hexafluorophosphate (14.4 g, 32.5 mole) and N-methylmorpholine (18 mL, 162.7 mmole). The reaction mixture was stirred for 16 hours at room temperature. The reaction mixture was dissolved in 1000 mL of ethyl acetate and washed with 300 mL each of water, 1M aqueous hydrochloric acid, water, saturated aqueous sodium bicarbonate and brine. The organic phase was dried over anhydrous magnesium sulfate, filtered and the solvent removed in vacuo. Rf=0.78 (1:9 methanol: dichloromethane).

The resulting oil was dissolved in dichloromethane (100 mL) and then treated with 50 mL of 4.0M solution of hydrochloric acid in dioxane. After 5 hours, 8.8 g (quantitative yield) title compound was isolated as a off-white foam by removing the solvent in vacuo and azeotroping with toluene.

Example 69

Preparation of (D)-camphorsulfonyl-glycine sarcosine benzyl ester.

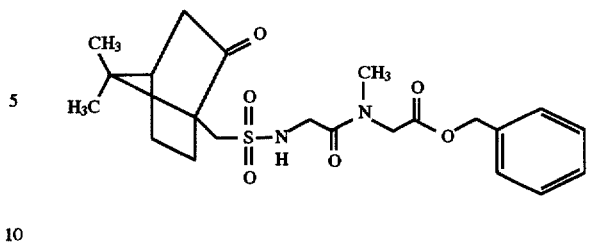

To a solution of the compound of Example 68 (8.8 g, 32.3 mmole) in 20 mL of dry dimethylformamide and 150 mL tetrahydrofuran was added (D)-camphorsulfonyl chloride (12.1 g, 48.4 mmole) followed by triethylamine (22 mL, 161 mmole). The mixture was stirred for 16 hours at room temperature. The reaction mixture was dissolved in 1000 mL of ethyl acetate and washed with 300 mL each of water, 1M aqueous hydrochloric acid, water, saturated aqueous sodium bicarbonate and brine. The organic phase was dried over anhydrous magnesium sulfate, filtered and the solvent removed in vacuo to give an oil. The oil was dissolved in dichloromethane and filtered through silica, eluting first with dichloromethane (500 mL) then 1:9 methanol:dichloromethane (1000 mL). The methanol:dichloromethane fraction was concentrated to provide 13.37 g (91% yield) of the title compound as an off-white foam. Rf=0.77 (1:9 methanol:dichloromethane).

Example 70

Preparation of (D)-camphorsulfonyl-glycine sarcosine.

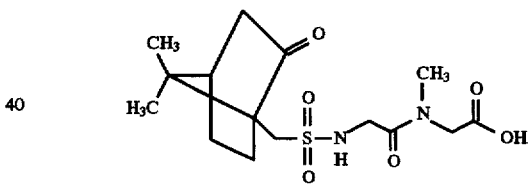

To a solution of the compound of Example 69 (13 g, 28.9 mmole) in 600 mL of methanol under a nitrogen blanket, was added 10% palladium on carbon (5 g) and the mixture was hydrogenated at 1 atmosphere for 16 hours. The mixture was then filtered and concentrated in vacuo to give an oil. The oil was dissolved in 400 mL saturated aqueous sodium bicarbonate and washed with 300 mL ethyl acetate. The aqueous fraction was then acidified using hydrochloric acid to about pH 4 and extracted with ethyl acetate (2×500 mL). The combined organic fractions were washed with brine (2×300 mL), dried over anhydrous magnesium sulfate, filtered and concentrated in vacuo to provide 2.12 g (21% yield) of the title compound as a white foam. Rf=0.31 (1:9 methanol:dichloromethane).

Example 71

Preparation of (D)-camphorsulfonyl-glycine sarcosine-$N^g$-$NO_2$-arginine cyclic-OEt aminal.

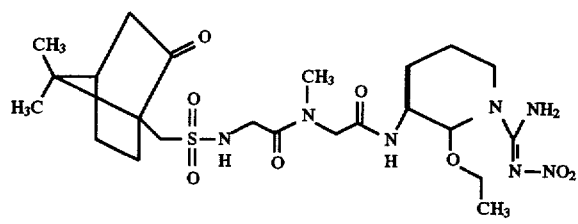

The compound of Example 4 (2.37 g, 8.85 mmole) and the the compound of Example 70 (2.12 g, 5.90 mmole) were dissolved with stirring in 8 mL of dry dimethylformamide and 20 mL of dry acetonitrile. To this mixture was added 1-hydroxy-7-azabenzotriazole (0.4 g, 2.95 mmole) and O-(7-azabenzotriazol-1-yl)-1,1,3,3-tetramethyluronium hexafluorophosphate (2.2 g, 5.9 mmole) followed by N-methylmorpholine (3 mL, 29.5 mmole). After 16 hours, the reaction mixture was concentrated in vacuo and then diluted with 600 mL ethyl acetate and extracted with 200 mL each of water, 1M aqueous hydrochloric acid, water, saturated aqueous sodium bicarbonate and brine. The organic phase was dried over anhydrous magnesium sulfate, filtered and the solvent removed in vacuo to give an oil. Chromatography of the oil on silica gel (eluting with 4:1:4 hexanes-:methanol: dichloromethane) afforded 2.0 g (59% yield) of the title compound as an off-white foam. Rf=two spots 0.36 and 0.44 (1:9 methanol:dichloromethane).

Example 72

Preparation of (D)-camphorsulfonyl-glycine-sarcosine-arginine cyclic-OEt aminal.

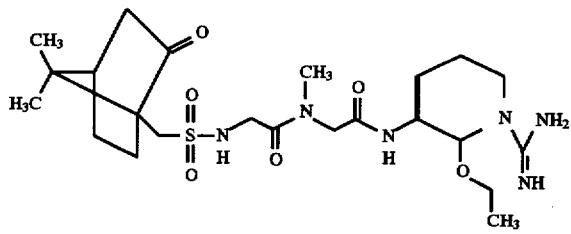

1 g of 10% palladium on carbon was placed in a 500 mL PARR bottle. 10 mL of water and 7 mL of glacial acetic acid was added. To this mixture was added a solution of the compound of Example 71 (2 g, 3.48 mmole) in 100 mL of methanol. The mixture was then shaken under a hydrogen atmosphere at 40 psi for 1 day. The catalyst was removed by filtration and the filtrate concentrated in vacuo to give an oil. 0.57 g (31% yield) title compound was obtained from this oil by purification by preparative HPLC (2 inch Vydak C18 column using a gradient consisting of 10–30% acetonitrile in water containing 0.1% trifluoroacetic acid run over 55 minutes at a flowrate of 115 mL/minute).

Example 73

Preparation of (D)-camphorsulfonyl-glycine-sarcosine-arginine aldehyde.

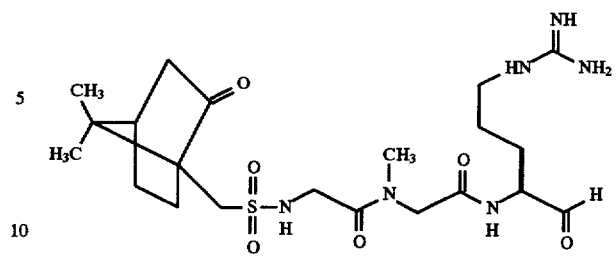

The compound of Example 72 (0.57 g, 1.08 mmole) was dissolved in 20 mL of 50:50 water:acetonitrile with stirring and cooled to 0° C. in an ice water bath. To this solution was slowly added 30 mL of a 60 wt % solution of hexafluorophosphoric acid in water. After 1 hour, the pH of the reaction mixture was adjusted to about pH 4 using saturated aqueous sodium acetate. This mixture was filtered thru a plug of Celite. The title compound was obtained by purification from the filtrate by preparative HPLC (2 inch Vydak C18 column using a gradient consisting of 7–27% acetonitrile in water containing 0.1% trifluoroacetic acid run over 60 minutes at a flowrate of 115 mL/minute) and lyophilization of the pooled fractions. Mass Spec(FAB) confirmed the theoretical molecular weight of 500.6.

Example 74a

Preparation of N-Boc-L-methionine sulfone-O-benzyl ester

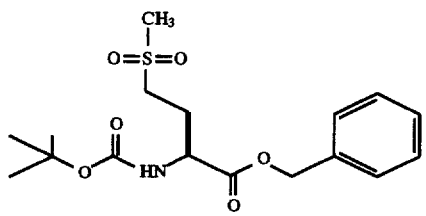

To a solution of N-Boc-L-methionine sulfone (50 g, 178 mmole) in dry THF (500 mL) which had been chilled to 0° C., carbonyl diimidazole (34.6 g, 214 mmole) was added in small portions. After 30 minutes, the mixture was warmed to room temperature for 2 hours until all of the CO2 evolution ceased. After this time, benzyl alcohol (27.6 mL, 267 mmole) was added and the reaction stirred for 12 hours.

The reaction mixture was then reduced in volume under vacuum and the resulting residue was diluted with ethyl acetate (500 mL). The organic phase was then washed with saturated bicarbonate (1×100 mL), brine (100 mL), then saturated aqueous citric acid (1×100 mL), dried over MgSO$_4$, filtered and the solvent removed under vacuum to provide a white solid. The white solid was washed with a 1:1 mixture of diethyl ether/hexanes (300 mL) and filtered off on a Büchner funnel to provide 50.0g (92%) of the title compound. Thin layer chromatography analysis of the title compound showed a single spot with Rf=0.18 (silica, 3:2 hexanes/ethyl acetate).

Example 74b

Preparation of N-Boc-N-phenethyl-L-methionine sulfone sarcosine benzyl ester.

To a solution of N-Boc-L-methionine sulfone sarcosine benzyl ester, Example 74a, (4.7 g, 10.0 mole) in dry N,N-dimethyl formamide (20 mL) at 0° C. was added (2-iodoethyl)benzene (2.9 mL, 20.0 mole) followed by sodium hydride (60% dispersion, 400 mg, 10.0 mole). The reaction is allowed to warm to room temperature and stirred for 24 hours. The reaction is diluted with ethyl acetate (200 mL) and washed successively with saturated sodium bicarbonate (1×75 mL), brine (1×75 mL) and 1M aqueous hydrochloric acid (1×75 mL). The organic phase is dried over $MgSO_4$, filtered and the solvent removed in vacuo to provide the crude alkylated material. This material is purified on a flush silica gel column to give purified material.

Example 75

Preparation of N-Boc-N-phenethyl-L-methionine sulfone sarcosine acid.

To a solution of Example 74 (5.7 g, 10.0 mole) in methanol (200 mL) was added 1.0 g 10% palladium on carbon and the reaction subjected to atmospheric hydrogenation for 24 hours. The reaction mixture was then filtered through a short plug of celite and the reaction volume reduced in vacuo to provide the desired acid.

Example 76

Preparation of N-Boc-N-phenethyl-L-methionine sulfone sarcosine cyclic nitro arginine ethyl aminal.

To a solution of Example 75 (4.8 g, 10.0 mmole) in N,N-dimethyl formamide (25 mL) was added 1-ethyl-3-(3-dimethylaminopropyl)carbodiimide hydrochloride salt (1.9 g, 10.0 mmole) followed by 1-hydroxybenzotriazole (2.3 g, 15.0 mmole) and the reaction stirred for 30 minutes. Then cyclic nitro arginine ethyl aminal hydrochloride (4.0 g, 15 mmole) was added followed by N-methyl morpholine (2.2 ml, 20.0 mmole). The reaction is then stirred at room temperature for 18 hours. The reaction is diluted with ethyl acetate (300 mL) and washed successively with saturated sodium bicarbonate (1×100 mL), brine (1×100 mL) and 1M aqueous hydrochloric acid (1×100 mL). The organic phase was dried over $MgSO_4$, filtered and the solvent removed in vacuo to provide the desired coupled product.

Example 77

Preparation of N-Boc-N-phenethyl-L-methionine sulfone sarcosine cyclic arginine ethyl aminal acetate salt.

To a solution of Example 76 (6.9 g, 10.0 mmole) in water (60 mL), acetic acid (20 mL) and methanol (600 mL) in a 2000 mL Parr bottle was added 5.0 g of 10% palladium on carbon. The mixture was then shaken under a hydrogen atmosphere of 40 psi for 3 days. The catalyst was then removed by filtration and the filtrate concentrated in vacuo. The product was azeotroped with toluene to remove residual acetic acid to afford the title compound.

Example 78

Preparation of N-phenethyl-L-methionine sulfone sarcosine argininal bistrifluoroacetate salt.

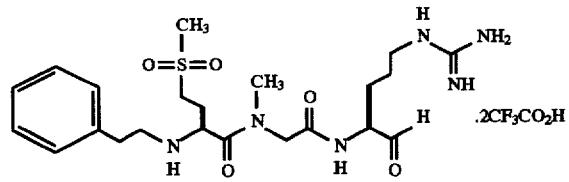

The compound of Example 77 (6.4 g, 10.0 mmole) was dissolved in 200 mL of 1:1 water:acetonitrile with stirring and cooled to 0° C. in an ice water bath. To this solution was slowly added 300 mL of a 60 wt % solution of hexafluorophosphoric acid in water. After 1 hour analytical HPLC (20–60% acetonitrile/water containing 0.1% trifluoroacetic acid) indicated complete hydrolysis of the starting compound. The pH of the reaction mixture was adjusted to pH=4 using 3.0M aqueous sodium acetate. This mixture was filtered through a short plug of celite and was then purified by preparative HPLC to provide the title compound.

Example 79

Preparation of N-Boc-L-Glutamate-(beta-3-(S)-amino quinuclidinyl)-alpha benzyl ester.

To a solution of N-Boc-L-glutamic acid-(beta-acid)-benzyl ester (3.3 g, 10.0 mmole) in N,N-dimethyl formamide (50 mL) was added 1-hydroxy-7-azabenzotriazole (2.0 g, 15.0 mmole) and O-(7-azabenzotriazol-1-yl)-1,1,3,3,-tetramethylaronium hexafluorophosphate (3.8 g, 10.0 mmole) and the reaction stirred at room temperature for 30 minutes. Then 3-(R)-aminoquinuclidine dihydrochloride (3.0 g, 15.0 mmole) was added followed by N,N-diisopropylethyl amine (10.5 mL, 60.0 mmole) and the reaction stirred at room temperature for 18 hours. The reaction mixture was diluted with ethyl acetate (500 mL) and washed successively with saturated sodium bicarbonate (2×100 mL), water (2×100 mL) and brine (2×100 mL). The organic phase was dried over $MgSO_4$, filtered and the solvent removed in vacuo to provide the title compound.

Example 80

Preparation of N-benzylsulfonyl-L-glutamate (beta-3(S)-amino quinuclidinyl)-alpha benzyl ester.

A solution of Example 79 (4.5 g, 10.0 mole) in dry ethyl acetate (100 mL) was added 4M hydrochloric acid in dry dioxane (100 mL) at room temperature. The mixture was stirred for 3 hours and then evaporated in vacuo to provide the crude dihydrochloride salt. This compound was then dissolved in dry N,N-dimethyl formamide (50 mL) and benzylsulfonyl chloride (2.1 g, 12.0 mole) was added followed by triethylamine (7.0 mL, 50.0 mole). The reaction mixture was stirred at room temperature for 15 hours and then the reaction was diluted with ethyl acetate (400 mL). The organic phase was washed successively with saturated aqueous sodium bicarbonate (2×100 mL), water (2×100 mL) then brine (2×100 mL). The organic phase was dried over $MgSO_4$, filtered and the solvent removed in vacuo to provide the title compound.

Example 81

Preparation of N-benzylsulfonyl-L-glutamic alpha acid-(beta-3(S)-amino quinuclidinyl).

To a solution of Example 80 (4.0 g, 10.0 mole) in methanol (200 mL) was added 1.0 g of 10% palladium on carbon and the suspension subjected to atmospheric hydrogenation for 10 hours. The reaction was filtered through a short plug of celite and the solvent was removed in vacuo to provide the title compound as the free acid.

Example 82

Preparation of N-benzylsulfonyl-L-glutamate-(beta-3(S)-amino quinuclidinyl)-sarcosine benzyl ester.

To a solution of Example 81 (3.1 g, 10.0 mmole) in N,N-dimethyl formamide (40 mL) was added 1-ethyl-3-(3-dimethylaminopropyl)carbodiimide hydrochloride salt (2.1 g, 11.0 mmole) and 1-hydroxybenzotriazole (2.3 g, 15.0 mmole). The mixture was stirred for 15 minutes at room temperature then sarcosine benzyl ester p-toluenesulfonate salt (3.5 g, 10.0 mmole) was added followed by N-methyl morpholine (2.2 mL, 20.0 mmole). The reaction was stirred for 15 hours then diluted with ethyl acetate (300 mL) and washed successively with saturated sodium bicarbonate (2×100 mL), water (2×100 mL) and brine (2×100 mL). The organic phase was dried over MgSO$_4$, filtered and the solvent removed in vacuo to provide the title compound.

Example 83

Preparation of N-benzylsulfonyl-L-glutamate-(beta-3(S)-amino quinuclidinyl)-sarcosine acid.

To a solution of Example 82 (4.7 g, 10.0 mmole) in methanol (200 mL) was added 1.0 g 10% palladium on carbon and the reaction was subjected to atmospheric hydrogenation for 12 hours. The reaction was filtered through a short plug of celite and the solvent was removed in vacuo to provide the desired title compound.

Example 84

Preparation of N-benzylsulfonyl-L-glutamate-(beta-3(S)-amino quinuclidinyl)-sarcosine-cyclic nitro arginine ethyl aminal.

The compound of Example 83 (3.8 g, 10.0 mmole) was dissolved in N,N-dimethyl formamide (30 mL) and 2-(1H-benzotriazol-1-yl)-1,1,3,3-tetramethyluronium hexafluorophosphate (4.2 g, 11.0 mmole) was added followed by 1-hydroxybenzotriazole monohydrate (2.3 g, 15.0 mmole). The reaction was stirred for 15 minutes then the cyclic nitro arginine ethyl aminal hydrochloride salt (3.7 g, 10.0 mmole) was added followed by N-methyl morpholine (2.2 mL, 20.0 mmole) and the reaction stirred for 12 hours. The reaction mixture was diluted with ethyl acetate (300 mL) and washed successively with saturated sodium bicarbonate (2×100 mL), water (2×100 mL) and brine (2×100 mL). The organic phase was dried over MgSO$_4$, filtered and the solvent removed in vacuo to provide the crude title compound.

Example 85

Preparation of N-benzylsulfonyl-L-glutamate-(beta-3(S)-amino quinuclidinyl-N'-(3-(1-propenyl))iodide)-sarcosine-cyclic nitro arginine ethyl aminal.

To a solution of Example 84 (7.0 g, 10.0 mmole) in acetonitrile (25 mL) was added allyl iodide (1.8 mL, 20.0 mmole) and the reaction stirred at room temperature for 15 hours. The reaction was diluted with ethyl ether (250 mL) and the precipitate obtained was filtered off and dried in vacuo to provide the title compound.

Example 86

Preparation of N-benzylsulfonyl-L-glutamate-(beta-3(S)-amino quinuclidinyl-N'-propyl iodide salt)-sarcosine-cyclic arginine ethyl aminal.

To a solution of Example 85 (8.6 g, 10.0 mmole) in water (60 mL), acetic acid (20 mL) and methanol (600 mL) in a 2000 mL Parr bottle was added 5.0 g of 10% palladium on carbon. The mixture was then shaken under a hydrogen atmosphere of 40 psi for 3 days. The catalyst was then removed by filtration and the filtrate concentrated in vacuo. The product was azeotroped with toluene to remove residual acetic acid to afford the title compound.

Example 87

Preparation of N-benzylsulfonyl-L-glutamate-(beta-3(S)-amino quinuclidinyl-N'-propyl iodide salt)-sarcosine-argininal.

The compound of Example 86 (8.1 g, 10.0 mmole) was dissolved in 200 mL of 1:1 water:acetonitrile with stirring and cooled to 0° C. in an ice water bath. To this solution was slowly added 300 mL of a 60 wt % solution of hexafluorophosphoric acid in water. After 1 hour analytical HPLC (20–60% acetonitrile/water containing 0.1% trifluoroacetic acid) indicated complete hydrolysis of the starting compound. The pH of the reaction mixture was adjusted to pH=4 using 3.0M aqueous sodium acetate. This mixture was filtered through a short plug of celite and was then purified by preparative HPLC to provide the title compound.

Example 88

Preparation of N-benzylsulfonyl-L-glutamate-(beta-3(S)-amino quinuclidinyl)-sarcosine-cyclic arginine ethyl aminal.

To a solution of Example 87 (6.9 g, 10.0 mmole) in water (60 mL), acetic acid (20 mL) and methanol (600 mL) in a 2000 mL Parr bottle was added 5.0 g of 10% palladium on carbon. The mixture was then shaken under a hydrogen atmosphere of 40 psi for 3 days. The catalyst was then removed by filtration and the filtrate concentrated in vacuo. The product was azeotroped with toluene to remove residual acetic acid to afford the title compound.

Example 89

Preparation of N-benzylsulfonyl-L-glutamate-(beta-3(S)-amino quinuclidinyl)-sarcosine argininal.

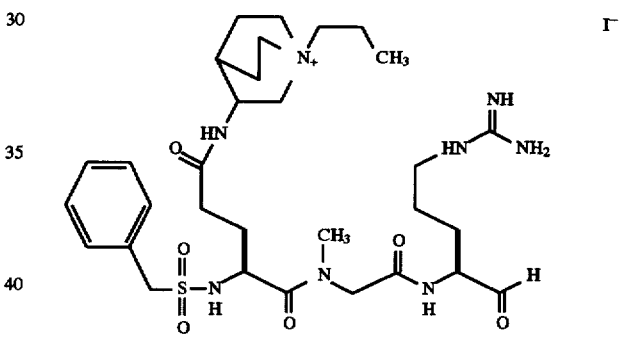

The compound of Example 88 (6.4 g, 10.0 mmole) was dissolved in 200 mL of 1:1 water:acetonitrile with stirring and cooled to 0° C. in an ice water bath. To this solution was slowly added 300 mL of a 60 wt % solution of hexafluorophosphoric acid in water. After 1 hour analytical HPLC (20–60% acetonitrile/water containing 0.1% trifluoroacetic acid) indicated complete hydrolysis of the starting compound. The pH of the reaction mixture was adjusted to pH=4 using 3.0M aqueous sodium acetate. This mixture was filtered through a short plug of celite and was then purified by preparative HPLC to provide the title compound.

Example 90

Preparation of N-benzylsulfonyl-S-(t-butylacetate)-L-cysteine sulfone-sarcosine-benzyl ester.

A solution of the compound of Example 39 (5.0 g, 9.7 mmole) in 100 mL of sieve dried ethyl acetate was prepared. To this, 26 mL of 5.7M anhydrous hydrochloric acid/ethyl acetate (that had been generated in situ from acetyl chloride and dry methanol) was added dropwise. This mixture was stirred at room temperature for 8 hours until all starting material was consumed. The mixture was evaporated in vacuo and then azeotroped with toluene (3×50 mL). The resulting oil was suspended in acetonitrile (35 mL), cooled to ice bath temperature, then benzylsulfonyl chloride (2.1 g, 11.1 mole) and pyridine (2.9 g, 37.1 mole) were added. The reaction was removed from the ice bath after 30 minutes and allowed to stir at room temperature for 18 hours. The reaction mixture was reduced in volume in vacuo. The oil was taken up in 200 mL ethyl acetate and washed successively with 1 N hydrochloric acid (1×50 mL), saturated sodium bicarbonate (1×50 mL) and brine (1×50 mL). After drying with MgSO$_4$, the organic phase was reduced in vacuo to provide the desired sulfonamide product.

Example 91

Preparation of N-benzylsulfonyl-S-(carboxymethyl)-L-cysteine sulfone sarcosine benzyl ester.

A solution of the compound of Example 90 (5.5 g, 10.0 mole) in dichloromethane (100 mL) was added fluoroacetic acid (100 mL) and the mixture was stirred at room temperature for 4 hours, at which time starting material was consumed. The mixture was evaporated in vacuo to provide the desired acid.

Example 92

Preparation of N-benzylsulfonyl-S-((R)-alphamethyl/benzyl carboxymethyl amide)-L-cysteine sulfone sarcosine benzyl ester.

To a solution of the compound of Example 91 (4.94 g, 10.0 mmole) in N,N-dimethyl formamide (40 mL) was added 1-ethyl-3-(3-dimethylaminopropyl)carbodiimide hydrochloride salt (2.1 g, 11.0 mmole) and 1-hydroxybenzotriazole monohydrate (2.3 g, 15.0 mmole). The mixture was stirred for 15 minutes then (R)-alpha methyl benzyl amine (2.5 mL, 20.0 mmole) was added and the reaction stirred at room temperature for 12 hours. The reaction mixture was diluted with ethyl acetate (300 mL) and washed successively with saturated sodium bicarbonate (1×75 mL), brine (1×75 mL) and 1M hydrochloric acid (1×75 mL). The organic phase was dried over MgSO$_4$, filtered and the volume reduced in vacuo to provide the desired carboxyamide.

Example 93

Preparation of N-benzylsulfonyl-S-((R)-alpha methyl benzyl carboxymethyl amide)-L-cysteine sulfone sarcosine acid.

To a solution of the compound of Example 92 (5.97 g, 10.0 mmole) in methanol (100 mL) was added 1.0 g of 10% palladium on carbon and the mixture was stirred under hydrogen gas at atmospheric pressure for 24 hours. The mixture was then filtered through a short plug of celite and the volume was reduced in vacuo to provide the corresponding acid.

Example 94

Preparation of N-benzylsulfonyl-L-cysteine sulfone-S-((R)-alpha methyl benzylcarboxyamide)-sarcosine cyclic nitro arginine ethyl aminal.

To a solution of Example 93 (5.1 g, 10.0 mmole) in N,N-dimethyl formamide (25 mL) was added 1-ethyl-3-(3-dimethylaminopropyl)carbodiimide hydrochloride salt (1.9 g, 10.0 mmole) followed by 1-hydroxybenzotriazole monohydrate (2.3 g, 15.0 mmole) and the reaction stirred for 30 minutes. Then cyclic nitroarginine ethyl aminal hydrochloride (4.0 g, 15.0 mmole) was added followed by N-methyl morpholine (2.2 ml, 20.0 mmole). The reaction is then stirred at room temperature for 18 hours. The reaction is diluted with ethyl acetate (300 mL) and washed successively with saturated sodium bicarbonate (1×100 mL), brine (1×100 mL) and 1M aqueous hydrochloric acid (1×100 mL). The organic phase was dried over MgSO$_4$, filtered and the solvent removed in vacuo to provide the desired coupled product.

Example 95

Preparation of N-benzylsulfonyl-L-cysteinesulfone-S-((R)-alpha methyl benzyl carboxyamide)-sarcosine cyclic arginine ethyl aminal.

To a solution of Example 94 (8.6 g, 10.0 mmole) in water (60 mL), acetic acid (20 mL) and methanol (600 mL) in a 2000 mL Parr bottle was added 5.0 g of 10% palladium on carbon. The mixture was then shaken under a hydrogen atmosphere of 40 psi for 3 days. The catalyst was then removed by filtration and the filtrate concentrated in vacuo. The product was azeotroped with toluene to remove residual acetic acid to afford the title compound.

Example 96

Preparation of N-benzylsulfonyl-L-cysteinesulfone-S-((R)-alpha methyl benzyl carboxyamide)-sarcosine argininal.

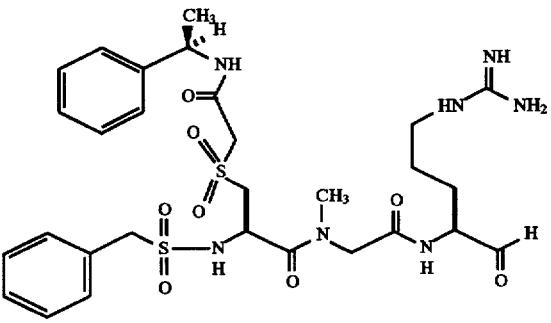

The compound of Example 95 (8.1 g, 10.0 mmole) was dissolved in 200 mL of 1:1 water:acetonitrile with stirring and cooled to 0° C. in an ice water bath. To this solution was slowly added 300 mL of a 60 wt % solution of hexafluorophosphoric acid in water. After 1 hour analytical HPLC (20–60% acetonitrile/water containing 0.1% trifluoroacetic acid) indicated complete hydrolysis of the starting compound. The pH of the reaction mixture was adjusted to pH=4 using 3.0M aqueous sodium acetate. This mixture was filtered through a short plug of celite and was then purified by preparative HPLC to provide the title compound.

Using the methods described in the above Examples, the following additional compounds were synthesized.

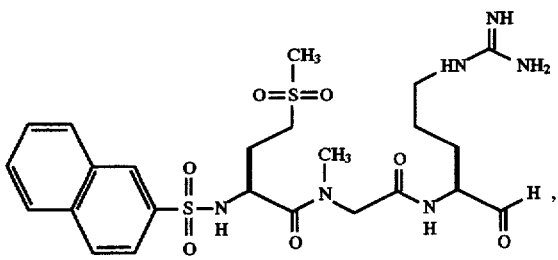

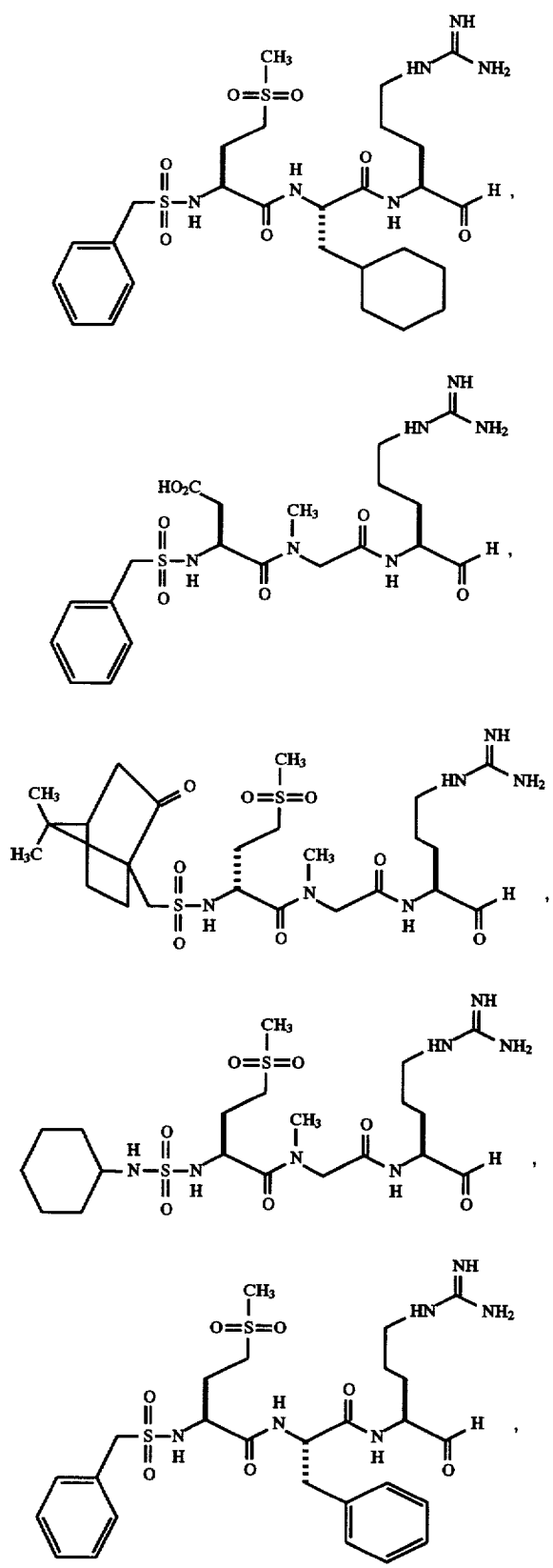

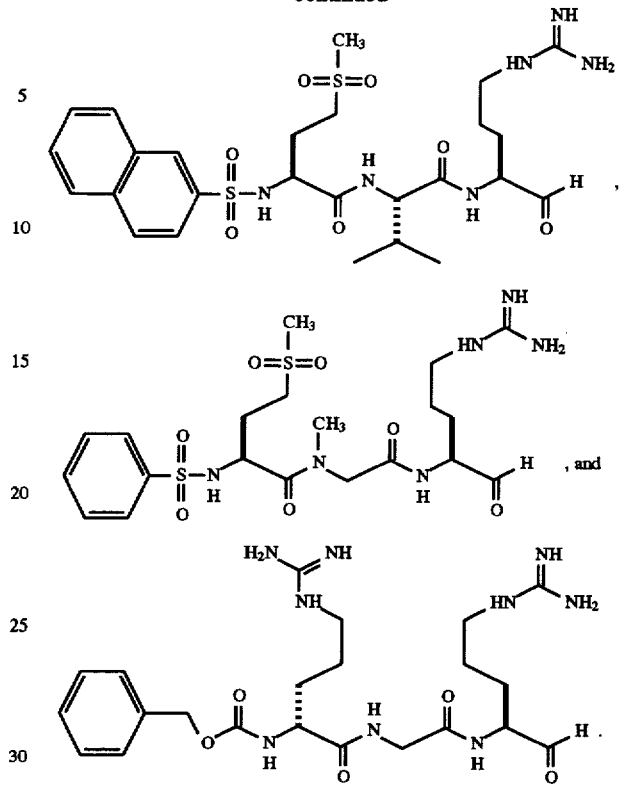

Example A

Determination of $IC_{50}$.

The ability of the compounds of the present invention to act as inhibitors of factor Xa catalytic activity was assessed by determining the concentration which inhibited enzyme activity by 50%, ($IC_{50}$), using the purified human factor Xa.

The buffer used for all assays was HBSA (10 mM HEPES, pH 7.5, 150 mM sodium chloride, 0.1% bovine serum albumin).

The assay was conducted by combining in appropriate wells of a Corning microtiter plate, 50 microliters of HBSA, 50 microliters of the test compound diluted in HBSA (or HBSA alone for uninhibited velocity measurement), and 50 microliters of the enzyme diluted in HBSA (prepared from purified human factor X obtained from Enzyme Research Laboratories according to the method described by Bock, P. E. et al. (1989) Archives of Biochem. Biophys. 273: 375. The enzyme was diluted into HBSA prior to the assay in which the final concentration was 0.5 nM). Following a 30 minute incubation at ambient temperature, 50 microliters of the substrate S2765 (N-alpha-benzyloxycarbonyl-D-argininyl-L-glycyl-L-arginine-p-nitroanilide dihydrochloride, obtained from Kabi Diagnostica and made up in deionized water followed by dilution in HBSA prior to the assay) was added to the wells yielding a final total volume of 200 microliters and a final concentration of 250 micromolar (about 5-times Km). The initial velocity of chromogenic substrate hydrolysis was measured by the change in absorbance at 405 nm using a Thermo Max® Kinetic Microplate Reader over a 5 minute period in which less than 5% of the added substrate was utilized. The concentration of added inhibitor which caused a decrease in the initial rate of hydrolysis was defined as the $IC_{50}$ value.

Table 1 shows the IC$_{50}$ for preferred compounds of the present invention.

TABLE 1

IC$_{50}$ of Preferred Compounds.

| Compound | IC$_{50}$ (nM) |
| --- | --- |
| [structure] | 0.0082 |
| [structure] | 0.0017 |
| [structure] | 0.032 |
| [structure] | 0.0018 |
| [structure] | 0.637 |

TABLE 1-continued

IC$_{50}$ of Preferred Compounds.

| Compound | IC$_{50}$ (nM) |
|---|---|
| | 0.0073 |
| | less than 0.025 |
| | 0.0046 |
| | 0.101 |
| | 0.926 |

TABLE 1-continued

IC$_{50}$ of Preferred Compounds.

| Compound | IC$_{50}$ (nM) |
|---|---|
| [structure] | 0.614 |

The specificity of compounds of the present invention is determined using the following assays.

Thrombin Assay

Thrombin catalytic activity was determined using the chromogenic substrate Pefachrome t-PA (CH$_3$SO$_2$-D-hexahydrotyrosine-glycyl-L-arginine-p-nitroaniline, obtained from Pentapharm Ltd.). The substrate was made up in deionized water followed by dilution in HBSA prior to the assay in which the final concentration was 300 micromolar (about 5-times Km). Purified human alpha-thrombin was obtained from Enzyme Research Laboratories, Inc. The enzyme was diluted into HBSA prior to the assay in which the final concentration was 0.25 nM.

Recombinant tissue plasminogen activator (rt-PA)

rt-PA catalytic activity was determined using the substrate, Pefachrome t-PA (CH$_3$SO$_2$-D-hexahydrotyrosine-glycyl-L-arginine-p-nitroaniline, obtained from Pentapharm Ltd.). The substrate was made up in deionized water followed by dilution in HBSA prior to the assay in which the final concentration was 500 micromolar (about 3-times Km). Human rt-PA (Activase®) was obtained from Genentech Inc. The enzyme was reconstituted in deionized water and diluted into HBSA prior to the assay in which the final concentration was 1.0 nM.

Plasmin Assay

Plasmin catalytic activity was determined using the chromogenic substrate, S-2251 [D-valyl-L-leucyl-L-lysine-p-nirtoanilide dihydrochloride], which was obtained from Kabi Diagnostica. The substrate was made up in deionized water followed by dilution in HBSA prior to the assay in which the final concentration was 300 micromolar (about 2.5-times Km). Purified human plasmin was obtained from Enzyme Research Laboratories, Inc. The enzyme was diluted into HBSA prior to assay in which the final concentration was 1.0 nM.

Activated Protein C (aPC)

aPC catalytic activity was determined using the chromogenic substrate, Pefachrome PC (delta-carbobenzyloxy-D-lysine-L-prolyl-L-arginine-p-nitroaniline dihydrochloride), obtained from Pentapharm Ltd.). The substrate was made up in deionized water followed by dilution in HBSA prior to the assay in which the final concentration was 250 micromolar (about 3-times Km). Purified human aPC was obtained from Hematologic Technologies, Inc. The enzyme was diluted into HBSA prior to assay in which the final concentration was 1.0 nM.

Chymotrypsin

Chymotrypsin catalytic activity was determined using the chromogenic substrate, S-2586 (methoxy-succinyl-L-arginine-L-prolyl-L-tyrosyl-p-nitroanilide), which was obtained from Kabi Diagnostica. The substrate was made up in deionized water followed by dilution in HBSA prior to the assay in which the final concentration was 100 micromolar (about 9-times Km). Purified (3×-crystallized; CDI) bovine pancreatic alpha-chymotrypsin was obtained from Worthington Biochemical Corp. The enzyme was reconstituted in deionized water and diluted into HBSA prior to assay in which the final concentration was 1.0 nM.

Trypsin

Trypsin catalytic activity was determined using the chromogenic substrate, S-2222 (benzoyl-L-isoleucine-L-glutamic acid [gamma-methyl ester]-L-arginine-p-nitroanilide), which was obtained from Kabi Diagnostica. The substrate was made up in deionized water followed by dilution in HBSA prior to the assay in which the final concentration was 250 micromolar (about 4-times Km). Purified (3×-crystallized;TRL3) bovine pancreatic trypsin was obtained from Worthington Biochemical Corp. The enzyme was reconstituted in deionized water and diluted into HBSA prior to assay in which the final concentration was 0.5 nM.

Example B

Ex vivo anticoagulant effects of (D)-camphorsulfonyl aspartyl sarcosine arginine aldehyde in human plasma.

The ex vivo anticoagulant effect of a compound of the present invention, (D)-camphorsulfonyl aspartyl sarcosine arginine aldehyde (Example 56), was determined by measuring the prolongation of the activated partial thromboplastin time (APTT) and prothrombin time (PT) over a broad concentration range of the added inhibitor, using pooled normal human plasma.

Fresh frozen citrated pooled normal human plasma was obtained from George King Biomedical, Overland Park, Kansa. The measurements for the APTT and PT were made using the Coag-A-Mate RA4 automated coagulometer (General Diagnostics, Organon Technica, Oklahoma City, Okla.) using Platelin® L or Simplastin® Excel (Organon Technica, Durham, N.C.) as the initiators of clotting, respectively, according to the manufacturers instructions. The assays were conducted by making a series of dilutions of the test compound in rapidly thawed plasma followed by adding either 200 microliters or 100 microliters to the wells of the assay carousel for the APTT and PT measurement, respectively.

Figure 2:
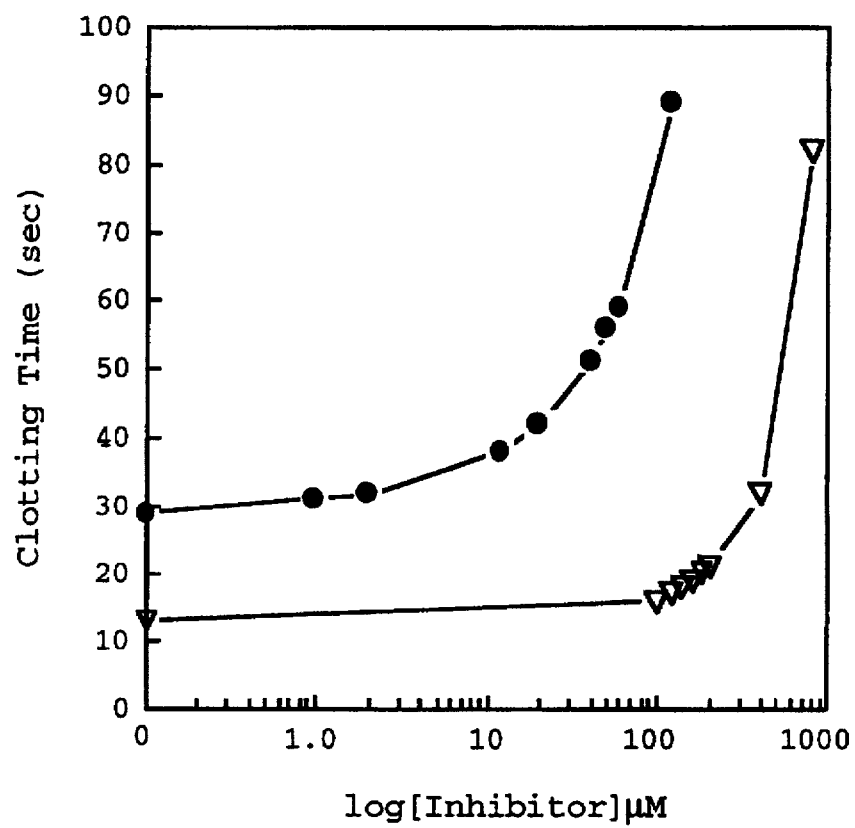
FIG. 2 depicts the anticoagulant effect of (D)-camphorsulfonyl aspartyl sarcosine arginine aldehyde measured in citrated human plasma using the activated partial thromboplastin time (APTT) assay, closed circles (1), and prothrombin time (PT) assay, open triangles (D). The control clotting times (0 inhibitor) for the APTT and PT assays in human plasma were 29 seconds and 13 seconds, respectively. The concentration of (D)-camphorsulfonyl aspartyl sarcosine arginine aldehyde which caused a doubling of the control clotting times in the APTT and PT assays were 54 micromolar and 298 micromolar, respectively. The data is the mean of two independent determinations.

As shown in FIG. 2, (D)-camphorsulfonyl aspartyl sarcosine arginine aldehyde prolonged the APTT in a dose dependent manner in human plasma demonstrating an anticoagulant effect in humans. This would lead one skilled in the art to conclude that this compound will be an effective antithrombotic agent in humans.

We claim:
1. A compound of the formula:

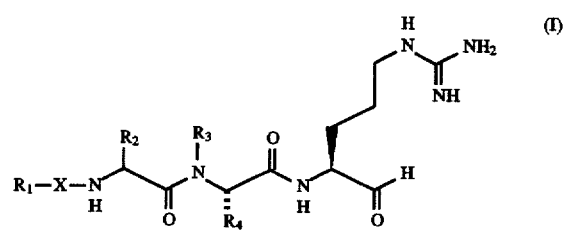

wherein (a) X is selected from the group consisting of —S(O)$_2$—, —N(R')—S(O)$_2$—, —C(=O)—, —OC(=O)—, —NH—C(=O)—, and a direct link, wherein R' is hydrogen, or alkyl of 1 to about 4 carbon atoms;

(b) R$_1$ is selected from the group consisting of:
  (1) alkyl of 1 to about 12 carbon atoms,
  (2) alkyl of 1 to about 3 carbon atoms substituted with cyclic alkyl of about 5 to about 8 carbon atoms,
  (3) alkenyl of about 3 to about 6 carbon atoms which is optionally substituted with cyclic alkyl of about 5 to about 8 carbon atoms,
  (4) aryl of about 4 to about 14 carbon atoms which is optionally mono-substituted with Y$_1$ or optionally di-substituted with Y$_1$ and Y$_2$,
  (5) aralkyl of about 5 to about 15 carbon atoms which is optionally mono-substituted in the aryl ring with Y$_1$ or optionally di-substituted in the aryl ring with Y$_1$ and Y$_2$,
  (6) aralkenyl of about 6 to about 15 carbon atoms which is optionally mono-substituted in the aryl ring with Y$_1$ or optionally di-substituted in the aryl ring with Y$_1$ and Y$_2$,

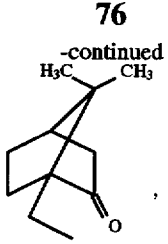

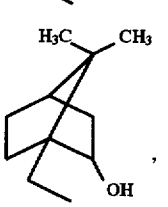

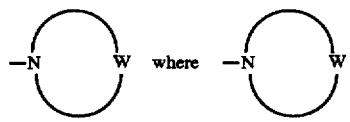

(11) perfluoroalkyl of 1 to about 12 carbon atoms,
(12) perfluoroaryl of about 6 to about 14 carbon atoms,
(13) perfluoroaryl alkyl of about 7 to about 15 carbon atoms, and
(14)

is a 5 to 7 member heterocycle of 3 to 6 ring carbon atoms, where W is —CH$_2$—, —O—, —S(=O)—, —S(O)$_2$— or —S—, where Y$_1$ and Y$_2$ are independently selected from halogen, —CF$_3$, —CF$_2$CF$_3$, —CH(CF$_3$)$_2$, —C(OH)(CF$_3$)$_2$, cyano, nitro, —C(O)OH, —C(O)OZ$_1$, —Z$_1$, —OZ$_1$, —OH, —NH$_2$, —NHZ$_1$, —NZ$_1$Z$_2$, —P(O)$_3$H$_2$, —P(O)$_3$(Z$_1$)$_2$, tetrazolyl, —S(O)$_3$H and —S(O)$_m$Z$_1$ wherein m is 0, 1 or 2, Z$_1$ and Z$_2$ are independently selected from the group consisting of alkyl of 1 to about 6 carbon atoms, aryl of about 3 to about 14 carbon atoms and aralkyl of about 4 to about 15 carbon atoms, with the provisos that:
(1) when Y$_1$ is halogen, then Y$_2$ is hydrogen or halogen;
(2) when Y$_1$ is —C(O)OH, then Y$_2$ is hydrogen, —OH or —C(O)OH;
(3) when Y$_1$ is —C(O)OZ$_1$, then Y$_2$ is hydrogen, —OH or —C(O)OZ$_1$;
(4) when Y$_1$ is —Z$_1$, then Y$_2$ is hydrogen, —OH or —Z$_1$;
(5) when Y$_1$ is —CF$_3$, then Y$_2$ is hydrogen, —OH or —CF$_3$;
(6) when Y$_1$ is —OZ$_1$, then Y$_2$ is hydrogen, —OH or —OZ$_1$;
(7) when Y$_1$ is —OH, then Y$_2$ is hydrogen, —OH, —C(O)OH, C(O)OZ$_1$, —CF$_3$, —S(O)$_3$H, or —S(O)$_m$Z$_1$; and
(8) when Y$_1$ is cyano, nitro, —P(O)$_3$H$_2$, —P(O)$_3$(Z$_1$)$_2$, —NH$_2$, —NHZ$_1$, —NZ$_1$Z$_2$, or tetrazolyl, then Y$_2$ is hydrogen;

(c) R$_2$ is selected from the group consisting of hydrogen, —CH$_2$CH$_2$CH$_2$NHC(=NH)NH$_2$, —CH$_2$CH$_2$S(O)$_2$CH$_3$, —CH$_2$C(O)OH, —CH$_2$C(O)OCH$_3$, —CH$_2$S(O)$_2$(CH$_2$)$_n$C(O)Z$_3$,

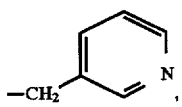

—CH₂S(O)₂Z₄, —(CH₂)ₙNH₂, —(CH)ₙC(O)NR₅R₆, and

wherein n=2, 3, 4, 5, or 6,

Z₃ is —OH, —OCH₃, or —NR₅R₆,

Z₄ is alkyl of 1 to about 4 carbon atoms, aryl of about 6 to about 14 carbon atoms, or aralkyl of about 7 to 16 carbon atoms, R₅ is hydrogen or methyl, R₆ is a cyclic alkyl of 1 to about 10 carbon atoms, an aralkyl of about 5 to about 15 carbon atoms optionally monosubstituted with Y₁, or heterocyclic hydrocarbyl of 5 to 10 ring atoms with 3 to about 9 ring carbon atoms and the remainder of the ring atoms are heteroatoms selected from oxygen, sulfur and nitrogen, optionally subustituted, wherein Y₁ is as defined above,

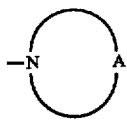

is 6,7-dimethoxy-1,2,3,4-tetrahydroisoquinolinyl, 4-hydroxy piperidyl, 4-keto piperidyl, N-morpholino, 3,4-methylenedioxybenzyl piperazinyl, 4-phenyl piperazinyl optionally mono-substituted with fluoro, chloro, methoxy, or trifluoromethyl, or 4-benzyl piperazinyl optionally mono-substituted with fluoro, chloro, methoxy, or trifluoromethyl, and pharmaceutically acceptible quaternary ammonium salts thereof;

(d) R₃ is selected from the group consisting of
(1) hydrogen;
(2) alkyl of 1 to about 8 carbon atoms optionally substituted with —OH;
(3) cyclic alkyl of about 3 to about 10 carbon atoms;
(4) alkyl of 1 to about 3 carbon atoms substituted with cyclic alkyl of about 5 to about 8 carbon atoms;
(5) aryl of about 3 to about 10 carbon atoms which is optionally mono-substituted with Y₁ or optionally disubstituted with Y₁ and Y₂;
(6) alkyl of 1 to about 3 carbon atoms substituted on the terminal carbon with aryl of about 4 carbon atoms to about 10 carbon atoms which is optionally mono-substituted with Y₁ or optionally disubstituted with Y₁ and Y₂; and (e) R₄ is selected from the group consisting of hydrogen, alkyl of 1 to about 7 carbon atoms optionally substituted with —OH, and alkyl of 1 to about 3 carbon atoms substituted on the terminal carbon atom with aryl of about 4 carbon atoms to about 10 carbon atoms which is optionally mono-substituted with Y₁, and pharmaceutically acceptable salts thereof.

2. A compound according to claim 1 wherein X is —S(O)₂—.

3. A compound according to claim 2 wherein R₁ is alkyl, aryl or aralkyl.

4. A compound according to claim 3 wherein Y₁ and Y₂ are independently selected from —C(O)OH, —C(O)OZ₁, —S(O)ₘZ₁, and —CF₃.

5. A compound according to claim 4 wherein R₁ is unsubstituted naphthyl, substituted naphthyl, unsubstituted phenyl, substituted phenyl, unsubstituted benzyl or substituted benzyl.

6. A compound according to claim 5 wherein R₁ is benzyl.

7. A compound according to claim 3 wherein R₁ is cyclohexyl or cyclohexylmethyl.

8. A compound according to claim 1 wherein R₂ is —CH₂CH₂CH₂NHC(=NH)NH₂.

9. A compound according to claim 8 wherein X is —S(O)₂—.

10. A compound according to claim 9 wherein R₁ is alkyl, aryl or aralkyl.

11. A compound according to claim 10 wherein Y₁ and Y₂ are independently selected from —C(O)OH, —C(O)OZ₁, —S(O)ₘZ₁, and —CF₃.

12. A compound according to claim 11 wherein R₁ is unsubstituted naphthyl, substituted naphthyl, unsubstituted phenyl, substituted phenyl, unsubstituted benzyl or substituted benzyl.

13. A compound according to claim 12 wherein R₁ is benzyl.

14. A compound according to claim 10 wherein R₁ is cyclohexyl or cyclohexylmethyl.

15. A compound according to claim 1 wherein X is —S(O)₂—, R₁ is aralkyl and R₂ is

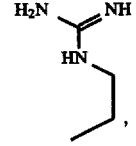

R₃ is methyl, cyclohexylmethyl, phenyl, or benzyl, and R₄ is hydrogen.

16. A compound according to claim 15 wherein R₁ is unsubstituted benzyl or substituted benzyl.

17. A compound according to claim 16 wherein Y₁ and Y₂ are independently selected from —C(O)OH, —C(O)OZ₁, —S(O)ₘZ₁, and —CF₃.

18. A compound according to claim 1 wherein R₂ is —CH₂CH₂S(O)₂CH₃.

19. A compound according to claim 18 wherein X is —S(O)₂— and R₁ is aralkyl.

20. A compound according to claim 19 wherein Y₁ and Y₂ are independently selected from —C(O)OH, —C(O)OZ₁, —S(O)ₘZ₁, and —CF₃.

21. A compound according to claim 1 wherein R₆ is selected from the group consisting of 3-(R)-quinuclidine, 3-(S)-quinuclidine, 4-trifluoromethyl-7-yl-coumarin, 4-methyl-7-yl-coumarin, 7-yl-coumarin, 3-yl-2-ethyl-4(3H)-quinazolinone, 2-yl-benzothiazole, 3-yl-benzoic acid, 3-yl-4-hydroxybenzoic acid, 4-hydroxy-1-methyl-6-phenyl-3-yl-2(1H)-pyridone, 1-adamantyl, ethyl morpholine, ethyl piperidine, 2-(2-ethyl)pyridine, 4-hydroxyphenethyl, (R)-alpha-methylbenzyl, (S)-alpha-ethylbenzyl, [(1R,2S)-(N-methyl-N-(1-ethyl))benzyl alcohol], [(1S,2R)-(N-methyl-N-(1-ethyl))benzyl alcohol], [(1R,2R)-(N-methyl-N-(1-ethyl))benzyl alcohol], [(1S,2S)-(N-methyl-N-(1-ethyl))benzyl alcohol], or [4-(methyl)-5-hydroxy-6-methyl-3-pyridine methanol].

22. A compound according to claim 1 of the formula:

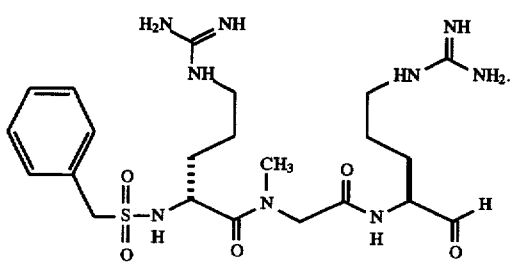

23. A compound according to claim 1 of the formula:

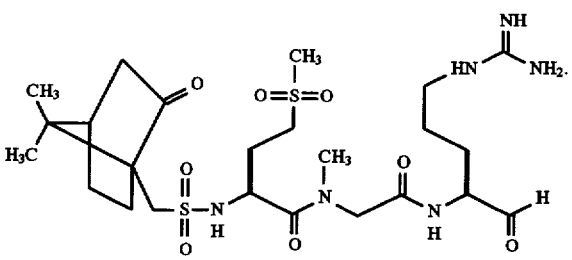

24. A compound according to claim 1 of the formula:

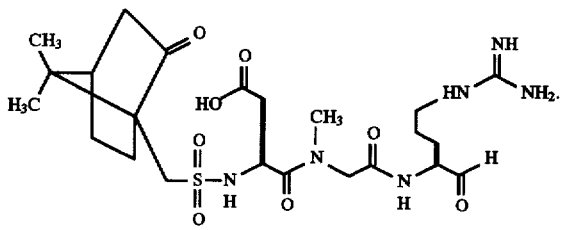

* * * * *